United States Patent [19]
Sakashita et al.

[11] Patent Number: 5,849,022
[45] Date of Patent: Dec. 15, 1998

[54] MEDICAL INSTRUMENT FOR USE IN COMBINATION WITH ENDOSCOPES

[75] Inventors: Kiyotoshi Sakashita, Hino; Toshihiko Hashiguchi, Sagamihara; Toru Shimizu, Akigawa; Katsumi Sasaki, Hachioji; Kenichi Kimura, Hachioji; Eiji Murakami, Hachioji; Koji Iida, Sagamihara; Yasuhiko Kikuchi, Machida; Toshiya Sugai, Hachioji, all of Japan

[73] Assignee: Olympus Optical Co., Ltd., Tokyo, Japan

[21] Appl. No.: 907,269

[22] Filed: Aug. 6, 1997

Related U.S. Application Data

[63] Continuation of Ser. No. 498,170, Jul. 5, 1995, abandoned.

[30] Foreign Application Priority Data

| Jul. 29, 1994 | [JP] | Japan | 6-179049 |
| Jul. 29, 1994 | [JP] | Japan | 6-179194 |
| Jan. 30, 1995 | [JP] | Japan | 7-012470 |

[51] Int. Cl.⁶ ............................................. A61B 17/28
[52] U.S. Cl. ..................... 606/174; 606/51; 606/52; 606/205
[58] Field of Search ................................. 606/205, 206, 606/170, 171, 174, 51, 52, 207; 600/564

[56] References Cited

U.S. PATENT DOCUMENTS

| 2,790,437 | 4/1957 | Moore . | |
| 3,895,636 | 7/1975 | Schmidt | 606/205 |
| 5,020,056 | 5/1991 | Hasson . | |
| 5,254,130 | 10/1993 | Poncet et al. | 606/205 X |
| 5,275,613 | 1/1994 | Haber et al. . | |
| 5,282,806 | 2/1994 | Haber et al. . | |
| 5,282,817 | 2/1994 | Hoogeboom et al. . | |
| 5,342,391 | 8/1994 | Foshee et al. | 606/205 |
| 5,370,659 | 12/1994 | Sakashita . | |

FOREIGN PATENT DOCUMENTS

| A-0 342 402 | 11/1989 | European Pat. Off. . |
| 0 484 671 A2 | 5/1992 | European Pat. Off. . |
| 7330291 U | 12/1973 | Germany . |
| 89 00 376 U | 4/1989 | Germany . |
| U-8 900 376 | 4/1989 | Germany . |
| 91 06 506 U | 9/1991 | Germany . |
| U-9 106 506 | 9/1991 | Germany . |
| 92 15 053 U | 5/1993 | Germany . |
| 5-285147 | 11/1993 | Japan . |
| 6-311987 | 11/1994 | Japan . |

*Primary Examiner*—Michael H. Thaler
*Attorney, Agent, or Firm*—Frishauf, Holtz, Goodman, Langer & Chick

[57] ABSTRACT

A medical instrument for use in combination with an endoscope having an operating shaft and a pair of tongs. The instrument has a drive mechanism provided between the operating shaft and the tongs, for opening and closing the tongs. The drive mechanism can apply an additional force to the tongs even after the tongs have closed completely.

24 Claims, 39 Drawing Sheets

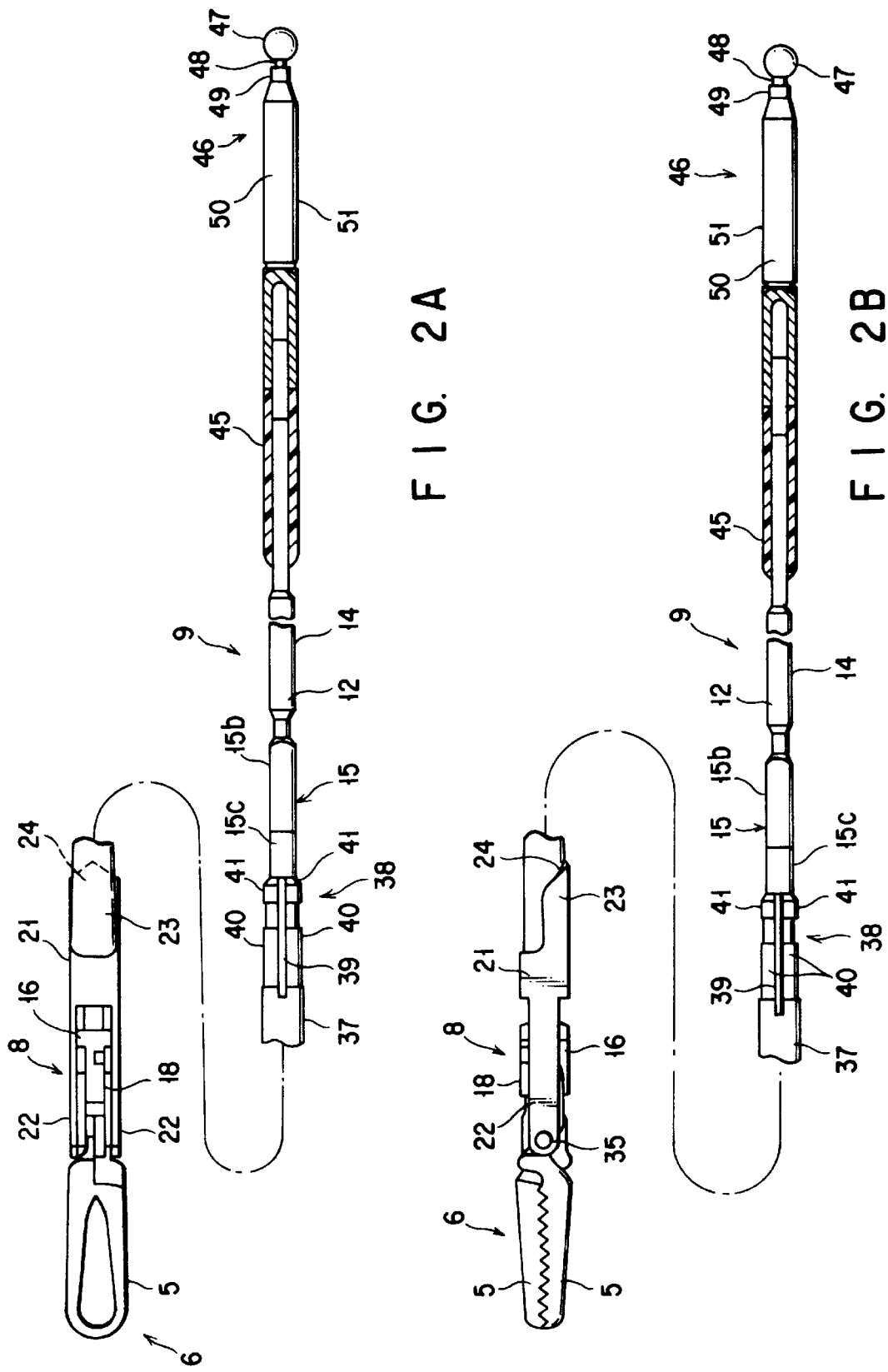

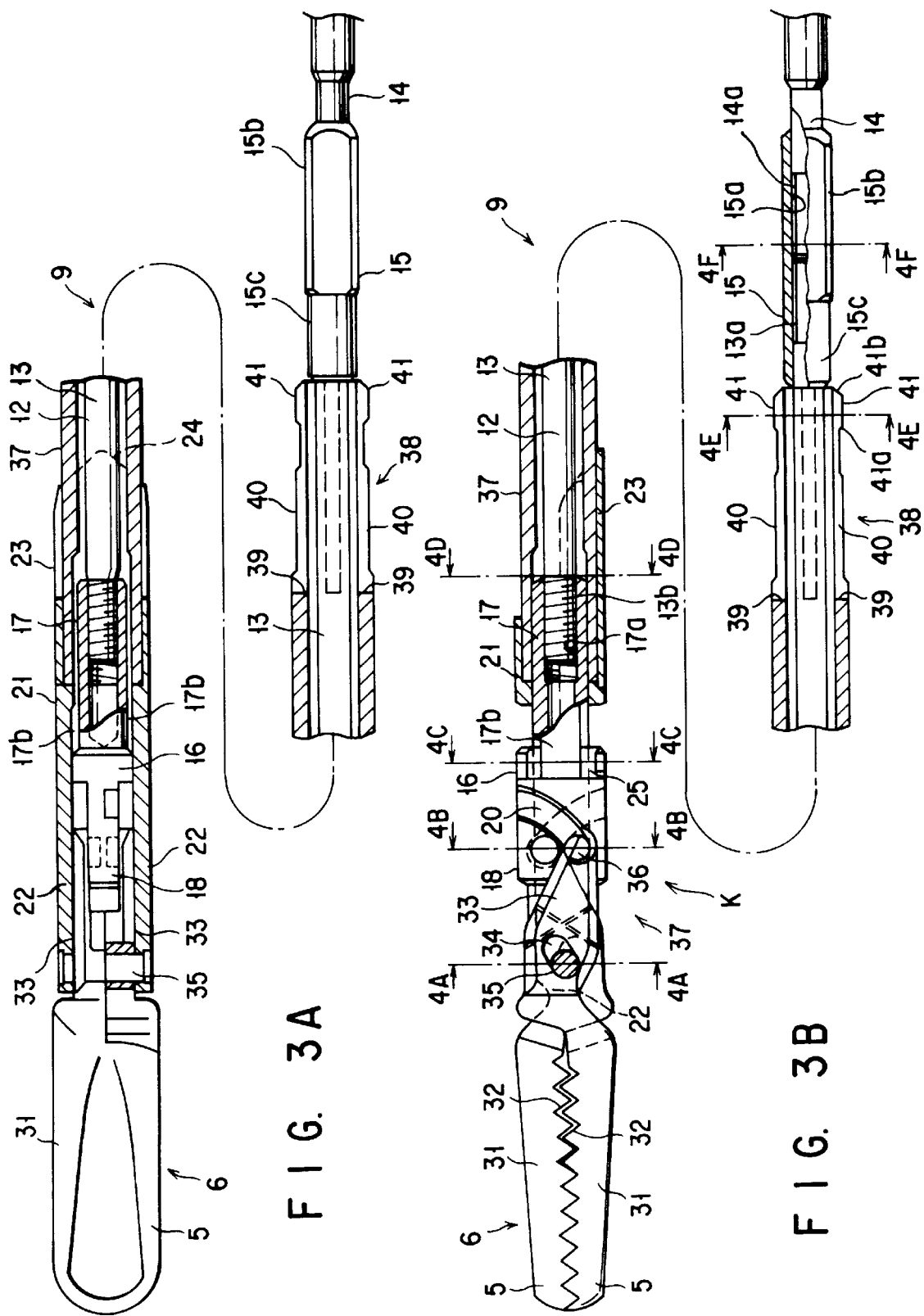

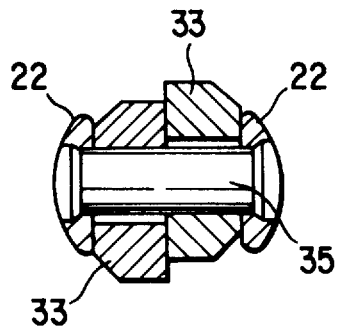
F I G. 4A
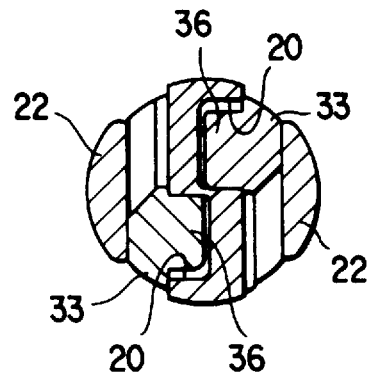
F I G. 4B
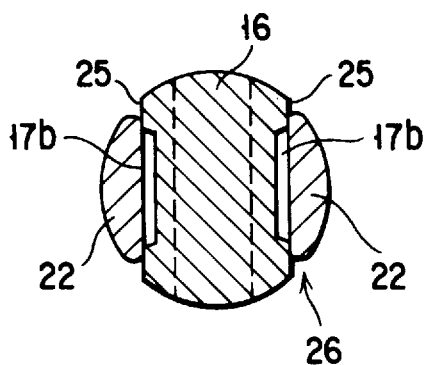
F I G. 4C
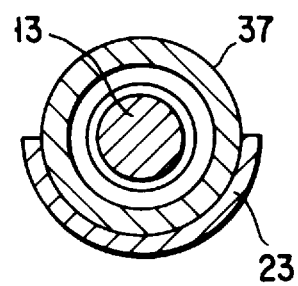
F I G. 4D
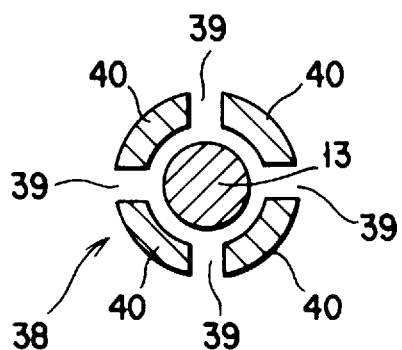
F I G. 4E
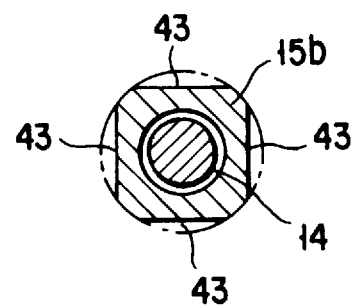
F I G. 4F

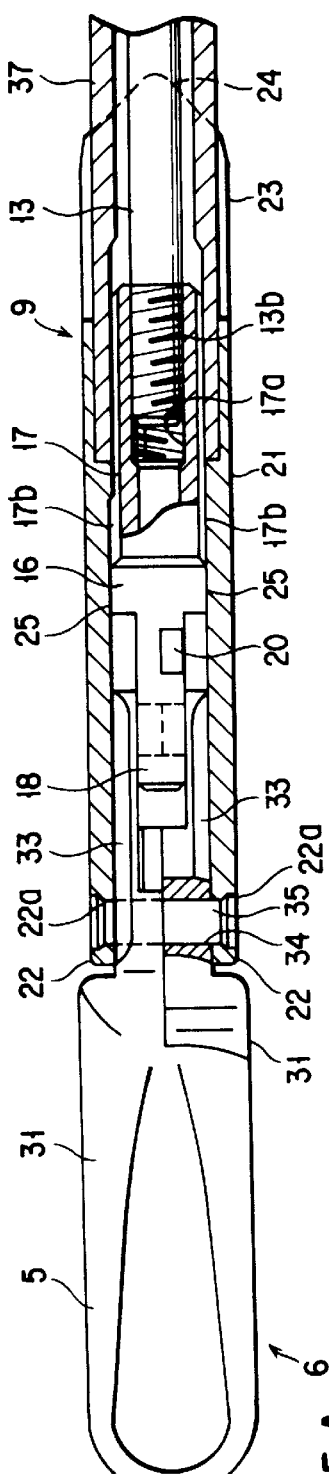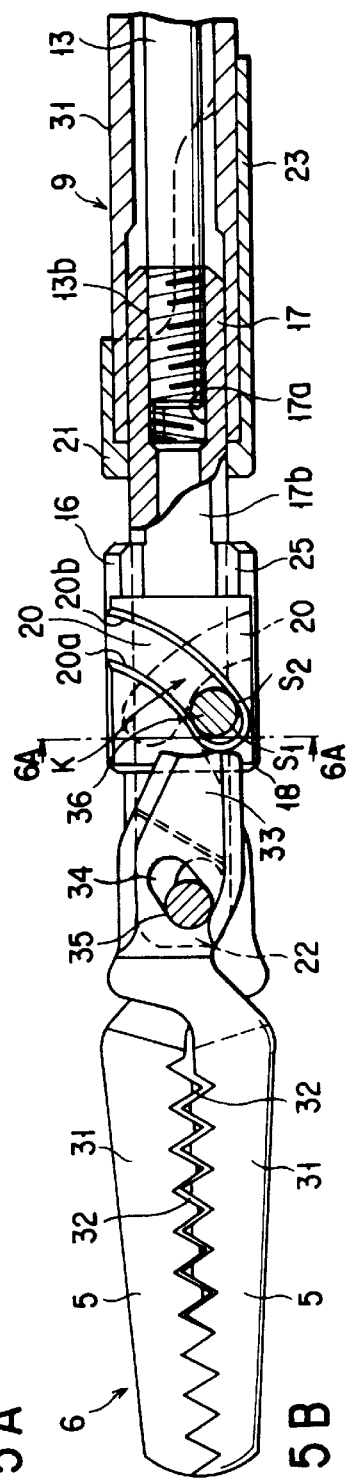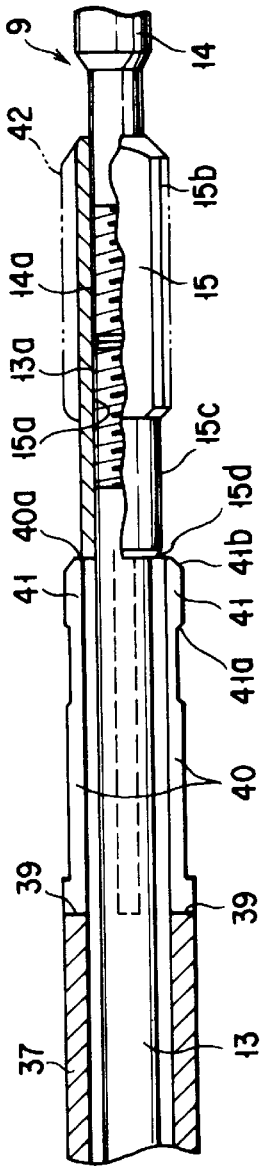
F I G. 5A  F I G. 5B  F I G. 5C

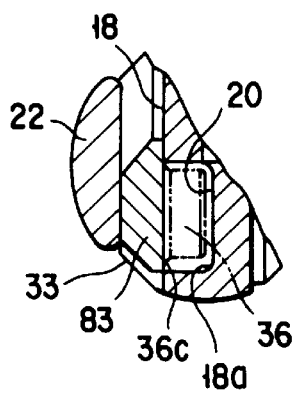
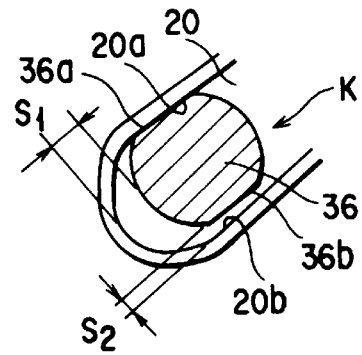
FIG. 6A          FIG. 6B
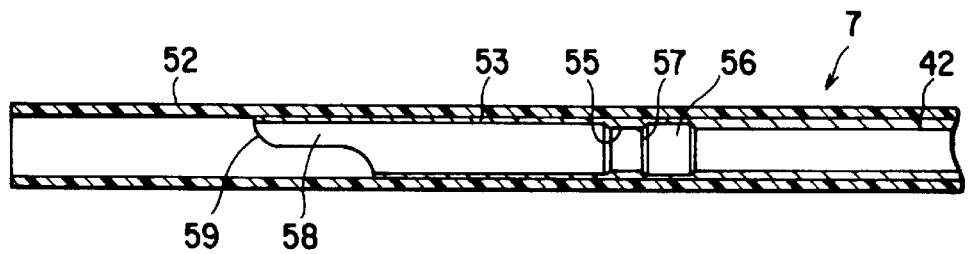
FIG. 7A
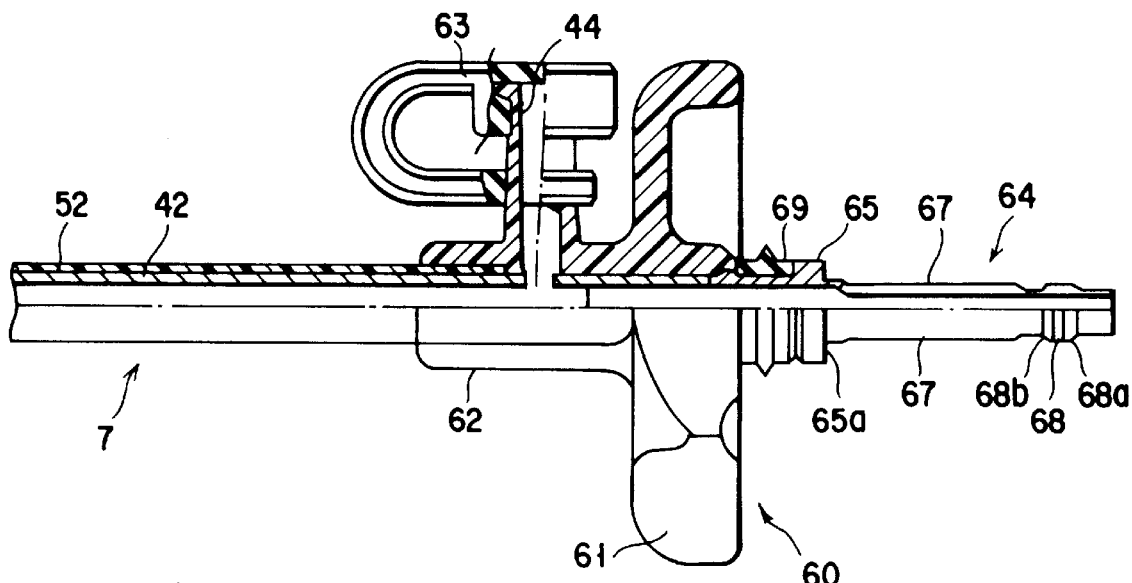
FIG. 7B

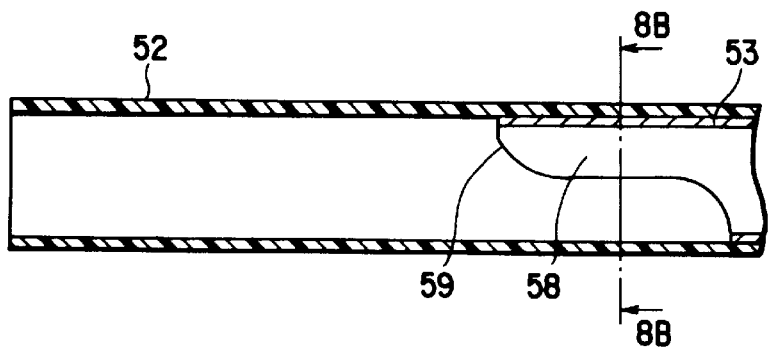
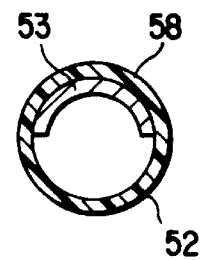
FIG. 8A
FIG. 8B
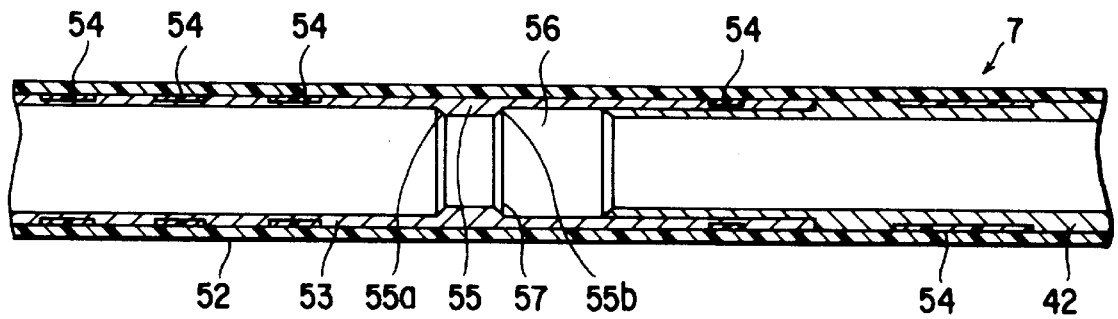
FIG. 8C
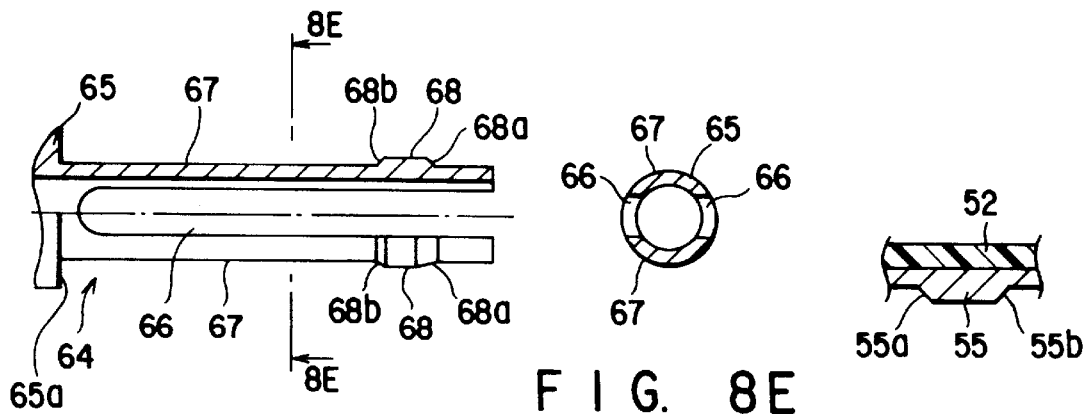
FIG. 8D
FIG. 8E
FIG. 8F

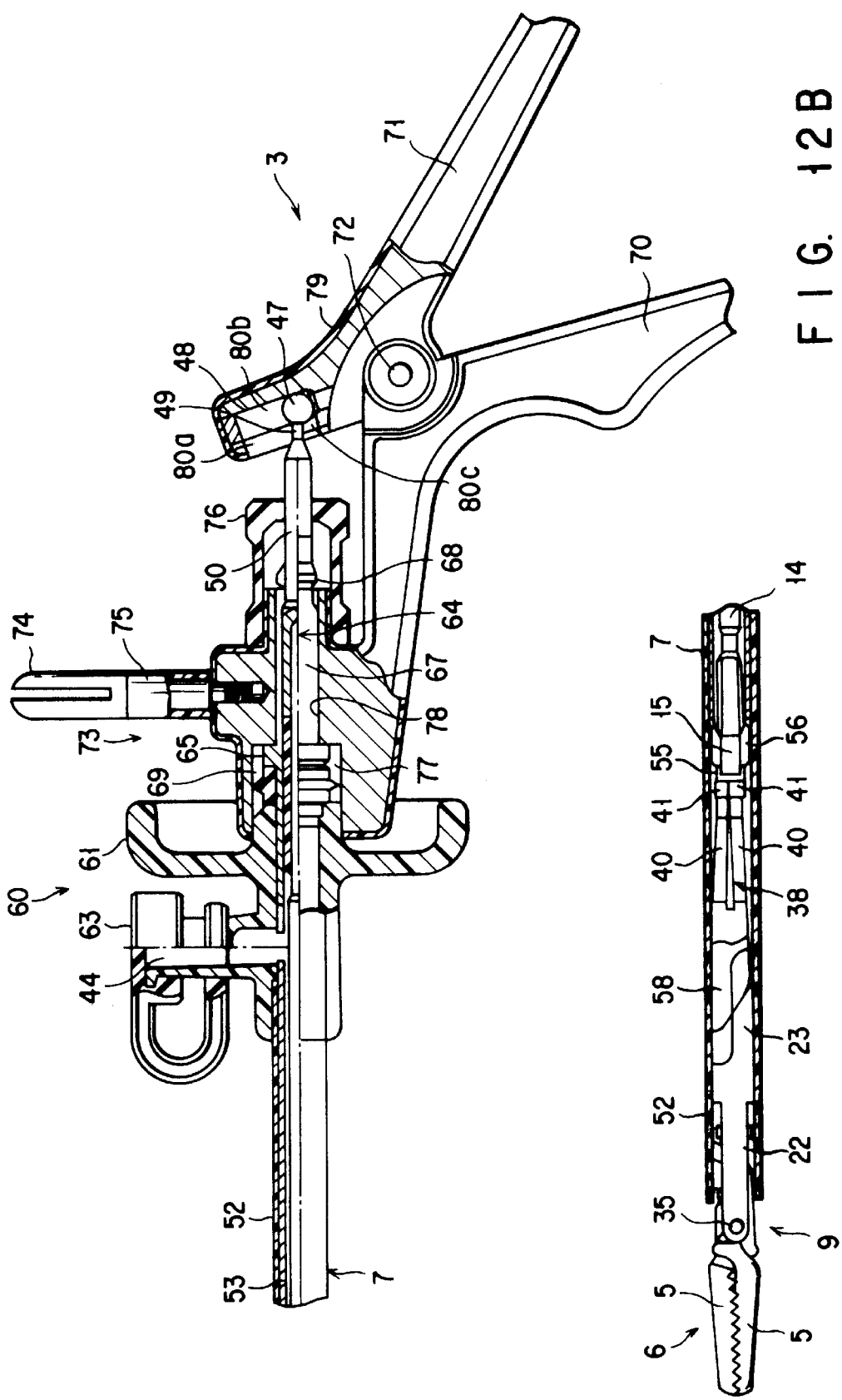

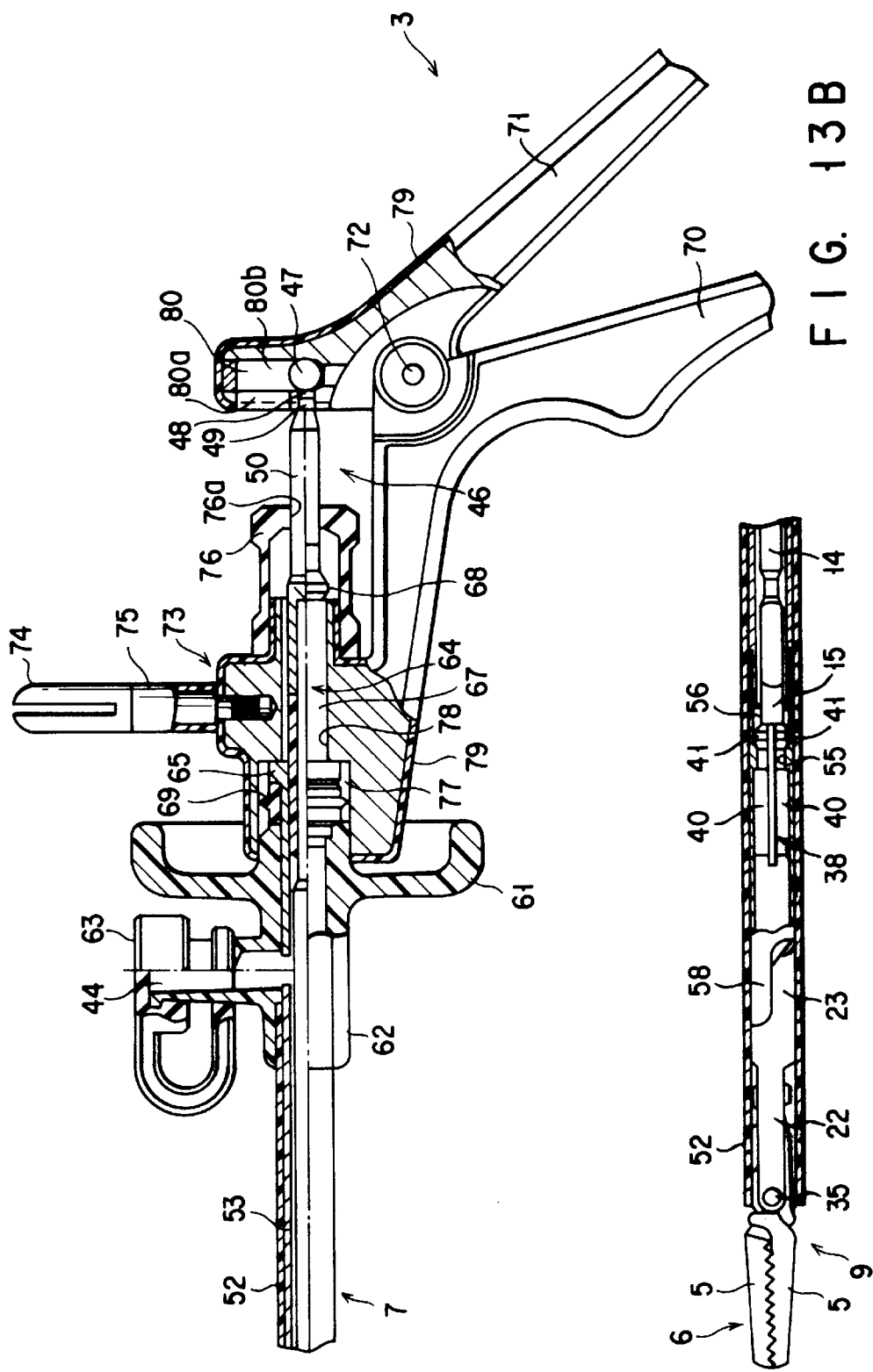

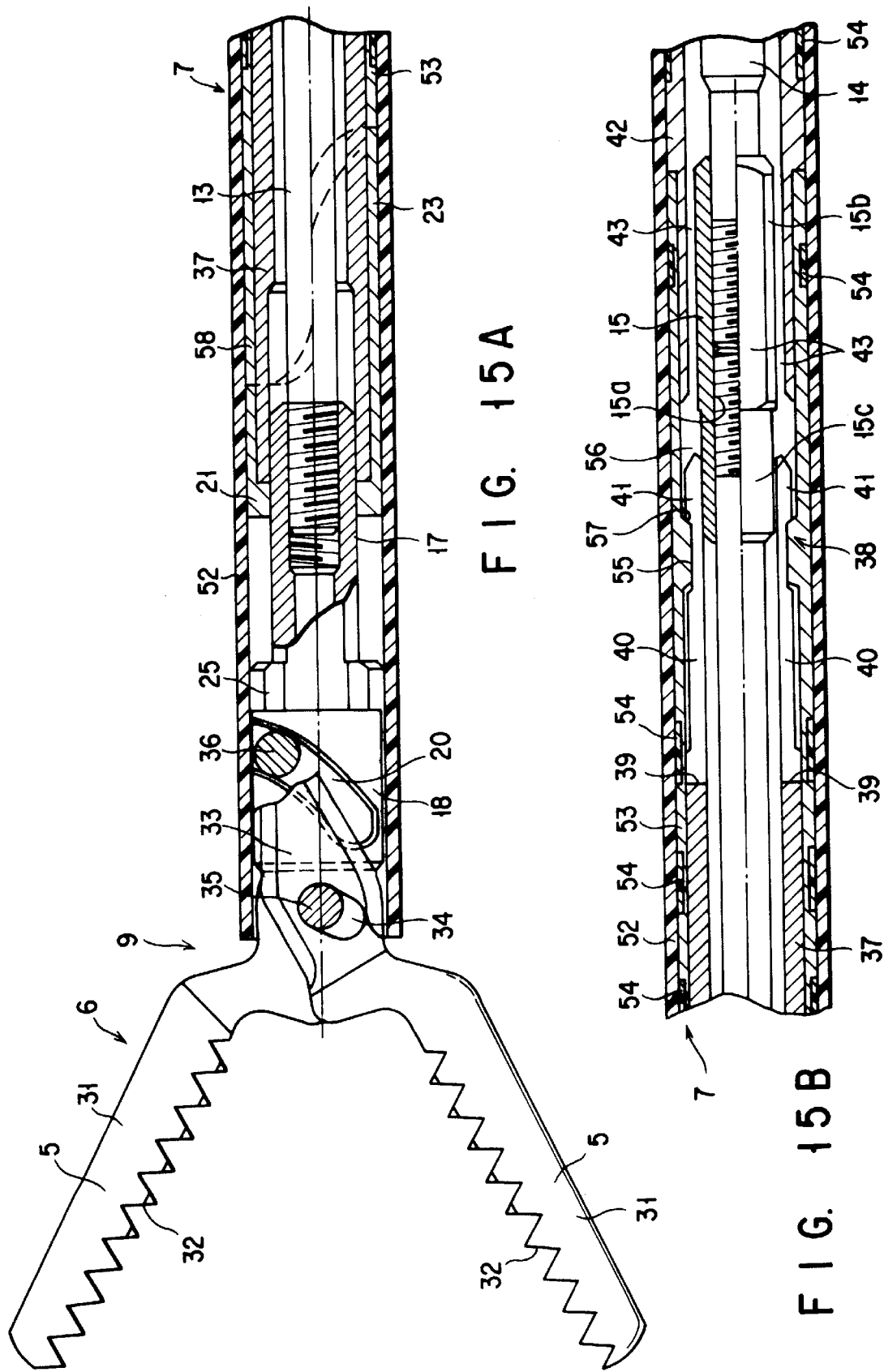

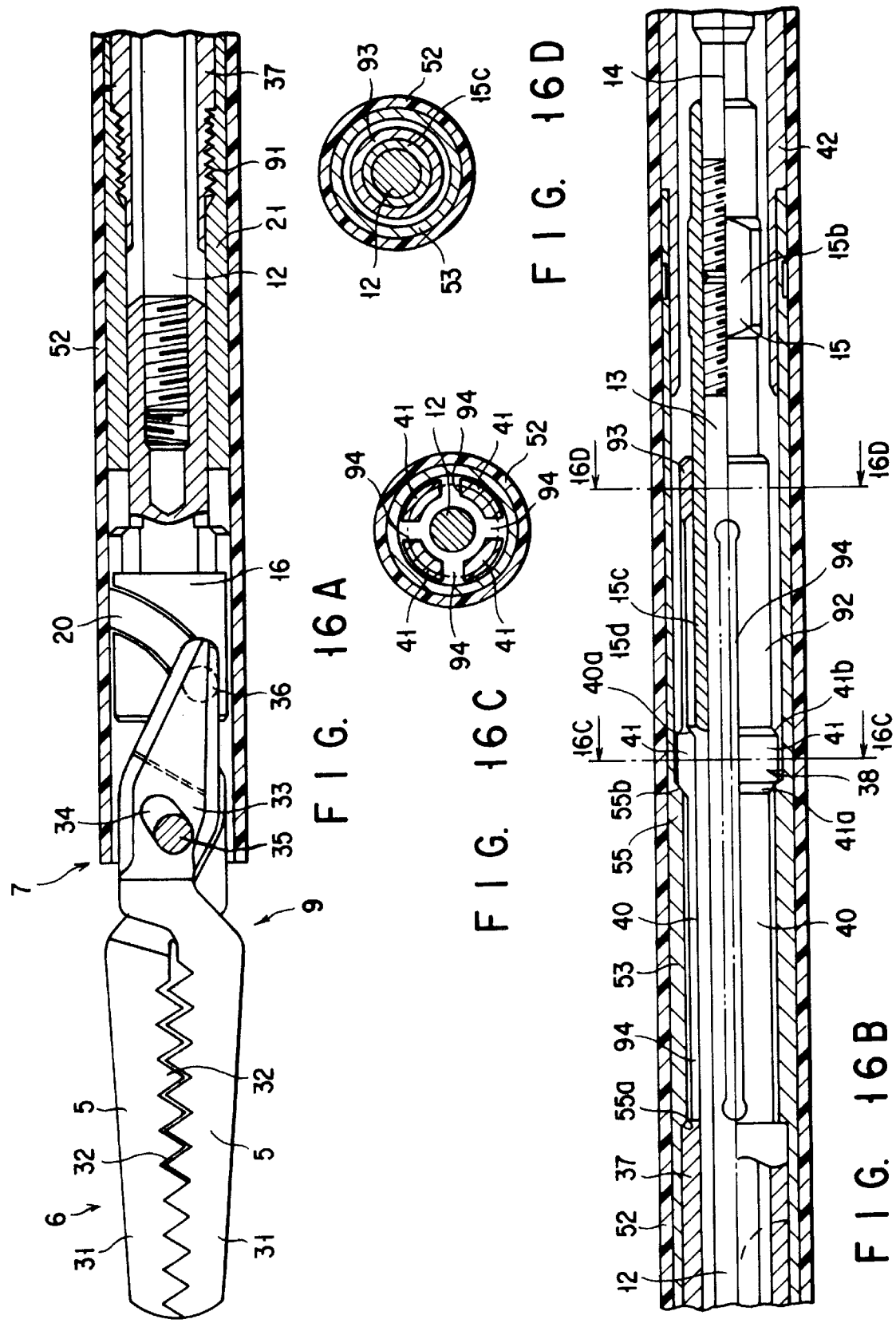

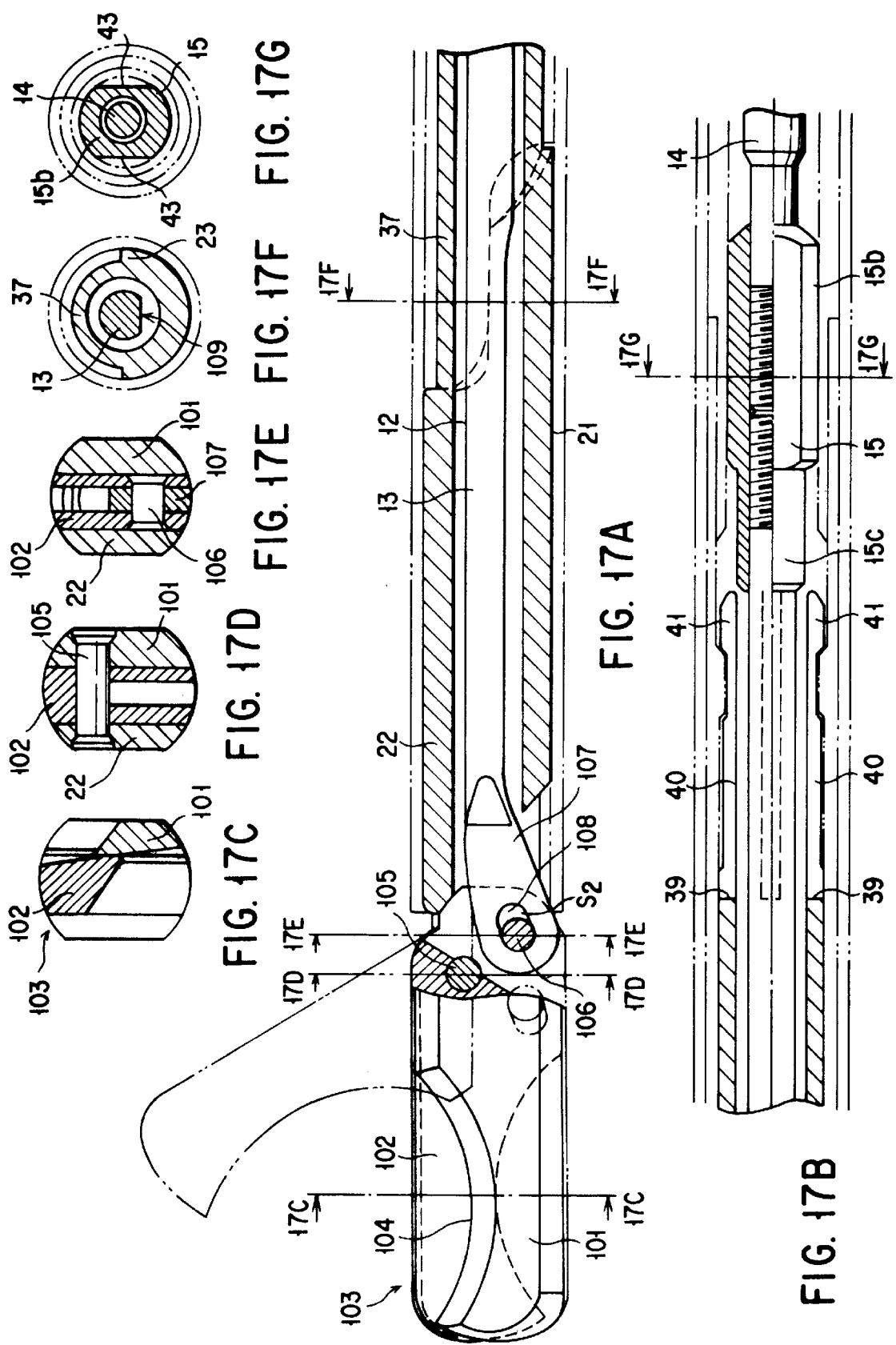

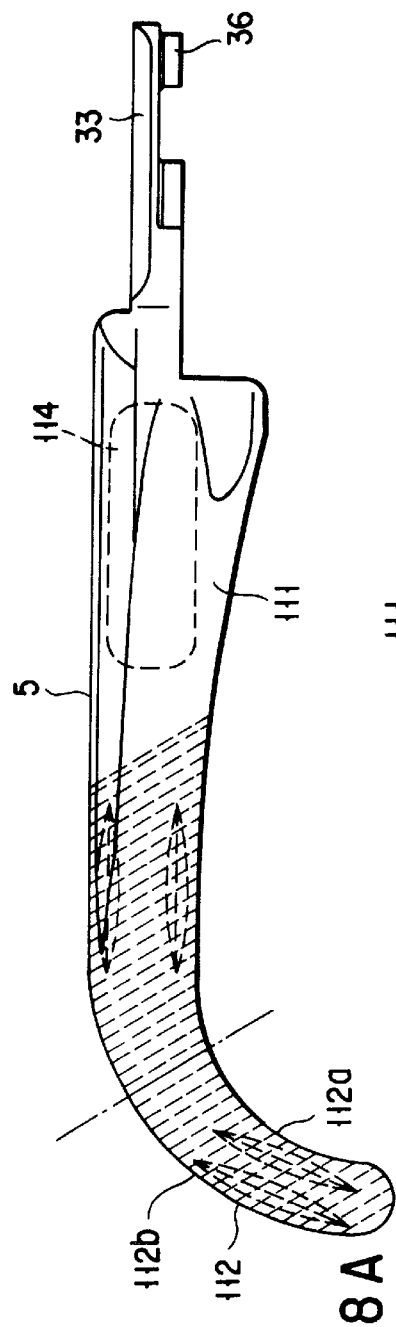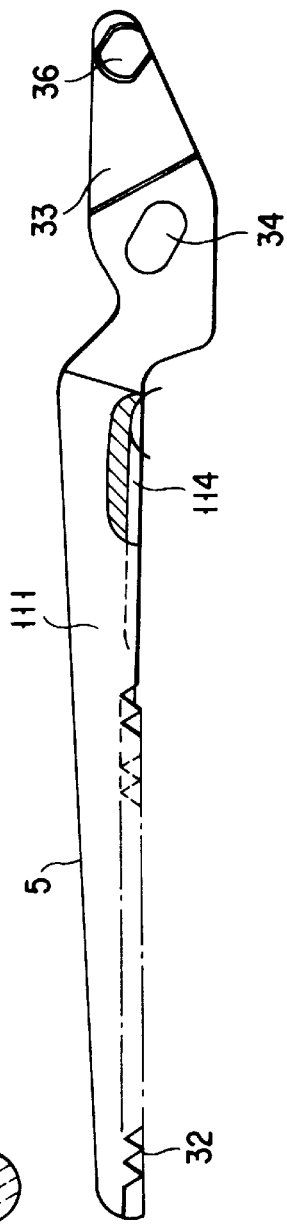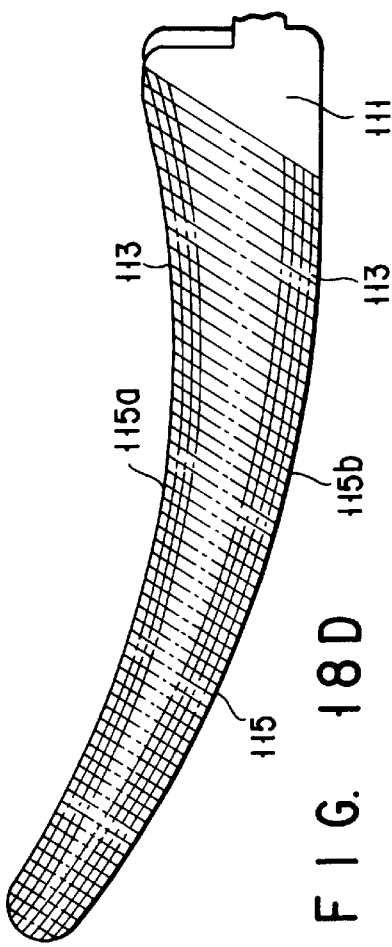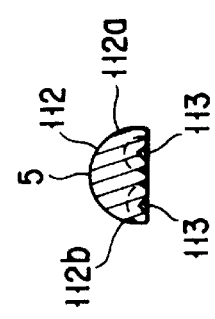
FIG. 18A
FIG. 18B
FIG. 18C
FIG. 18D

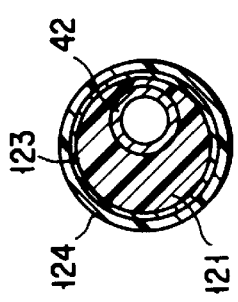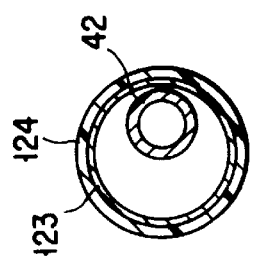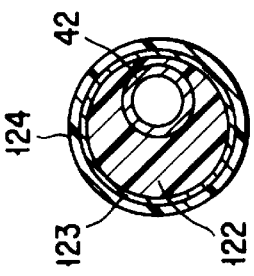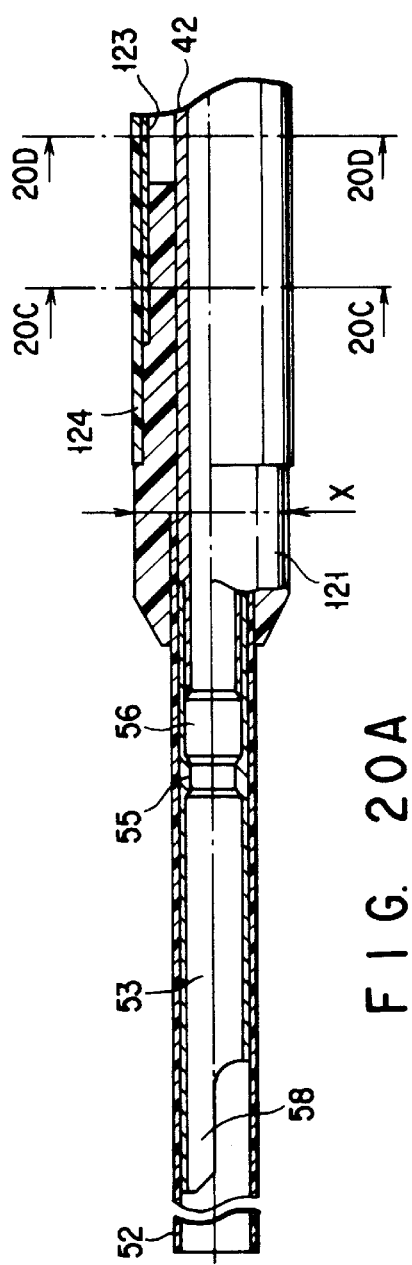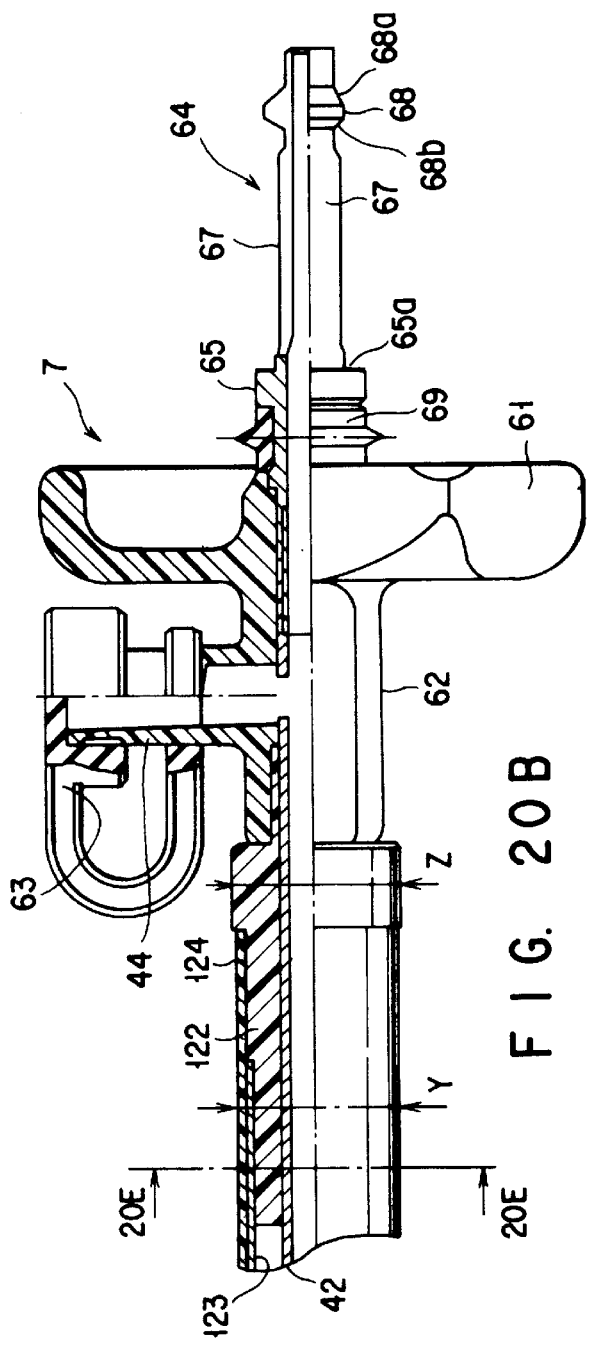

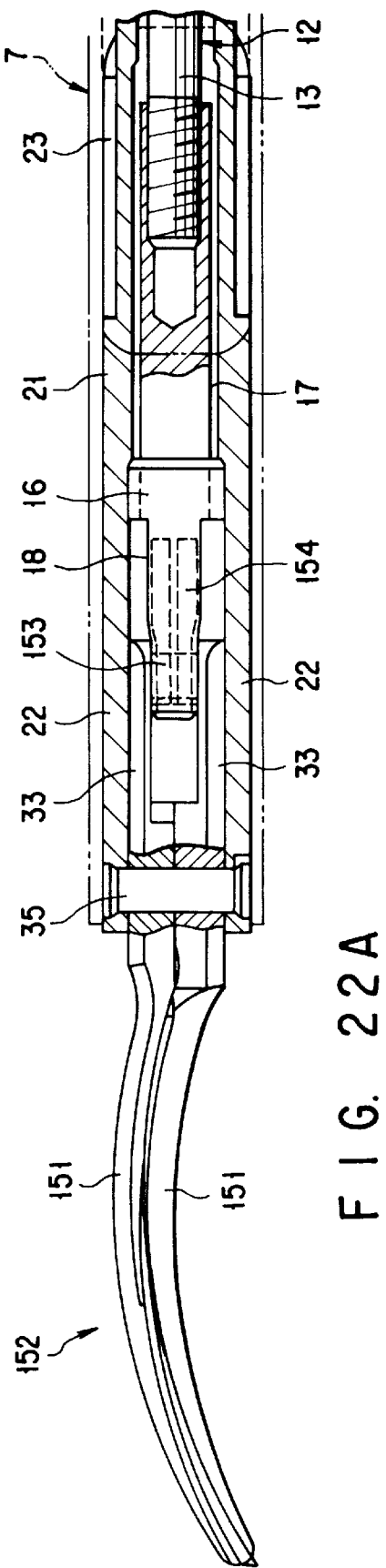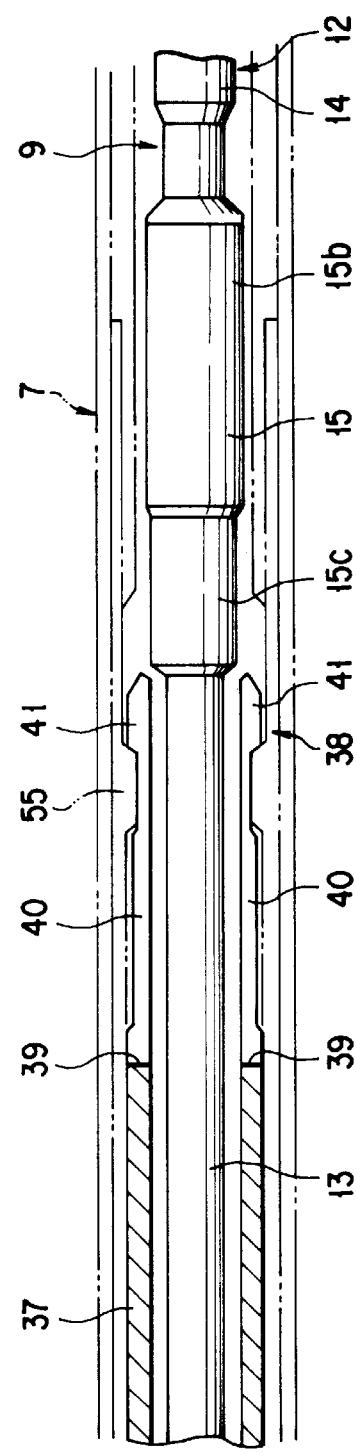
FIG. 22A
FIG. 22B

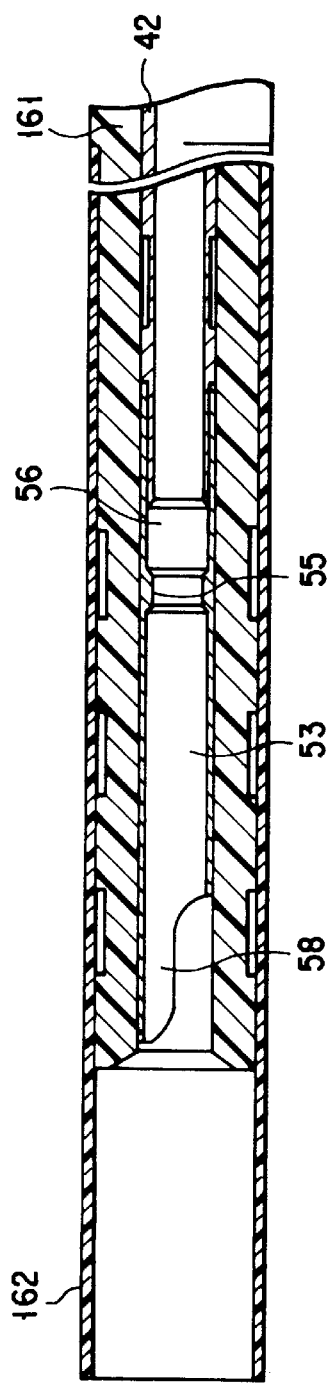
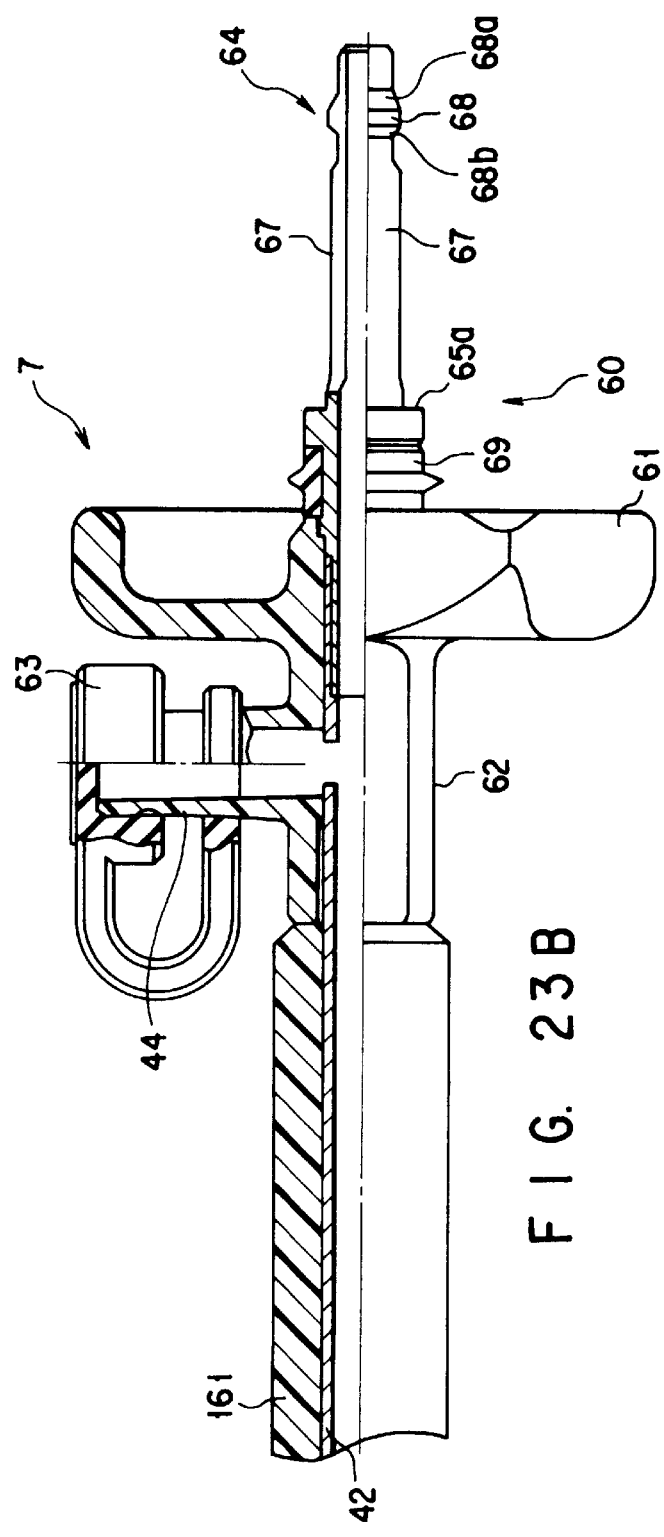
F I G. 23A
F I G. 23B

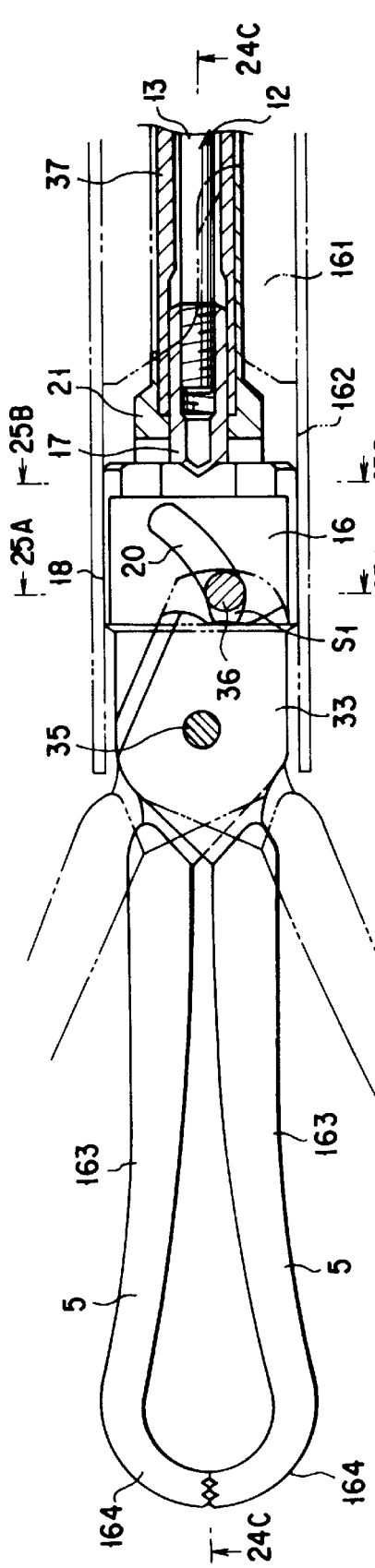
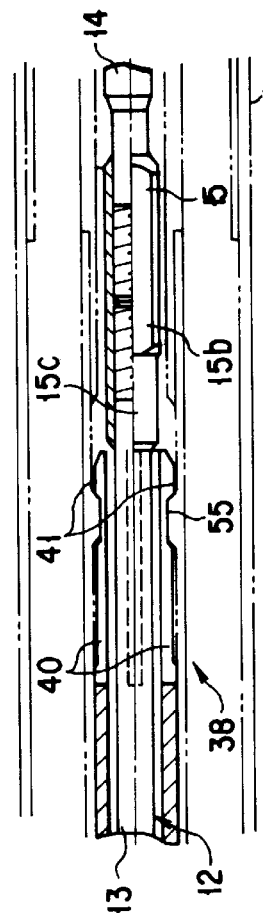
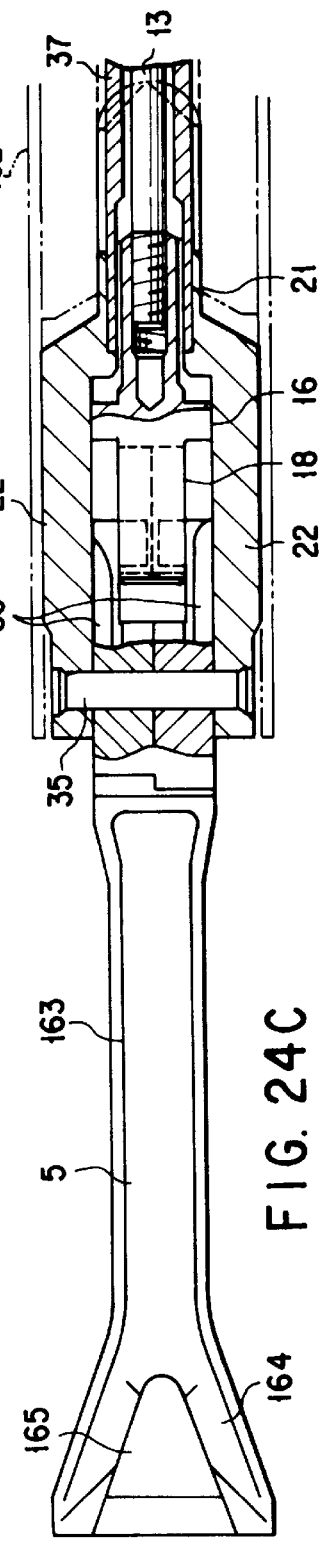
FIG. 24A
FIG. 24B
FIG. 24C

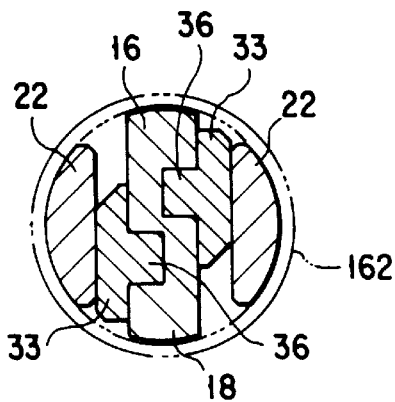
F I G. 25A
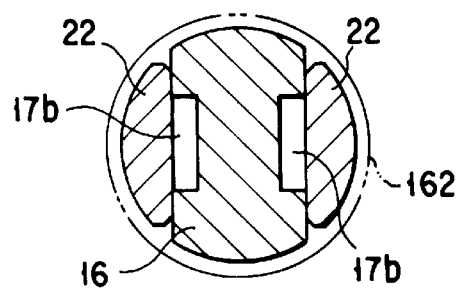
F I G. 25B
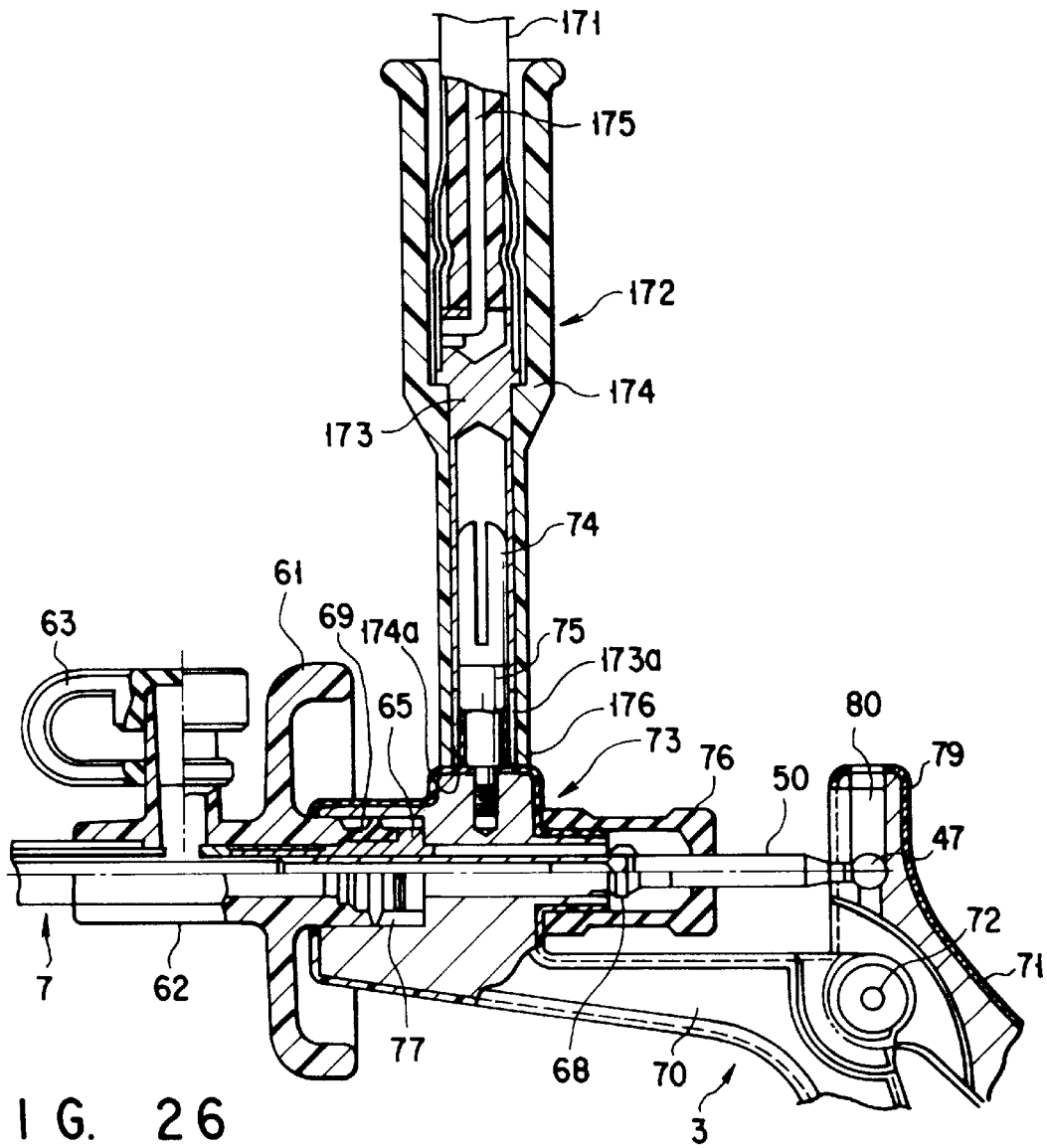
F I G. 26

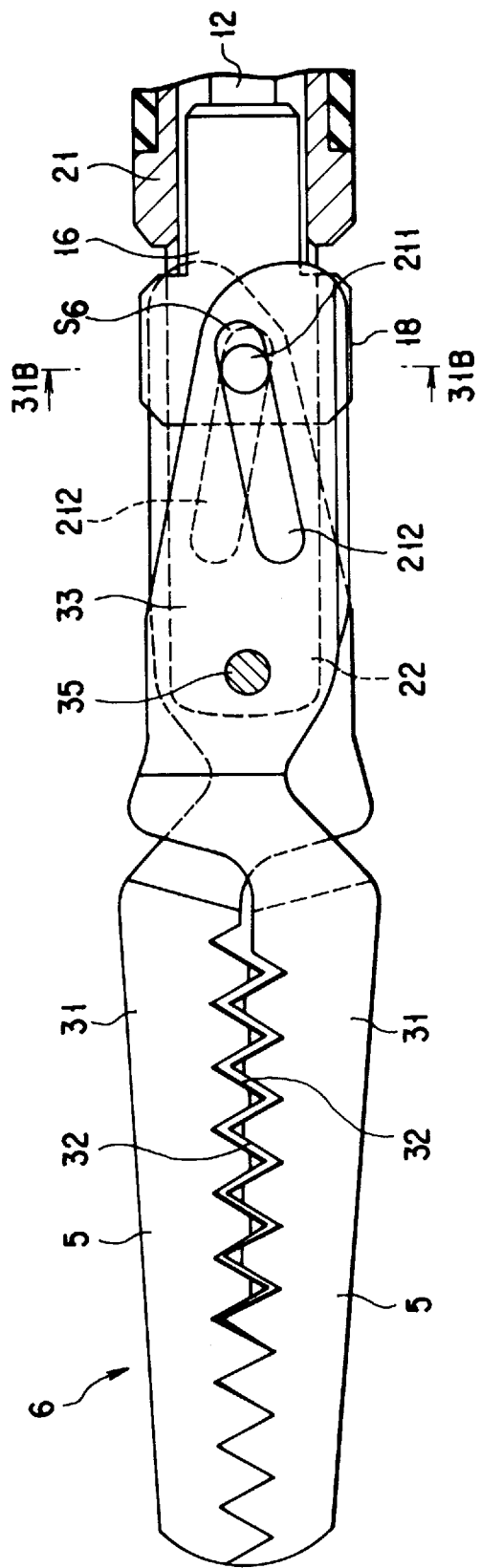
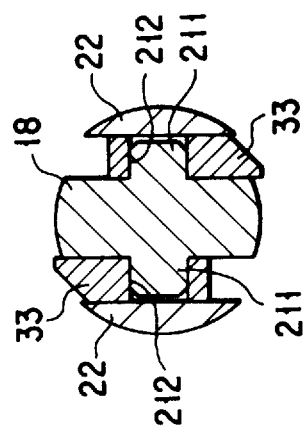
F I G. 31A
F I G. 31B

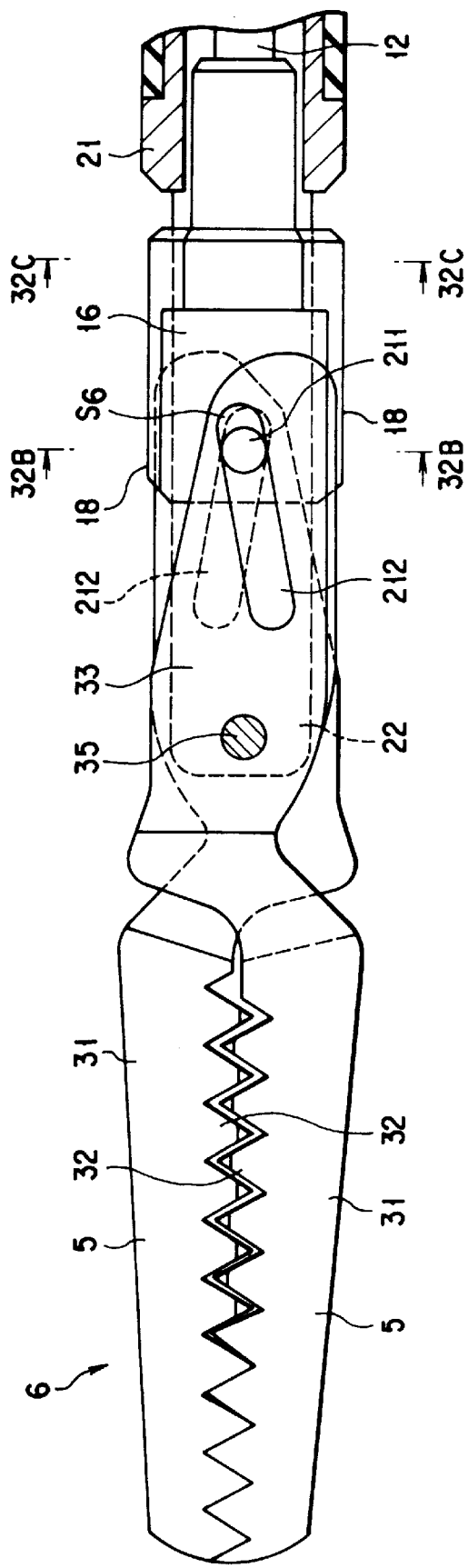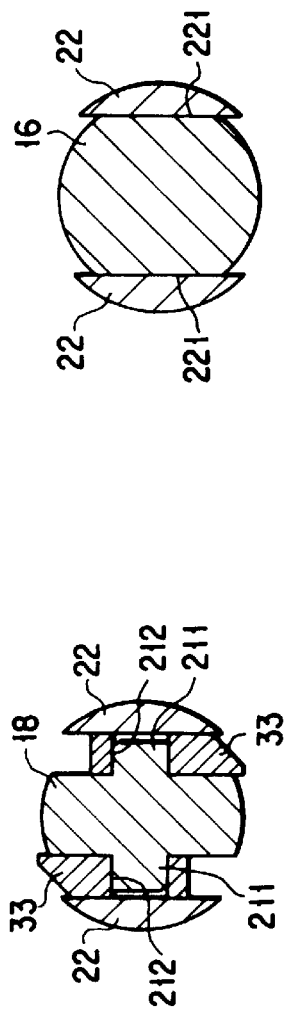
FIG. 32A FIG. 32B FIG. 32C

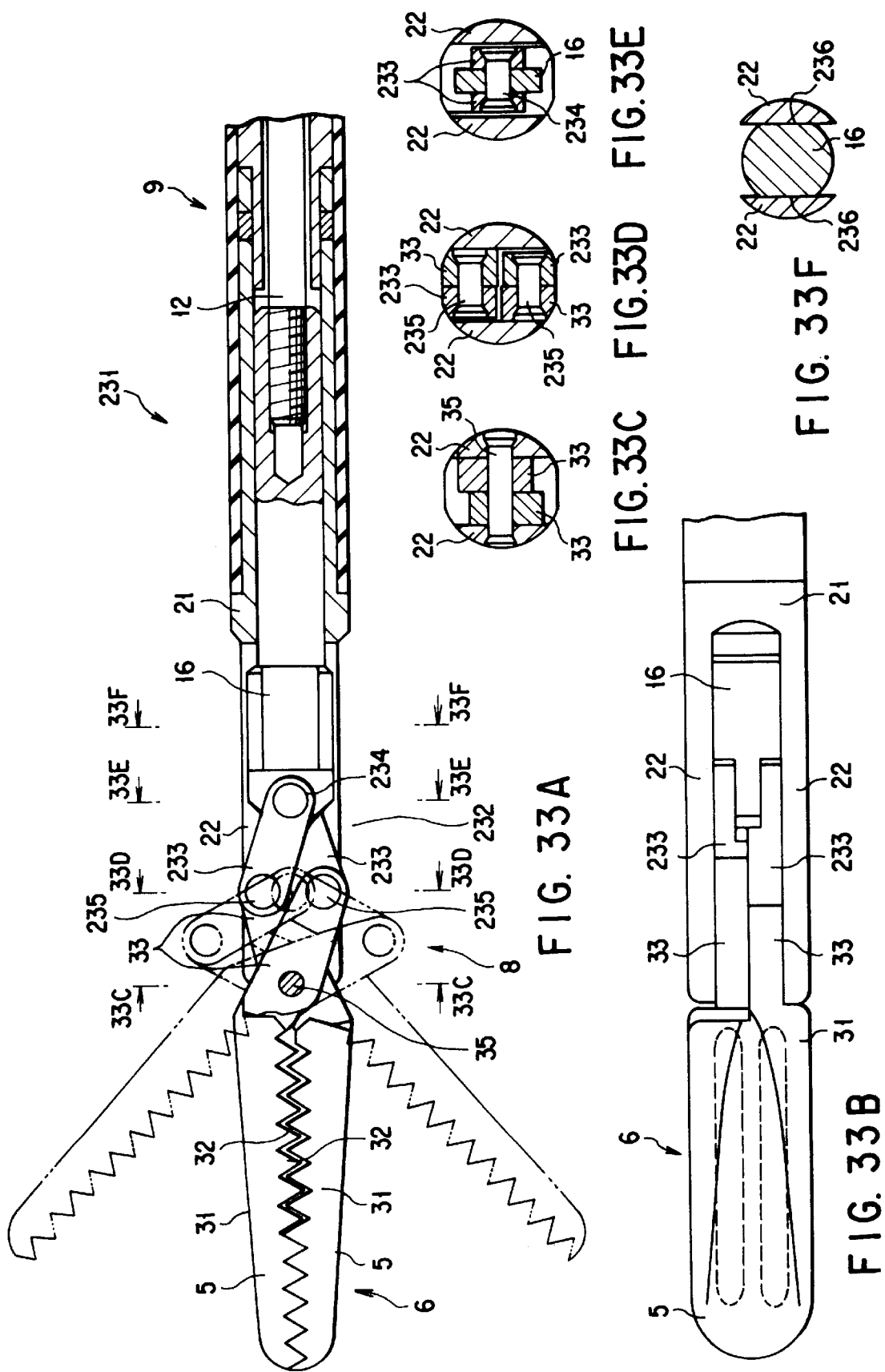

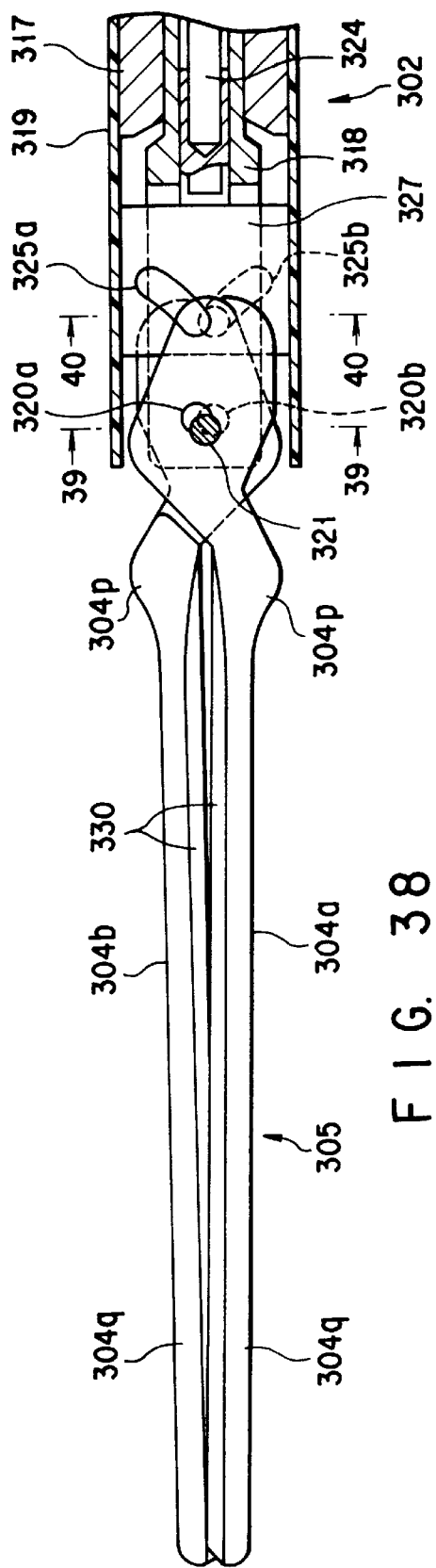
FIG. 38
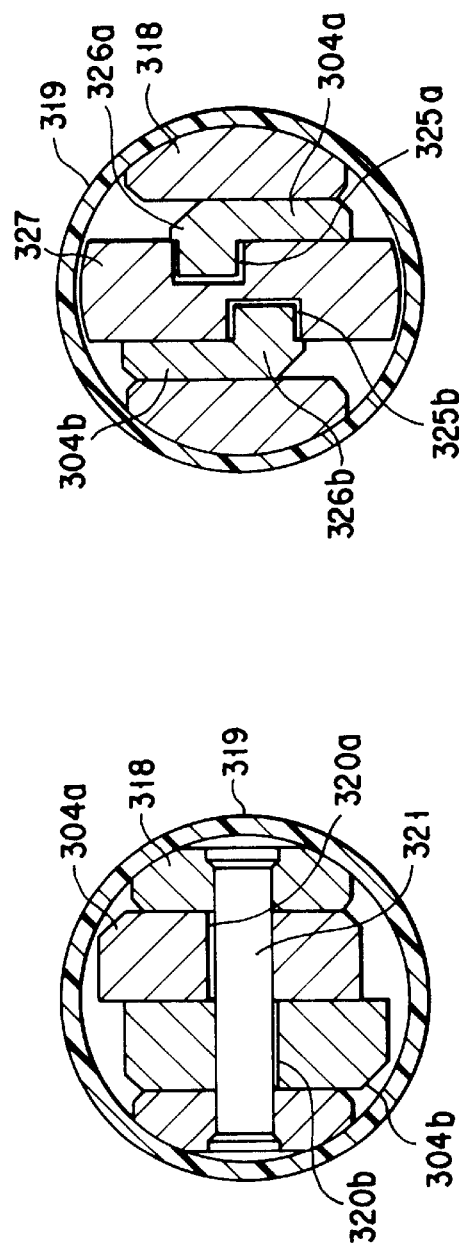
FIG. 40
FIG. 39

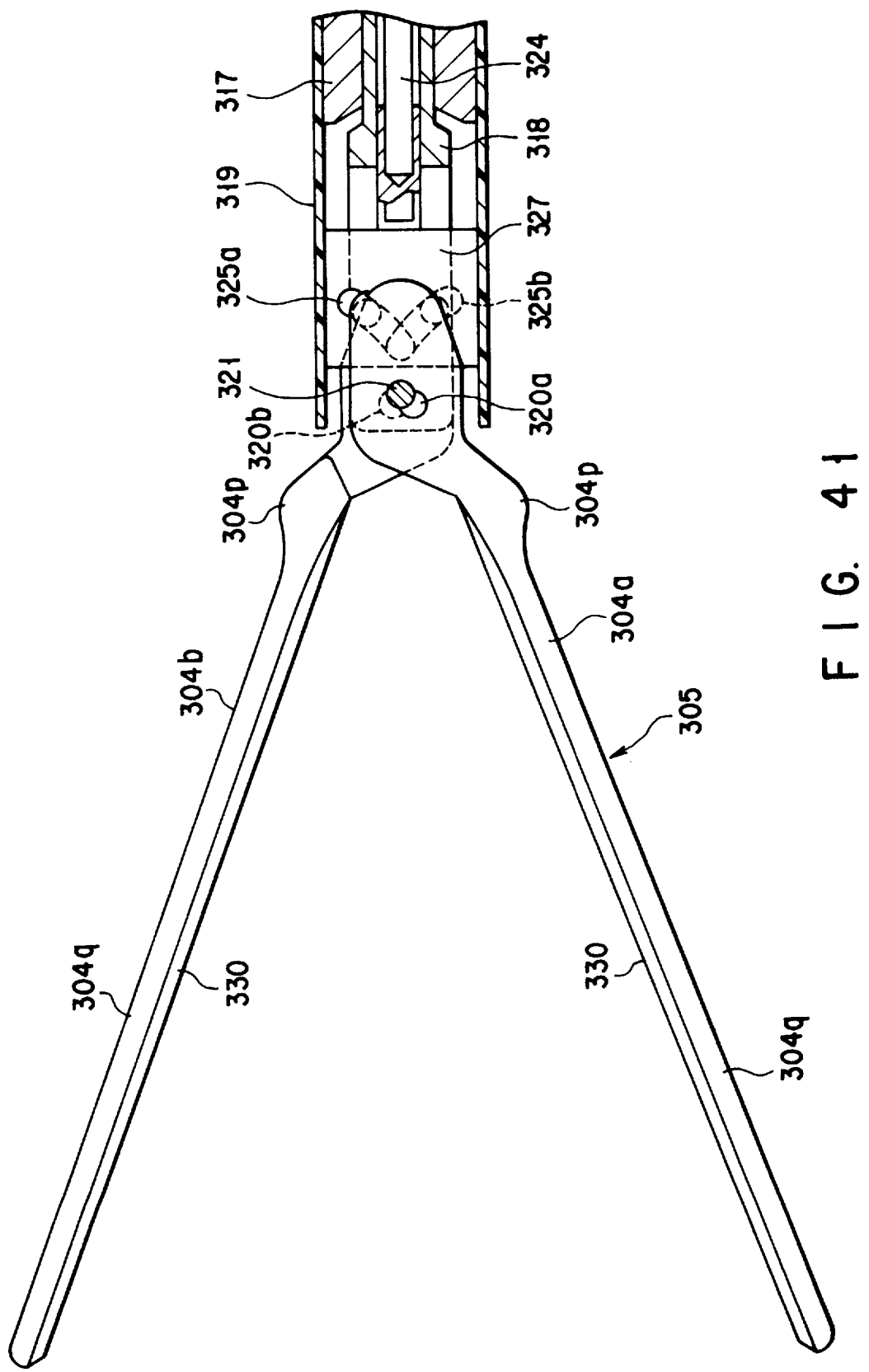
F I G. 41

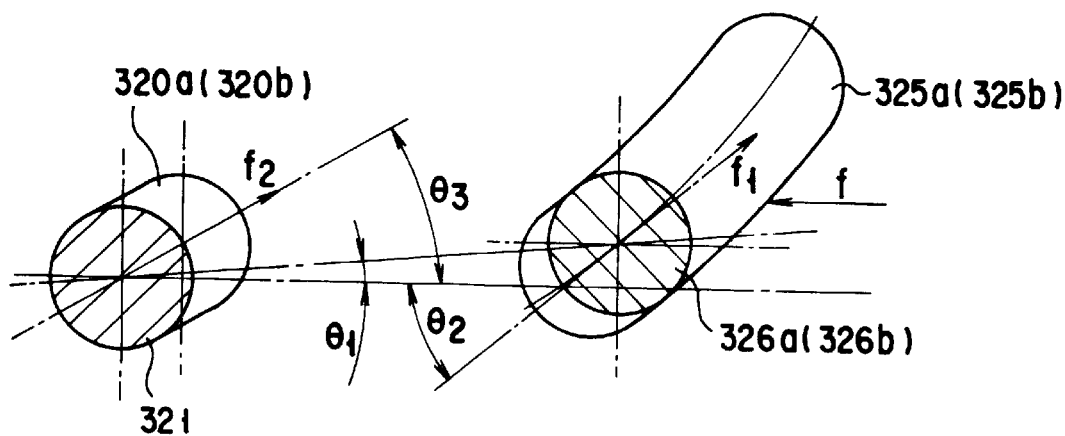
F I G. 42
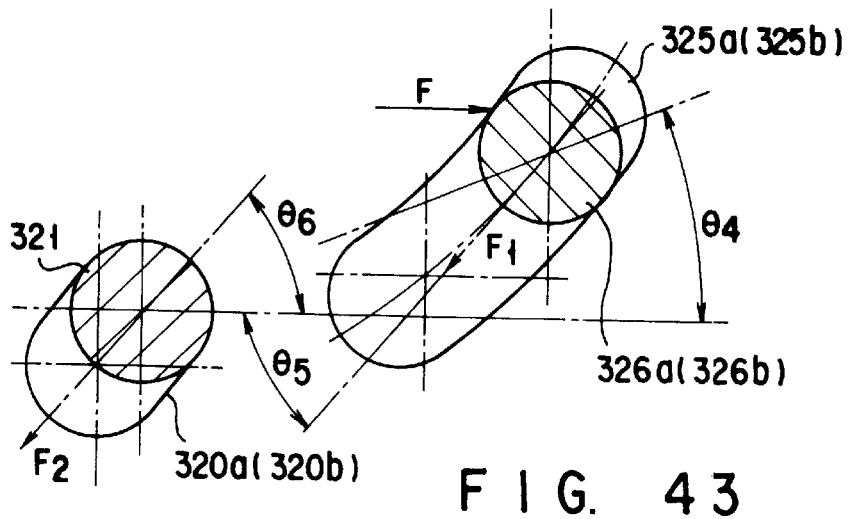
F I G. 43
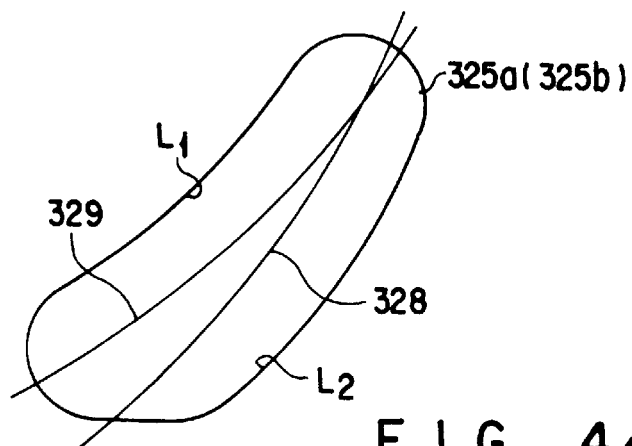
F I G. 44

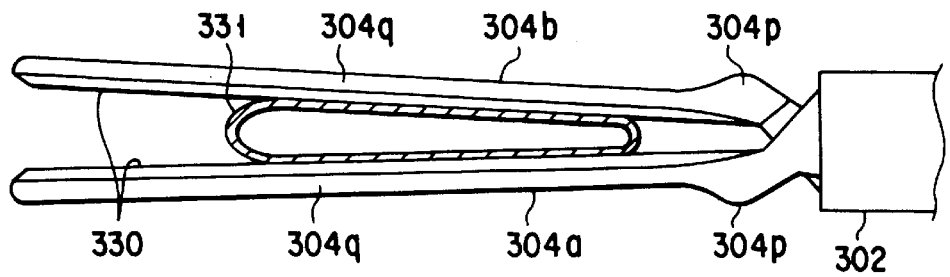
F I G. 45
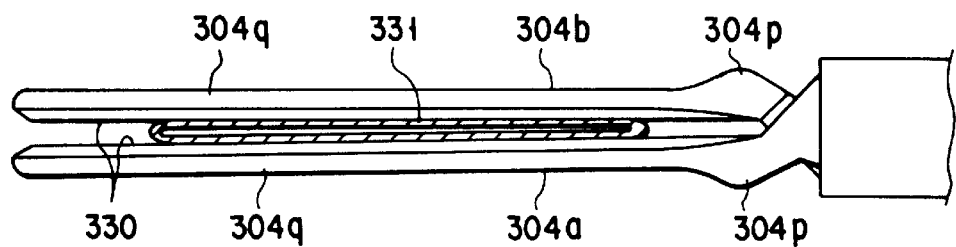
F I G. 46
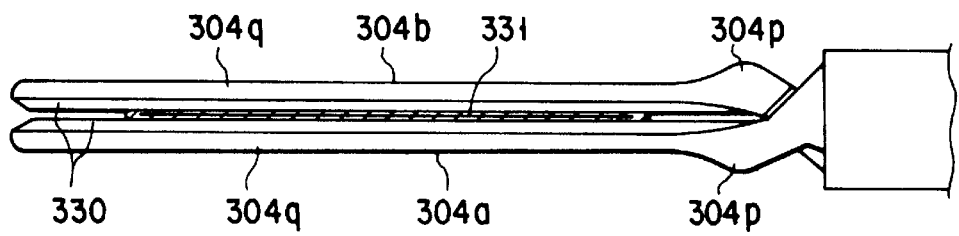
F I G. 47
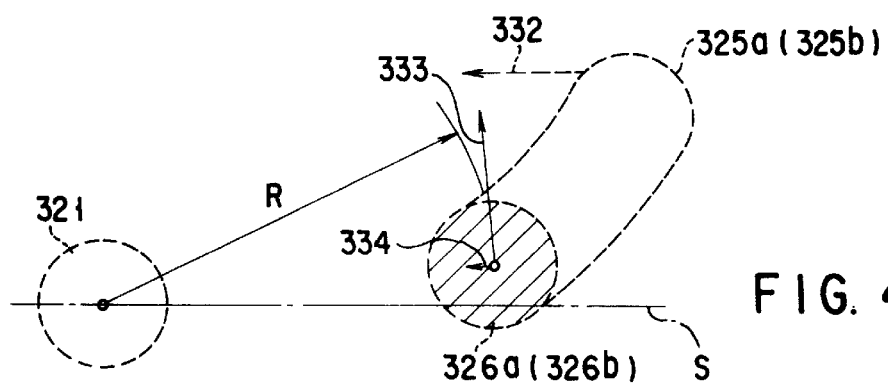
F I G. 48

MEDICAL INSTRUMENT FOR USE IN COMBINATION WITH ENDOSCOPES

This application is a Continuation, of application Ser. No. 08/498,170, filed Jul. 5, 1995 now abandoned.

BACKGROUND OF THE INVENTION

1. Field of the Invention

The present invention relates to a medical instrument for use in combination with endoscopes, to examine a body cavity or to perform treatment or surgery within a body cavity.

2. Description of the Related Art

Generally, forceps, which are a type of medical instrument, comprise an insertion section and a pair of tongs. The insertion section is to be inserted into a body cavity. The tongs are rotatably coupled to the distal end of the insertion section and can open and close. Most forceps have a link mechanism for opening and closing the tongs, as is disclosed in Jpn. Pat. Appln. KOKAI Publication No. 5-285147.

The forceps generally further comprise an operation section which is connected to the proximal end of the insertion section. The insertion section comprises a hollow cylindrical sheath and an operating shaft. The operating shaft is inserted in the sheath and can move back and forth along the axis thereof. Coupled to the distal end of the shaft is the link mechanism. The operating shaft has its proximal end fastened to a movable member, which is a component of the operation section. To open or close the tongs, an operator moves the movable member of the operation section. Fastened to the movable member, the operating shaft moves back and forth along its axis. The link mechanism is thereby driven, either opening or closing the tongs.

Comprising many components, the link mechanism has a complex structure. Recently it has often been replaced by a cam mechanism as means for opening and closing the tongs. The cam mechanism has a small number of parts and, hence, a simple structure, as is disclosed in German Utility Model Publications G91 06 506.2 and G89 00 376.4.

The cam mechanism has a cam groove and a cam pin. The pin can move along the cam groove. To open or close the tongs, the operator moves the movable member of the operation section, thereby driving the cam mechanism. The cam mechanism, thus driven, opens or closes the tongs.

With a forceps having a cam mechanism used as means for opening and closing the tongs, the operator moves the movable member of the operation section, pulling the operating shaft in order to close the tongs. As the shaft is pulled, the cam pin moves along the cam groove, thereby closing the tongs. When the pin abuts on the end of the cam groove, the tongs are closed completely.

Once the cam pin abuts on the end of the cam groove, a force is no longer applied to the tongs to close them. Even if the operator exerts a great force on the movable member thereafter, this force will not be transmitted to the distal end of either tong.

Here arises a problem in the case where the tongs need to clamp a thin tissue membrane such as the mesentery in order to peel it off. Since the force exerted to the movable member to close the tongs cannot be transmitted to the distal ends of the tongs after the tongs have been closed fully, the tongs cannot sufficently clamp the thin tissue membrane with a force great enough to keep holding the membrane. As a consequence, the thin tissue membrane may slip out of the nip between the tongs as it is pulled. It may therefore be difficult for a surgeon to peel off the membrane successfully.

SUMMARY OF THE INVENTION

In view of the foregoing, the present invention has been made. Its object is to provide a medical instrument for use in combination with endoscopes, which can clamp a thin tissue membrane or the like firmly enough so that the membrane or the like does not slip as it is peeled off, and which can therefore help to peel off a thin tissue membrane or the like successfully.

To attain the object, a medical instrument according to the present invention comprises an insertion section to be inserted into a body cavity; a pair of treating members connected to the distal end of the insertion section and capable of opening and closing; an operation section connected to the proximal end of the insertion section, an operating shaft extending through the insertion section and capable of moving back and forth as the operation section is operated; and drive means for opening and closing the treating members when the shaft is moved back and forth. The medical instrument is characterized in that the drive means apply an additional force to the treating members even after the treating members have closed completely.

More precisely, the drive means has a cam groove and a cam pin. The pin can move along the cam groove to open and close the treating members. The groove is longer than is necessary to guide the pin to move the treating members to the closed position. Hence, even after the treating members have been closed, the cam pin can move along the pin groove and can transmit a force to the treating member reliably. As a result, the treating member can firmly and steadily hold a thin tissue membrane or the like in a body cavity. This prevents the membrane from slipping out of the nip between the treating members as the membrane is peeled off and thus ensures a successful peeling of the thin tissue membrane.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

FIG. 2A is a plan view showing the drive unit incorporated in the first embodiment;

FIG. 2B is a side view of the drive unit;

FIG. 3A is a cutaway plan view of the drive unit;

FIG. 3B is a cutaway side view of the drive unit;

FIG. 4A is a sectional view taken along line 4A—4A shown in FIG. 3B;

FIG. 4B is a sectional view taken along line 4B—4B shown in FIG. 3B;

FIG. 4C is a sectional view taken along line 4C—4C shown in FIG. 3B;

FIG. 4D is a sectional view taken along line 4D—4D shown in FIG. 3B;

FIG. 4E is a sectional view taken along line 4E—4E shown in FIG. 3B;

FIG. 4F is a sectional view taken along line 4F—4F shown in FIG. 3B;

FIG. 5A is a cutaway plan view illustrating the distal end portion of the drive unit;

FIG. 5B is a cutaway side view showing the distal end portion of the drive unit;

FIG. 5C is a longitudinal sectional view showing a snap-fit arm provided at an end of the drive unit;

FIG. 6A is a sectional view taken along line 6A—6A shown in FIG. 5B;

FIG. 6B is a cross-sectional view of the guide pin holding the link arm incorporated in the first embodiment;

FIG. 7A is a longitudinal sectional view showing the sheath unit of the first embodiment;

FIG. 7B is a cutaway side view showing the rear end portion of the sheath unit;

FIG. 8A is a longitudinal sectional view of the sheath unit, illustrating the position which the distal end of the connecting pipe takes;

FIG. 8B is a sectional view taken along line 8B—8B shown in FIG. 8A;

FIG. 8C is a longitudinal sectional view explaining how the connecting pipe and the inner pipe are coupled together;

FIG. 8D is a cutaway side view illustrating a snap-fit arm provided a the rear end of the sheath unit;

FIG. 8E is a sectional view taken along line 8E—8E shown in FIG. 8D;

FIG. 8F is a longitudinal sectional view showing the inner projection of the sheath unit;

FIG. 12A is a longitudinal sectional view of the first embodiment, showing the movable handle rotated, fitting the projecting portion of the drive unit in the projecting portion of the sheath unit;

FIG. 12B is a longitudinal sectional view of the first embodiment, illustrating the operation section assuming the state shown in FIG. 12A;

FIG. 13A is a longitudinal sectional view of the first embodiment, showing the projections extending beyond the annular projection into the recess made in the connecting pipe;

FIG. 13B is a longitudinal sectional view of the first embodiment, showing the operation section taking the state shown in FIG. 13A;

FIG. 15A is a longitudinal sectional view of the first embodiment, with the tongs opened;

FIG. 15B is a longitudinal sectional view of the first embodiment, explaining how the drive unit and the sheath unit are connected together when the embodiment takes the state shown in FIG. 15A;

FIG. 16A is a longitudinal sectional view showing the distal end portion of a forceps according to a second embodiment of the present invention;

FIG. 16B is a longitudinal sectional view of the second embodiment, explaining how the drive unit and the sheath unit are connected together;

FIG. 16C is a sectional view taken along line 16C—16C shown in FIG. 16B;

FIG. 16D is a sectional view taken along line 16D—16D shown in FIG. 16B;

FIG. 17A is a longitudinal sectional view showing the distal end portion of a forceps according to a third embodiment of the invention;

FIG. 17B is a longitudinal sectional view of the third embodiment, explaining how the drive unit and the sheath unit are connected together;

FIG. 17C is a sectional view taken along line 17C—17C shown in FIG. 17A;

FIG. 17D is a sectional view taken along line 17D—17D shown in FIG. 17A;

FIG. 17E is a sectional view taken along line 17E—17E shown in FIG. 17A;

FIG. 17F is a sectional view taken along line 17F—17F shown in FIG. 17A;

FIG. 17G is a sectional view taken along line 17G—17G shown in FIG. 17B;

FIG. 18A is a plan view showing one of the tongs a forceps according to a fourth embodiment of the invention;

FIG. 18B is a side view of the tong;

FIG. 18C is a sectional view of the tong;

FIG. 18D is a plan view illustrating a modified tong for use in the fourth embodiment;

FIG. 20A is a cutaway side view of a modified sheath unit for use in the fourth embodiment;

FIG. 20B is a cutaway side view of the proximal end portion of the sheath unit;

FIG. 20C is a sectional view taken along line 20C—20C shown in FIG. 20A;

FIG. 20D is a sectional view taken along line 20D—20D shown in FIG. 20A;

FIG. 20E is a sectional view taken along line 20E—20E shown in FIG. 20B;

FIG. 22A is a cross-sectional view of a third modified instrument section for use in the first embodiment;

FIG. 22B is a plan view showing the snap-fit portion of the third modified instrument section;

FIG. 23A is a cutaway side view illustrating the distal end portion of the sheath unit incorporated in a forceps according to a modified embodiment of the present invention;

FIG. 23B is a cutaway side view showing the proximal end portion of the sheath unit;

FIG. 24A is a cutaway side view of the distal end portion of the drive unit incorporated in the modified embodiment;

FIG. 24B is a longitudinal sectional view of the snap-fit portion of the drive unit;

FIG. 24C is a sectional view taken along line 24C—24C shown in FIG. 24A;

FIG. 25A is a sectional view taken along line 25A—25A shown in FIG. 24A;

FIG. 25B is a sectional view taken along line 25B—25B shown in FIG. 24A;

FIG. 26 is a longitudinal sectional view of the first embodiment, showing an A-cord cap connected to the electron pin;

FIG. 31A is a side view showing the distal end portion of a forceps according to an eighth embodiment of the present invention;

FIG. 31B is a sectional view taken along line 31B—31B shown in FIG. 31A;

FIG. 32A is a side view showing the distal end portion of a forceps according to a ninth embodiment of the invention;

FIG. 32B is a sectional view taken along line 32B—32B shown in FIG. 32A;

FIG. 32C is a sectional view taken along line 32C—32C shown in FIG. 32A;

FIG. 33A is a side view of the distal end portion of a forceps according to a tenth embodiment of the present invention;

FIG. 33B is a plan view of the tenth embodiment;

FIG. 33C is a sectional view taken along line 33C—33C shown in FIG. 33A;

FIG. 33D is a sectional view taken along line 33D—33D shown in FIG. 33A;

FIG. 33E is a sectional view taken along line 33E—33E shown in FIG. 33A;

FIG. 33F is a sectional view taken along line 33F—33F shown in FIG. 33A;

FIG. 38 is a cutaway side view of the distal end portion of the eleventh embodiment;

FIG. 39 is a sectional view taken along line 39—39 shown in FIG. 38;

FIG. 40 is a sectional view taken along line 40—40 shown in FIG. 38;

FIG. 41 is a cutaway side view of the distal end portion of the eleventh embodiment, illustrating the tongs assuming open position;

FIG. 42 is a diagram explaining the cam mechanism incorporated in the eleventh embodiment;

FIG. 43 is another diagram explaining the cam mechanism incorporated in the eleventh embodiment;

FIG. 44 is a diagram showing the shape of the cam groove provided in the eleventh embodiment;

FIG. 45 is a side view of the distal end portion of the eleventh embodiment, explaining how the tongs are closed;

FIG. 46 is another side view of the distal end portion of the eleventh embodiment, explaining how the tongs are closed;

FIG. 47 is still another side view of the distal end portion of the eleventh embodiment, explaining how the tongs are closed;

FIG. 48 is a diagram explaining how the drive unit of the eleventh embodiment operates;

DETAILED DESCRIPTION OF THE PREFERRED EMBODIMENTS

A forceps 1 for use in combination with an endoscope, which is the first embodiment of the present invention, will be described with reference to FIGS. 1 to 15*b*.

Figure 1:
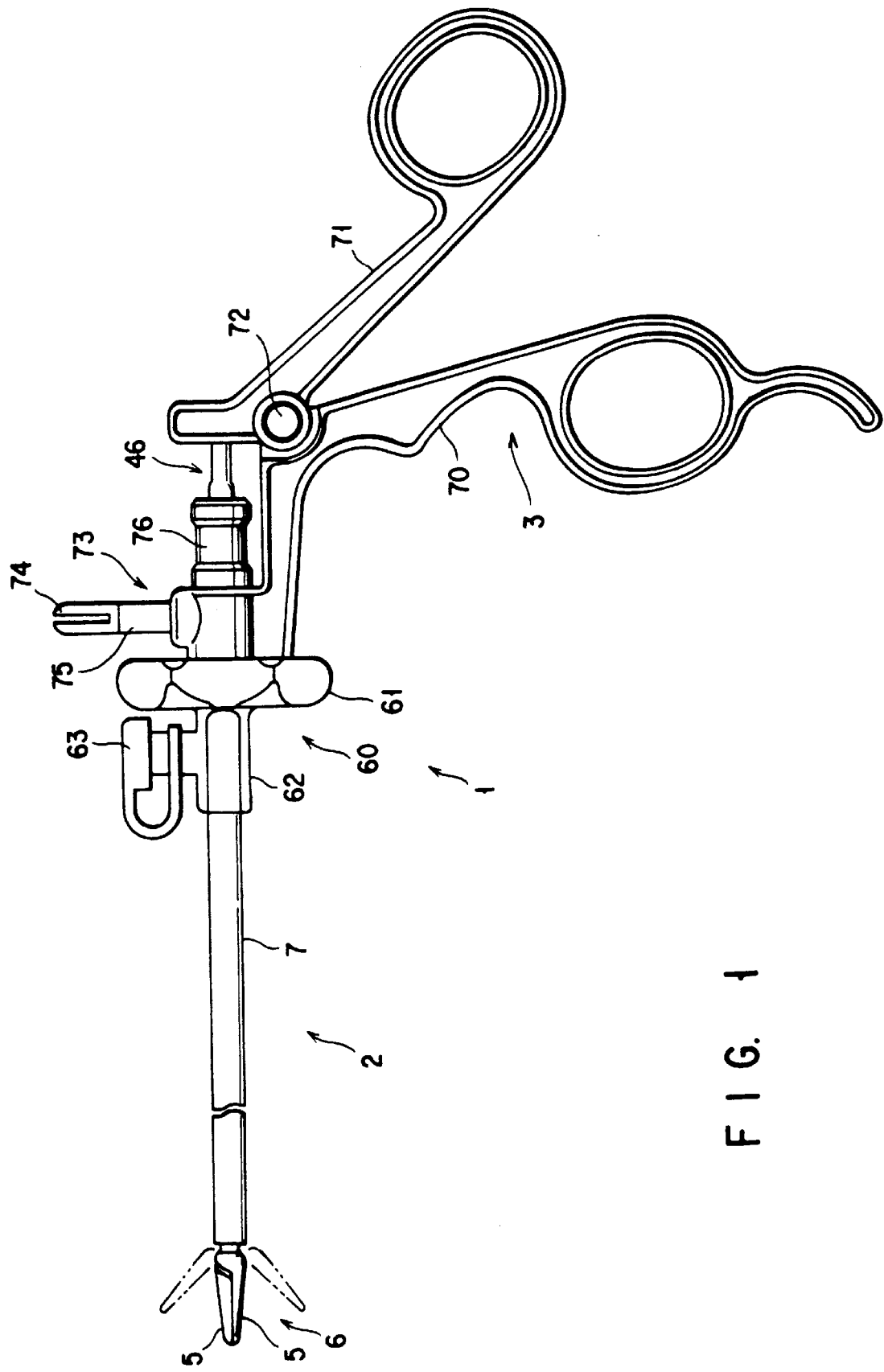
FIG. 1 is a side view of a forceps according to a first embodiment of the present invention.

As shown in FIG. 1, the forceps 1 comprises an insertion section 2 and an operation section 3. The section 2 is designed to be inserted into a body cavity, passing through a trocar tube (not shown). The operation section 3 is coupled to the proximal end of the insertion section 2.

The insertion section 2 comprises a shaft portion covered by a hollow cylindrical sheath unit 7, and an instrument section 6 having a pair of tongs 5 connected to the distal end of the shaft portion. The tongs 5 are made of, for example, stainless steel (SUS420J2). The tongs 5 are coated with one or more layers of ceramic compound such as titanium nitride (TiN) or titanium carbide (TiC), formed by means of, for example, chemical vapor deposition (CVD). They therefore have a wear-resistant surface.

A drive unit 9 shown in FIG. 2A and 2B is provided in the sheath unit 7. The drive unit 9 incorporates a drive mechanism 8 for opening and closing the tongs 5.

Figure 9A:
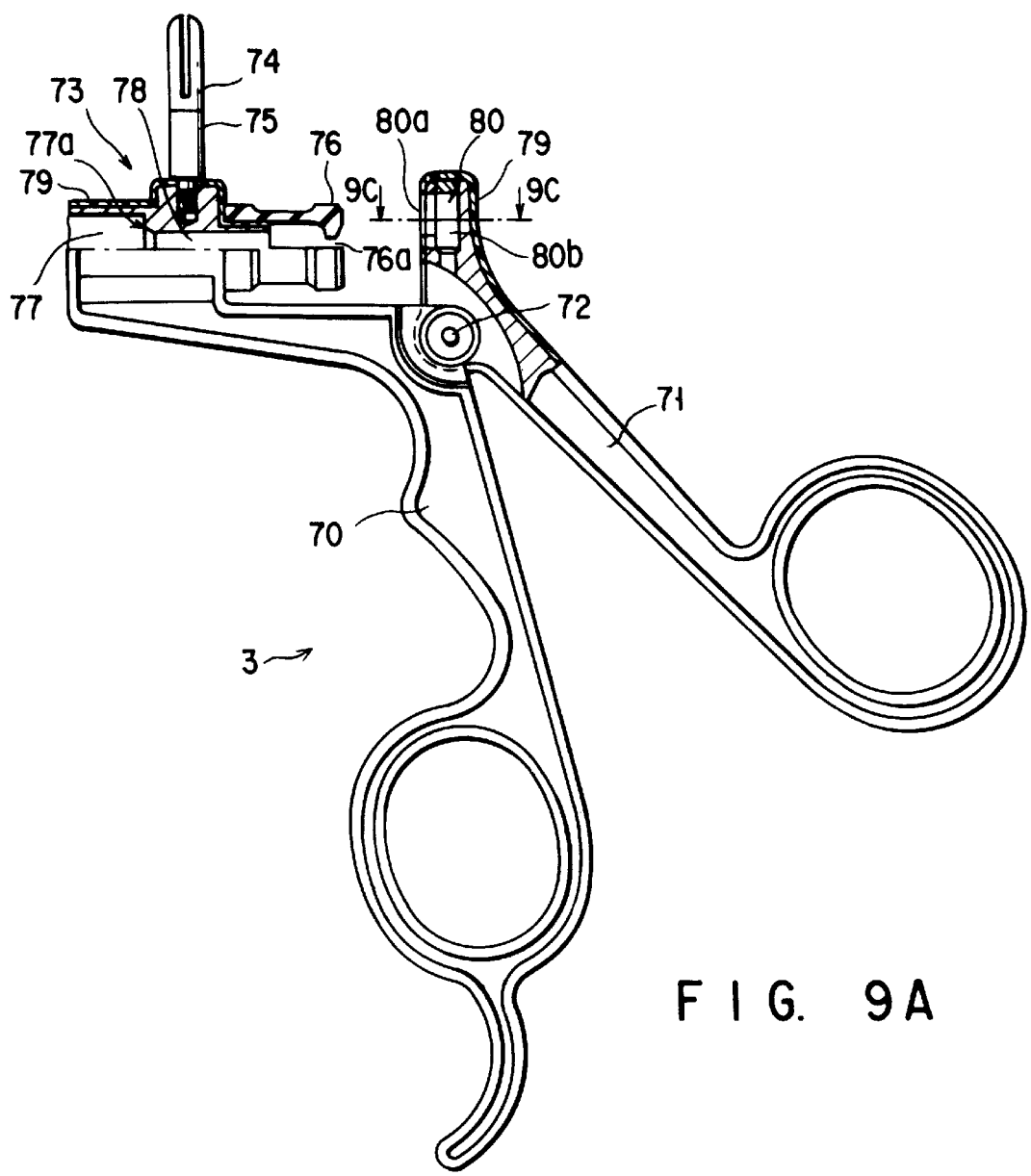
FIG. 9A is a partly sectional side view showing the operation section of the first embodiment.
Figure 10:
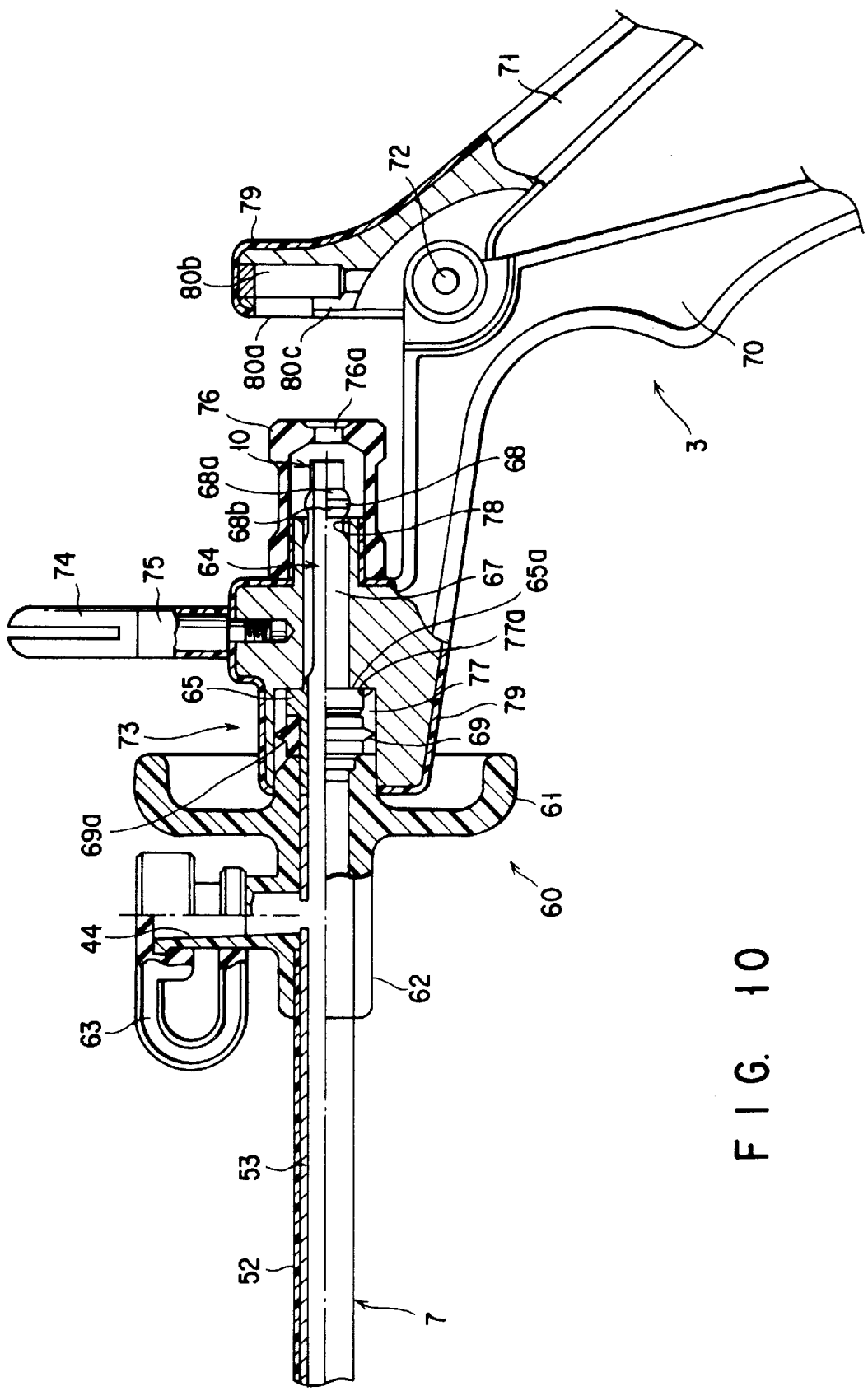
FIG. 10 is a longitudinal sectional view of the first embodiment, illustrating the sheath unit connected to the connecting portion of the fixed handle of the operation section.
Figures 14A, 14B:
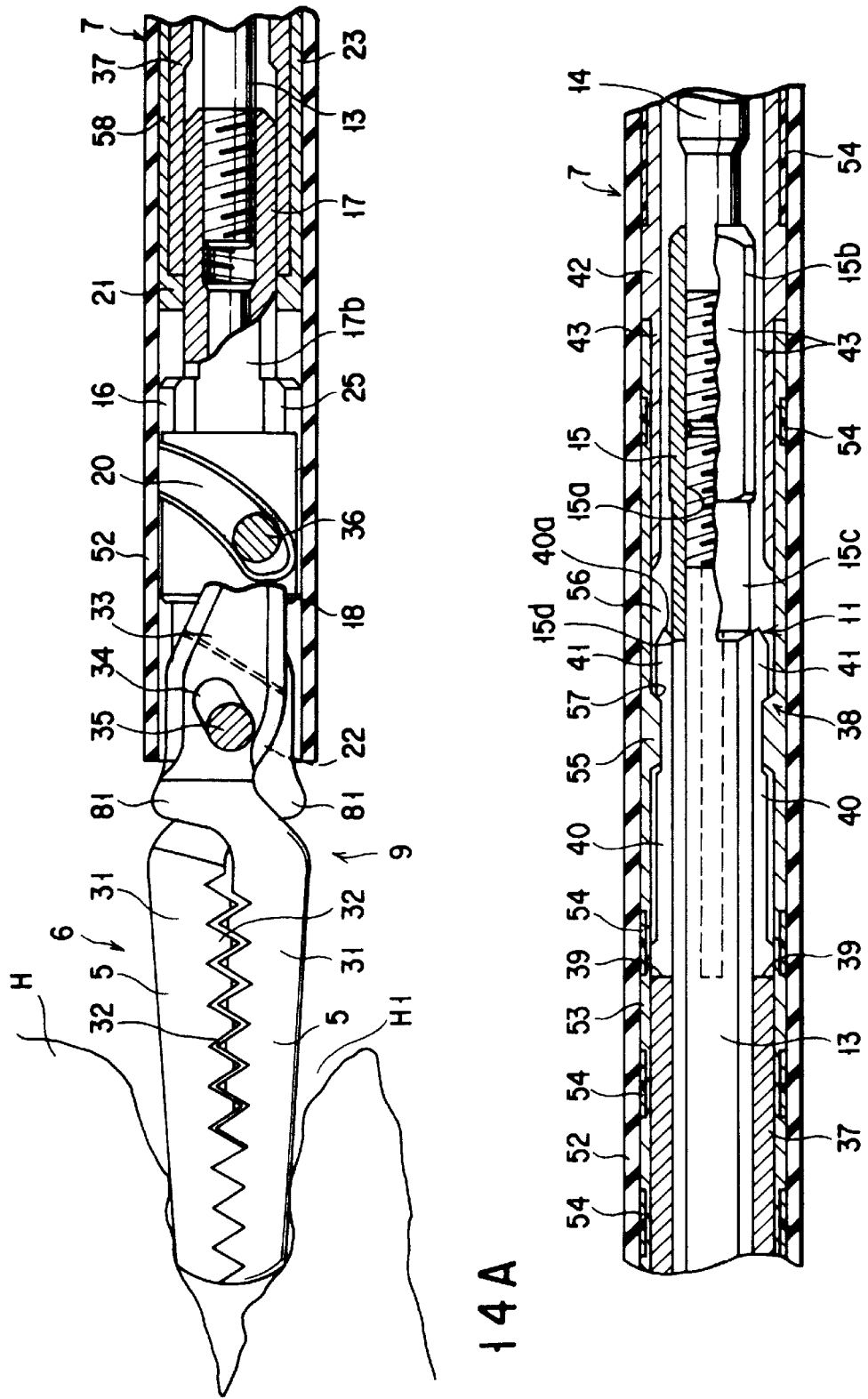
FIG. 14A is a longitudinal sectional view of the first embodiment inserted into a gap between living tissues, with the tongs closed completely.
FIG. 14B is a longitudinal sectional view of the first embodiment, explaining how the drive unit and the sheath unit are connected together when the embodiment assumes the state shown in FIG. 14A.

The forceps 1 comprises three units independently manufactured, i.e., the operation section 3 (FIG. 9A), the sheath unit 7 (FIGS. 7A and 7B), and the drive unit 9 (FIGS. 2A and 2B). The operation section 3 and the sheath unit 7 are removably connected by a first connecting section 10 (FIG. 10). The sheath unit 7 and the drive unit 9 are removably connected by a second connecting section 11 (FIG. 14B).

The drive mechanism 8 has an operating shaft 12. This shaft 12 can move back and forth in the sheath unit 7 to open and close the tongs 5. As shown in FIGS. 3A and 3B, the operating shaft 12 is comprised of a distal shaft 13, a proximal shaft 14 and connecting rod 15. The connecting rod 15 is a hollow cylinder and connecting the distal shaft 13 and the proximal shaft 14.

As illustrated in FIG. 5C, the connecting rod 15 has an axial screw hole 15a. The distal shaft 13 has a male screw 13a on its proximal end portion. The proximal shaft 14 has a male screw 14a on its distal end portion. The male screws 13a and 14a are set in screw engagement with the screw hole 15a, whereby the connecting rod connects the distal shaft 13 and the proximal shaft 14, constituting the operating shaft 12.

As seen from FIGS. 5A and 5B, a cam member 16 is fastened to the distal end of the shaft 13. The cam member 16 has a hollow cylindrical coupling 17 on its rear end portion. The coupling 17 has a female screw 17a in its inner circumferential surface. Set in engagement with the female screw 17a is the male screw 13b of the distal shaft 13. As shown in FIGS. 3A and 4C, the coupling 17 has two water-supplying grooves 17b cut in the outer surface and extending over the entire length in parallel to the axis of the coupling 17.

A tong-connecting member 18 shaped like a rectangular block is fastened to the distal end of the cam member 16. As shown in FIG. 5B, an arcuate groove 20 (cam groove) is made in either side of the tong-connecting member 18.

A holding member 21 is mounted on the cam member 16, for guiding the operating shaft 12 in the axial direction. Two support arms 22 protrude from the distal end of the holding member 21. A positioning projection 23 protrudes from the rear end of the cover 21. The projection 23 is a half of a hollow cylinder, as can be seen from FIG. 4D. The projection 23 has a cutout 24 in the proximal edge as shown in FIG. 2A. The cutout 24 has a corner of about 90° C.

As shown in FIG. 4C, that part of the cam member 16 which lies between the coupling 17 and the tong-connecting member 18 has two flat surfaces 25 which contact the support arms 22 of the holding member 21, respectively. The distance between the flat surfaces 25 is equal to the distance between the support arms 22. The support arms 22 contacting the flat surfaces 25 collectively serve as a stopper 26, which prevents the cam member 16 from rotating around its axis.

Each tong 5 of the instrument section 6 has a holding member 31. The holding member 31 has teeth 32 on the inner side which is to abut on the other tong 5. On the outer side of the holding member 31 there may be engraved the name of the instrument section 6 and the manufacturer thereof by means of laser marking or the like.

A link arm 33 protrudes from the proximal end of each tong 5. The link arm 33 has an elongated hole 34 in the middle portion as illustrated in FIG. 5B. As shown in FIG. 5A, a fulcrum pin 35 is provided, passing through the pin-guiding holes 22a made in the distal end portions of the support arms 22 and also through the elongated holes 34 of both link arms 33. The fulcrum pin 35 is fastened at the ends to the support arms 22. Both tongs 5 of the instrument section 6 are thereby supported rotatably by the support arms 22 of the holding member 21.

A guide pin (cam pin) 36 projects from the distal end of each link arm 33 and inserted slidably in the arcuate groove 20 cut in one side of the tong-connecting member 18 which is, as described above, fastened to the distal end of the cam member 16. The arcuate grooves 20 made in the sides of the member 18 and the guide pins 36 of the tongs 5 constitute a cam mechanism K.

The cam mechanism K is driven when the operating shaft 12 is moved along its axis, toward and away from the holding member 21, in order to actuate the drive mechanism 8 incorporated in the drive unit 9. To be more specific, when the cam member 16 moves in the axial direction together with the operating shaft 12, the guide pins 36 of the cam mechanism K move along the arcuate grooves 20. As the guide pins 36 move, the link arms 33 of the tongs 5 rotate around the fulcrum pin 35. As a result, both holding members 31 of the instrument section 6 moves between the closed position and the open position, respectively indicated by solid lines and one-dash, two-dot lines in FIG. 1. More precisely, the holding members 31 are opened when the operating shaft 12 is pushed forward, and are closed when the shaft 12 is pulled backwards.

As seen from FIG. 6B, each accurate groove 20 formed in the side of the member 18 of the cam member 16 has a clearance $S_1$ in front of the position the guide pin 36 take when the tongs 5 are closed completely. The arcuate groove 20 has a backlash $S_2$ between its edge rear 20b and the guide pin 36 when the guide pin 36 abuts on the front edge 20a of the arcuate groove 20 as illustrated in FIG. 6B.

As shown in FIG. 6B, too, the guide pin 36 of each tong 5 has a distal end face 36a and a proximal end face 36b. The proximal end face 36b comes into sliding contact with the rear edge 20b of the arcuate groove 20 when the cam member 16 is pushed forward to open the tongs 5. The distal end face 36a comes into sliding contact with the front edge 20a of the arcuate groove 20 when the cam member 16 is pulled backward to close the tongs 5. The distal end surface 36a has a radius of curvature which is almost the same as that of the front edge 20a of the arcuate groove 20. Similarly, the proximal end surface 36b has a radius of curvature which is virtually equal to that of the rear edge 20b of the arcuate groove 20.

As illustrated in FIG. 6A, the junctions 18a and 36c of the bottom and sides of each arcuate groove 20 is rounded. Also, each guide pin 36 has a rounded root. Cracks are therefore prevented from developing in the junctions 18a or in the root. Furthermore, the link arm 33 of each tong 5 has a small cross-section area (portion) 83 which is located near the root of the guide pin 36.

As shown in FIG. 4D, a connection pipe 37 has its distal end portion fitted in the positioning projection 23. The connecting pipe 37 is secured to the holding member 21 by means of adhesion, soldering, welding or the like.

Alternatively, the holding member 21 and the connecting pipe 37 may be formed integral.

The connecting pipe 37 has a snap-fit portion (connecting portion) 38 at its rear end. The snap-fit portion 38 can be removably connected to the sheath unit 7. The snap-fit portion 38 consists of four snap-fit arms 40 made by forming four slits 39 in the rear end portion of the connecting pipe 37 as illustrated in FIG. 4E. The connecting pipe 37 is made of austenitic stainless steel. Instead, it may be made of martensitic stainless steel to acquire a higher wear resistance. A projection (engagement projection) 41 protrudes from the outer peripheral of each snap-fit arm 40. The projection 41 has a distal slope 41a on the front side and a proximal slope 41b on the rear side.

The rear end portion of the distal shaft 13 (i.e., a part of the operation shaft 12) extends backwards from the snap-fit portion 38 of the holding member 21. It is placed in screw engagement with the connecting rod 15—outside the snap-fit portion 38.

A centering portion 15b is mounted on the rear end portion of the connecting rod 15. The portion 15b has an outer diameter, which is substantially equal to the inner diameter of an inner pipe 42 incorporated in the sheath unit 7. As shown in FIG. 4F, the centering portion 15b has four flat sides 43 which define water-supplying passages. Once the drive unit 9 has been incorporated into the sheath unit 7 and the centering portion 15b has been inserted into the inner pipe 42, water or the like supplied through a water-supplying cock 44 (later described) can flow through the passages defined by the flat sides 43 of the centering portion 15b and the inner circumferential surface of the inner pipe 42. The number of flat sides 43 the centering portion 15b has is not limited to four. Rather, the portion 15b may have any other number of flat sides to provide any number of water passages desired.

A thin distal ring 15c is mounted on the connecting rod 15 and located in front of the centering portion 15b. The distal ring 15c has an outer diameter, which is substantially equal to the inner diameter of the connecting pipe 37. The ring 15c moves into and from the space defined by the snap-fit arms 40 of the connecting pipe 37 as the operating shaft 12 is pushed forward to open the tongs 5 and pulled backward to close the tongs 5.

The thin distal ring 15c has a tapered portion 15d at the distal end. The tapered portion 15d abuts on the tapered surfaces 40a which are provided on the inner circumferential surfaces of the rear end portions of the snap-fit arms 40.

A pipe cover 45 and a connecting member 46 are fastened by screws to the rear end of the proximal shaft 14. The pipe cover 45 is made of resin such as polysulfone. The rear end portion of the connecting member 46 is formed integral with a spherical portion 47. The spherical portion 47 is removably connected to the operation section 3. The connecting member 46 is comprised of a small-diameter portion 48, an intermediate-diameter portion 49 and a large-diameter portion 50. The small-diameter portion 48 is coupled to the distal end of the spherical portion 47. The intermediate-diameter portion 49 connects the small-diameter portion 48 and the large-diameter portion 50 together. A heat-shrinking tube 51 made of Teflon or the like is mounted on the connecting member 46, electrically insulating the connecting member 46.

With reference to FIGS. 7A and 7B, the sheath unit 7 will be described in detail.

As shown in FIGS. 7A and 7B, the sheath unit 7 comprises the inner pipe 42, an insulating tube 52, and a connecting pipe 53. The inner pipe 42 is made of metal such as stainless steel. The insulating tube 52 is mounted on the inner pipe 42 and the connecting tube 53. The connecting pipe 53 is connected at its rear end to the front end of the inner pipe 42, by means of soldering, welding or the like. The connecting pipe 53 is made of austenitic stainless steel SUS303 or the like. Instead, it may be made of martensitic stainless steel SUS420J2 to acquire a higher wear resistance.

As shown in FIG. 8C, the connecting pipe 53 has grooves 54 in its outer circumferential surface. Similarly, the inner pipe 42 has grooves 54 in the outer circumferential surface of its distal end portion. Filled in these grooves 54 is adhesive agent, which adheres the insulating tube 52 to the connecting pipe 53 and, also to the inner tube 42.

An annular projection 55 is provided on the inner circumferential surface of the connecting pipe 53. The annular projection 55 has an inner diameter less than the outer diameter of the snap-fit portion 38 of the connecting pipe 37, which consists of four snap-fit arms 40. The connecting pipe 53 has a recess 56 made in its inner circumferential surface and located more proximal than the annular projection 55. The projections 41 of the snap-fit arms 40 are fitted in the recess 56 as long as the drive unit 9 remains connected to the sheath unit 7. A stepped portion 57 is provided between the annular projection 55 and the recess 56. The projections 41 of the snap-fit arms 40 abut on the stepped portion 57. As shown in FIG. 8F, the annular projection 55 has a front slope 55a and a rear slope 55b.

As shown in FIG. 8A, a positioning projection 58 protrudes from the distal end of the connecting pipe 53. The projection 58 is a half of a hollow cylinder as is seen from FIG. 8B. It abuts on the positioning projection 23 of the member 21, preventing the drive unit 9 inserted in the sheath unit 7 from rotating around the axis thereof. The distal end 59 of the positioning projection 58 is rounded.

As illustrated in FIG. 7B, a proximal coupling member 60 is connected to the proximal end portion of the sheath unit 7. The water-supplying cock 44 and a knob 61 are provided on the proximal coupling member 60. The coupling member 60 is removably coupled to the operation section 3.

A hollow cylinder 62 is mounted partly on the proximal end portion of the inner pipe 42 and partly on the proximal end portion of the insulating tube 52. Both the water-supplying cock 44 and the knob 61 are mounted on the hollow cylinder 62 and formed integral therewith. The water-supplying cock 44 incorporates a rubber plug 63. The plug 63 can be moved to open and close the water-supplying cock 44.

The proximal coupling member 60 has a snap-fit portion 64 at its proximal end portion. The snap-fit portion 64 is removably connected to the operation section 3. The snap-fit portion 64 has a connecting pipe 65 made of stainless steel or the like. As shown in FIG. 7B, the connecting pipe 65 has its distal end portion inserted and held in the proximal end portion of the hollow cylinder 62.

As is illustrated in FIGS. 8D and 8E, the rear end portion of the connecting pipe 65 has two slits 66 which extend in the axial direction. These slits 66 define two snap-fit arms 67. Each snap-fit arm 67 has a projection (engaging projection) 68 on the distal end portion. The projection 68 has a first slope 68a and a second slope 68b. The slopes 68a and 68b are located near the distal end of the arm 67 and the root thereof (i.e., the distal end of the sheath unit 7), respectively.

The connecting pipe 65 has a stepped portion 65a from which the snap-fit arm 67 projects. The stepped portion 65a contacts with the stepped portion 77a formed at the junction of the large-diameter hole 77 and small-diameter hole 78 made in the connection portion 73 of a fixed handle 70 (later described), when the operation section 3 is connected to the sheath unit 7. An annular rubber packing 69 is mounted on that portion of the connecting pipe 65 which is close to the hollow cylinder 62.

The first slope 68a of the projection 68 formed on the distal end portion of each snap-fit arm 67 inclines at an angle $\theta_1$ of about 30° to the axis of the connecting pipe 65. The second slope 68b of the projection 68 inclines at an angle $\theta_2$ of about 45° to the axis of the connecting pipe 65. These angles $\theta_1$ and $\theta_2$ may be changed. The smaller the angle $\theta_1$, the smaller the force required to insert the snap-fit arms 67 into the operation section 3.

The operation section 3, which is designed to open and close the tongs 5 provided at the distal end of the insertion section 2, will be described in detail, with reference to FIG. 9A.

The operation section 3 comprises the fixed handle 70 and a movable handle 71, either being a ring handle. The fixed handle 70 is generally L-shaped. The movable handle 71 is rotatably connected to the bending part of the fixed handle 70 by a connecting screw 72. Both handles 70 and 71 are made of metal and coated with an insulating film 79 of, for example, fluorine-based resin.

A hollow cylindrical connecting portion 73 is fasted to the upper end of the fixed handle 70. Projecting upwards from the outer circumferential surface of the connecting portion 73 is an electrode pin 74 holding a cap for electric cords connected to a high-frequency power supply (not shown). The lower end portion of the electrode pin 74 is covered with an insulating pipe 75 made of insulating material such as plastics. On the outer circumferential surface of the insulating pipe 75 there may be engraved the name of the instrument section 6 and the manufacturer thereof by means of embossing or the like. A rubber cap 76 is mounted on the rear end portion of the connecting portion 73, achieving watertight sealing. The rubber cap 76 has a hollow 76a in the outer end. The hollow 76a opens to receive the spherical portion 47 of the drive unit 9.

The connecting portion 73 has the large-diameter hole 77 and small-diameter hole 78. These holes 77 and 78 communicate with each other, extending in the axial direction of the connecting portion 73. The large-diameter hole 77 can hold the annular rubber packing 69 of the sheath unit 7, whereas the small-diameter hole 78 can hold the snap-fit portion 64 of the sheath unit 7. The the small-diameter hole 78 has a diameter which is substantially equal to the snap-fit portion 64 formed of the snap-fit arms 67, whereby the snap-fit portion 64 can therefore fit into the small-diameter hole 78.

Figure 9B:
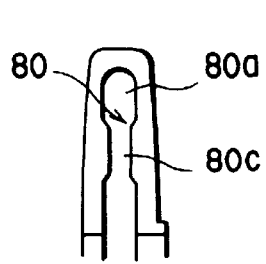
FIG. 9B is a front view of the mechanism coupling the ring handles of the first embodiment.
Figure 9C:
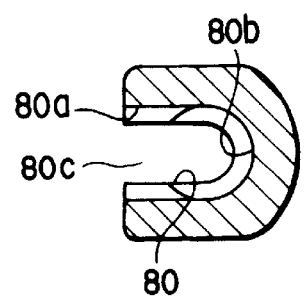
FIG. 9C is a sectional view taken along line 9C—9C shown in FIG. 9A.

The movable handle 71 has a connecting groove 80 made in its upper edge portion. The groove 80 extends vertically and communicates with an inlet hole 80a and two guide holes 80b and 80c. The second guide hole 80c connects the inlet hole 80a to the first guide hole 80b. The inlet hole 80a has almost the same diameter as the spherical portion 47 and can hold the spherical portion 47 of the connecting member 46, which is incorporated in the drive unit 9. The first guide hole 80b is provided for guiding the spherical portion 47 in vertical direction. As shown in FIGS. 9B and 9C, the second guide hole 80c is provided below the inlet hole 80a, for guiding the connecting member 46. It has a diameter smaller than the diameter of the spherical portion 47 of the connecting member 46 and greater than the diameter of the intermediate-diameter portion 49.

Since the inlet groove 80a opens not at the top of the movable handle 71, but in the front, the surgeon's finger will hardly cover the hole 80a while the surgeon is using the forceps 1, when a high-frequency current is supplied to the tongs 5 to perform treatment on the tissue clamped between the tongs 5. If the inlet hole 80a opened at the top of the movable handle 71, the surgeon's finger would likely to cover the hole 80a, to have a burn because of the high-frequency current leaking to the movable handle 71. Since the first guide hole 80b extends downward, reaching the connecting screw 72, it is easy to wash the interior of the connecting groove 80.

How to assemble the forceps 1, by connecting the operation section 3, the sheath unit 7 and the drive unit 9, will be explained.

First, the sheath unit 7 protecting the insertion section 2 is connected to the operation section 3. More specifically, the snap-fit portion 64 of the sheath unit 7 is inserted into the large-diameter hole 77 made in the connecting portion 73 of the fixed handle 70, and further into the small-diameter hole 78 of the connecting portion 73. As mentioned above, the snap-fit portion 64, which is comprised of the snap-fit arms 67, has an outer diameter substantially equal to the inner diameter of the small-diameter hole 78, and the projections 68 protrude outward from the snap-fit arms 67. Hence, the snap-fit arms 67 are elastically bent inwards when the portion 64 is inserted into the small-diameter hole 78 of the connecting portion 73.

The sheath unit 7 is deeper pushed into the small-diameter hole 78 until the stepped portion 65a of the connecting pipe 65 abuts on the stepped portion 77a provided at the junction of the large-diameter hole 77 and small-diameter hole 78 made in the connection portion 73 of the fixed handle 70. At this time, the projections 68 of the snap-fit arms 67 have moved out of the small-diameter hole 78, and the second slope 68b of each projection 68 is located at the proximal end of the small-diameter hole 78. Either snap-fit arm 67 therefore straightens, due to its elasticity.

Now that the snap-fit arms 67 have straightened up, their projections 68 abut on the rear end of the connection portion 73 of the fixed handle 70 as shown in FIG. 10. The sheath unit 7 is thereby removably connected to the connection portion 73 of the fixed handle 70. The snap-fit portion 64 will not slip from the small-diameter hole 78 of the connection portion 73 unless the snap-fit arms 67 are bent so much that the projections 68 moves into the small-diameter hole 78.

As long as the sheath unit 7 remains connected to the operation section 3, it can be rotated around its axis. The sheath unit 7 is prevented from rotating freely because of the friction between the inner surface of the large-diameter hole 77 and the annular rubber packing 69 mounted on the connecting pipe 65.

To remove the sheath unit 7 from the operation section 3, the surgeon only needs to hold and pull the sheath unit 7. As the unit 7 is pulled, the snap-fit arms 67 of the connecting pipe 65 are bent inwards until the projections 68 moves into the small-diameter hole 78. Then, the projections 68 are released from the engagement with the rear ends of the connection portion 73 of the fixed handle 70. As a result, the sheath unit 7 is pulled out of the connection portion 73 of the operation section 3.

As indicated above, the second slope 68b of either projection 68 inclines at the angle $\theta_2$ of about 45° to the axis of the connecting pipe 65. Thus, the sheath unit 7 can be disconnected from the operation section 3 only if it is pulled with a force greater than the friction between the second slope 68*b* of the projections 68, on the one hand, and the rear end of the connection portion 73, on the other hand. Were the angle $\theta_2$ 90° or more, it would be necessary to bend the snap-fit arms 67 inwards by, for example, squeezing the arms 67 with the fingers, thereby to release the projections 68 from the rear end of the connection portion 73.

The force required for pulling the sheath unit 7 from the operation section 3 may be reduced by decreasing the angle $\theta_2$, the resilient force of the snap-fit arms 67 or the thickness of the projections 68. Conversely, this force may be increased by increasing the angle $\theta_2$, the resilient force of the snap-fit arms 67 or the thickness of the projections 68.

The angles $\theta_1$ and $\theta_2$ at which the first slope 68*a* and second slope 69*b* of the projection 68 of each snap-fit arm 67 incline to the axis of the connecting pipe 65 are adjusted against each other, thereby altering the relationship between the force required to connect the sheath unit 7 to the operation section 3 and the force required to disconnect the sheath unit 7 from the operation unit 3. To state more precisely, if the angle $\theta_1$ is made greater than the angle $\theta_2$, the force for connecting the unit 7 to the section 3 will be greater than the force for disconnecting the unit 7 from the section 3. Conversely, if the angle $\theta_2$ is made greater than the angle $\theta_1$, the force for disconnecting the unit 7 from the section 3 will be greater than the force for connecting the unit 7 to the section 3. In other words, the force for connecting the unit 7 to the section 3 and the force for disconnect ing the unit 7 from the section 3 can be adjusted by changing the angles $\theta_1$ and $\theta_2$. The number of snap-fit arms 67 of the connecting pipe 65 is not limited to two. Rather, the pipe 65 may have three, four or more snap-fit arms.

It w ill now be explained how to operate the drive unit 9 and the assembly consisting of the operation section 3 and the sheath unit 7 connected to the section 3 in the manner explained above.

Figures 11A, 11B:
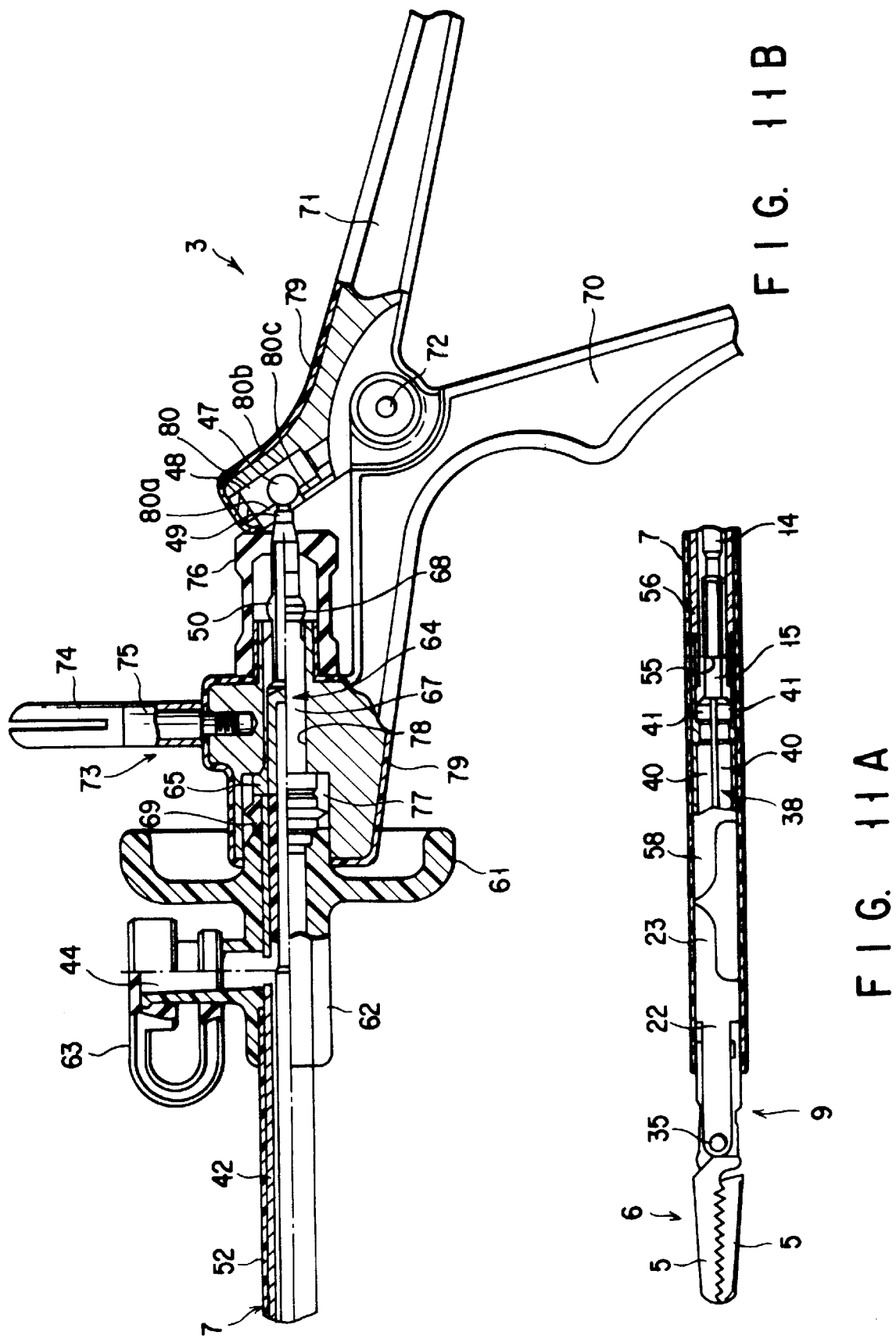
FIG. 11A is a longitudinal sectional view of the first embodiment, depicting the projecting portion of the drive unit abuts at its distal end on the distal end of the projecting portion of the sheath unit.
FIG. 11B is a longitudinal sectional view of the first embodiment, illustrating the movable handle rotated and set in contact with the rubber cap.

First, the movable handle 71 is rotated counterclockwise until it abuts on the rubber cap 76 as shown in FIG. 11B. Then, the drive unit 9 is inserted into the sheath unit 7 through the distal open end thereof. To be more specific, the spherical portion 47 of the connecting member 46 is inserted into the sheath unit 7 at first.

Next, the drive unit 9 is pushed deeper into the sheath unit 7 until the spherical portion 47 protrudes outward from the hollow 76*a* of the rubber cap 76 which is mounted on the rear end portion of the connection portion 73 provided in the operation section 3. The positioning projection 23 of the drive unit 9 and the positioning projection 58 of the sheath unit 7 may abut on each other, failing to fit together in overlapping position. This means that the drive unit 9 is not appropriately rotated around its axis with respect to the sheath unit 7. In this case, the drive unit 9 cannot be further inserted into the sheath unit 7. Furthermore, since the projections 23 and 58 are longer than the distance between the position where the spherical portion 47 starts entering the sheath unit 7 and the position where it is completely inserted in the sheath unit 7, the spherical portion 47 of the connecting member 46 protrudes outward from the hollow 76*a*, but for a short distance. The spherical portion 47 cannot be held in its entirety within the first guide hole 80*b* of the movable handle 71, though the movable handle 71 has been rotated counterclockwise, abutting the rubber cap 76, as is illustrated in FIG. 11B.

Then, the drive unit 9 is rotated around its axis with respect to the sheath unit 7 until the positioning projections 23 and 58 fit together in overlapping position as is illustrated in FIG. 12A. After the drive unit 9 has been thus positioned to the sheath unit 7, the operating shaft 12 is held in its forward position, closing both tongs 5 of the instrument section 6. In this condition, the drive unit 9 is inserted further into he sheath unit 7.

As long as the positioning projection 23 of the drive unit 9 and the positioning projection 58 of the sheath unit 7 remain in overlapping position, the spherical portion 47 provided at the rear of the drive unit 9 protrudes from the rubber cap 76 as shown in FIG. 12B—for a distance longer than as is illustrated in FIG. 11B.

The drive unit 9 eventually reaches the position where the projection 23 starts overlapping the projection 58 of the sheath unit 7. At this time, the projections 41 integral with the snap-fit arms 40 of the snap-fit portion 38 which is incorporated in the drive unit 9 abuts on the front slope 55*a* of the annular projection 55 provided on the connecting pipe 53 which is incorporated in the sheath unit 7. The snap-fit arms 40 are thereby bent inwards.

As the drive unit 9 is pushed deeper into the sheath unit 7, the projections 41 extend beyond the annular projection 55 into the recess 56 made in the inner circumferential surface of the connecting pipe 53. The distal slope 41*a* of the projection 41 abuts on the stepped portion 57 which is provided between the annular projection 55 and the recess 56. The rear end of the positioning projection 23 of the drive unit 9 abuts on the distal end of the positioning projection 58 of the sheath unit 7. The projections 23 and 58 therefore fit together completely. At this moment, the drive unit 9 finally reaches the desired position within the sheath unit 7. At this very moment, too, the spherical portion 47 of the drive unit 9 comes into engagement with the connecting groove 80 of the movable handle 71. More precisely, the spherical portion 47 is inserted into the inlet hole 80*a*.

The drive unit 9 is still further pushed into the sheath unit 7. The spherical portion 47 pushes the movably handle 71 backwards, rotating it clockwise in FIG. 12B. As a result of this, the spherical portion 47 of the connecting member 46 is held fully in the inlet hole 80*a* as is illustrated in FIG. 12B.

When the movable handle 71 is rotated clockwise, the spherical portion 47 moves into the first guide hole 80*b* which is also of the connecting groove 80. The small-diameter portion 48 and intermediate-diameter portion 49 of the connecting member 46 therefore sequentially enter the second guide hole 80*c*. Thus, the drive unit 9 is connected to the assembly which consists of the operation section 3 and the sheath unit 7.

The connecting member 46 has such a length that the spherical portion 47 would not be held in its entirely in the connection groove 80 or the guide hole 80*b* of the movable handle 71 when the projection 23 of the drive unit 9 abuts on the projection 58 of the sheath unit 7 as shown in FIGS. 11A and 11B. Hence, even if the movable handle 71 is rotated clockwise, no force will be applied to abut the projection 58 on the projection 23, which is so great as to damage the projection 23 or the projection 8, or both.

As long as the drive unit 9 assumes the desired position within the sheath unit 7, the operating shaft 12 of the drive unit 9 remains inserted in the connecting pipe 65 and held in place by the snap-fit arms 67. In this condition, the shaft 12 prevents both snap-fit arms 67 from bending inwards. This is because the pipe cover 45 provided for the shaft 12 and the heat-shrinking tube 51 mounted on the connecting member 46 have outer diameters which are substantially equal to the inner diameter of the connecting pipe 65. Since the snap-fit arms 67 do not bend inwards, the sheath unit 7 would not be disconnected from the operation section 3. That is, once the operation unit 3, the sheath unit 7, and the drive unit 9 have been combined together, the sheath unit 7 would not be removed from the operation section 3, causing no problems during the use of the forceps 1.

The force required to connect the drive unit 9 to and disconnect it from, the sheath unit 7 can be varied to any desired value, merely by the inclination angle of the distal slope 41a or proximal slope 41b of each snap-fit arm 40, the inclination angle of the front slope 55a or rear slope 55b of the annular projection 55 provided on the connecting pipe 53, the number of snap-fit arms 40, and/or the elasticity of the snap-fit arms 40. This method of varying the force is similar to the above-mentioned method of altering the force for connecting the sheath unit 7 to, and disconnecting the same from, the operation unit 3.

How the forceps 1 is operated to clamp living tissue will be explained below.

To open the tongs 5 of the instrument section 6, a surgeon rotates the movable handle 71 counterclockwise from the position shown in FIG. 1, thereby pushing the operating shaft 12 of the drive unit 9 forward. As the shaft 12 moves forward, the guide pins 36 of the tongs 5 moves along the accurate grooves 20 of the cam member 16, toward the rear ends of these grooves 20, gradually opening the tongs 5. As the shaft 12 further moves forward, the cam member 16 pushes the guide pins 36 forward since the guide pins 36 abuts on the rear edges 20b of the arcuate grooves 20. The tongs 5 are pushed forward, and further rotate in the opening direction, around the fulcrum pin 35 which passes through the elongated holes 34 of the link arms 33 which protrude from the proximal ends of tongs 5. The tongs 5 are thereby opened completely as illustrated in FIG. 15A.

At this time, the thin distal ring 15c mounted on the connecting rod 15 of the drive unit 9 is inserted completely within the snap-fit portion 38 having the snap-fit arms 40, as is illustrated in FIG. 15B. The snap-fit arms 40 therefore do not bend inwards, and the projections 41 do not come out of the engagement with the annular projection 55 incorporated in the sheath unit 7. It follows that the drive unit 9 would not be removed from the sheath unit 7 when the surgeon rotates the movable handle 71 counterclockwise in FIG. 1 to open the tongs 5.

In addition, the centering portion 15b of the rear end portion of the connecting rod 15 serves to set the rod 15 and the inner pipe 44 in complete axial alignment. The rod 15 can be moved back and forth along its axis to open and close the tong 5, without moving in the radial direction, while the operation section 3, the sheath unit 7, and the drive unit 9 remain assembled together. The distal ring 15c mounted on the connecting rod 15 is maintained in axial alignment with the snap-fit portion 38. The distal end of the ring 15c does not abut on the distal ends of the snap-fit arms 40 of the snap-fit portion 38. The distal ring 15c can smoothly inserted into and pulled from the snap-fit portion 38.

As long as the distal ring 15c stays within the space defined by the snap-fit arms 40, the drive unit 9 would not be removed from the sheath unit 7 even when the tongs 5 are opened.

To close the tongs 5 of the instrument section 6, the surgeon rotates the movable handle 71 clockwise in FIG. 1. The operation shaft 12 provided in the drive unit 9 is thereby pulled backwards, driving the cam member 16 in the same direction. Thus, as the shaft 12 is pulled, the guide pins 36 of the tongs 5 moves along the accurate grooves 20 of the cam member 16, toward the front ends of these grooves 20, gradually rotating the tongs 5 around the pin fulcrum 35 in the closing direction.

Each arcuate groove 20 has a clearance $S_1$ extending forward from the position the guide pin 36 assumes when the tongs 5 are closed. Due to this clearance $S_1$, the guide pin 36 does not abut on the distal edge of the groove 20 the moment the distal ends of the tongs 5 contact each other. The operation shaft 12 can be further pulled backwards for a distance equal to the clearance $S_1$. The force exerted on the movable handle 71 is therefore transmitted to the distal end portions of the tongs 5, enabling the tongs 5 to clamp thin tissue membrane firmly and reliably.

The clearance $S_1$ may be adjusted in accordance with the force which is to be applied to the tongs 5. In some cases, the accurate grooves 20 may be longer, reaching the distal edge of the cam member 16.

The forceps 1 is designed such that the inlet hole 80a or the guide hole 80b of the movable handle 71 extend almost at right angles to the axis of the connecting member 46 when the tongs 5 are closed as shown in FIG. 13B. A force can therefore be applied from the handle 71 on the connecting member 46 via the spherical portion 47 as the surgeon rotates the handle 71 clockwise in FIG. 1. The connecting member 46 is thereby pulled backwards along its axis. This makes it possible to transmit the force to the tongs 5 to close them with very high efficiency. The tongs 5 can clamp living tissue steadily between them, even if the tissue is a thin membrane.

In the present embodiment, the guide hole 80b or 80c extend almost vertically while the tongs 5 remain closed. Instead, the forceps 1 may be designed so that both guide holes 80b and 80c of the handle 71 may extend vertically when the tongs 5 are opened, defining a given angle between them, to clamp a comparatively thick tissue membrane.

The forceps 1 is designed such that the small-diameter portion 48 of the connecting member 46 is cut if the movable handle 71 is rotated clockwise to close the tongs 5, with a force much greater than required to clamp living tissue appropriately. Once the connecting member 46 is broken, the excessive force is no longer transmitted to the tongs 5. This prevents the tongs 5 from cutting the living tissue clamped between them.

As shown in FIG. 6A and as described above, the link arm 33 of each tong 5 has a small cross-sectional area (portion) 83 which is located near the root of the guide pin 36. The small cross-sectional area (portion) 83 is the first to be broken should an excessive force be exerted on the guide pin 36 from the arcuate groove 20 of the cam member 16. Once the connecting member 46 is broken, the excessive force is not transmitted to the tongs 5, and the tongs 5 would not cut the living tissue clamped between them.

During the use of the forceps 1, the cam member 16, the insulating tube 52 keeps covering the holding member 21 and the projection 23. Should the small-diameter portion 83 be broken, the fragments of the guide pins 36 or the like would not fly outside the insulating tube 52 to fall into the body cavity in which the instrument section 6 is located.

Moreover, as indicated above, the arcuate groove 20 has a backlash $S_2$ between its rear edge 20b and the guide pin 36 when the guide pin 36 abuts on the front edge 20a of the arcuate groove 20 as shown in FIG. 6B. Each guide pin 36 can abut on the rear edge 20b of the arcuate groove 20 after the cam member 16 moves a distance equal to the backlash $S_2$, when the surgeon rotates the movable handle 71 counterclockwise (FIG. 1), pushing the operating shaft 12 and the cam member 16 forwards in order to open the tongs 5. The thin distal ring 15c mounted on the connecting rod 15 can be inserted into the snap-fit portion 38 over a distance equal to the backlash $S_2$ as shown in FIG. 14B, before the cam member 16 pushes the guide pins 36 forward. The thin distal ring 15c is thereby prevented from bending the snap-fit arms 40 of the snap-fit portion 38 inwards. The projections 41 integral with the snap-fit arms 40 can no longer move inwards, either. The distal slope 41a of each snap-fit arm 40 remains in contact with the rear slope 55b of the annular projection 55. This reliably prevent the drive unit 9 from being disconnected from the sheath unit 7.

Suppose the instrument section 6 of the forceps 1 is inserted into a cleavage $H_1$ of living tissue H, with the tongs 5 closed, as is illustrated in FIG. 14A. When the tongs 5 are opened to tear the tissue H into two parts, the tissue H applies a reaction onto the tongs 5 to close them. Without backlash $S_2$ between the edge rear 20b of each arcuate groove 20 and the guide pin 36 of each tong 5, a force should be applied on the operating shaft 12 to push the shaft 12 forward and to remove the drive unit 9 from the sheath unit 7, when the movably handle 71 is rotated clockwise (FIG. 1), thereby opening the tongs 5. The snap-fit arms 40 would then bend inwards, and the distal slope 41a of each snap-fit arm 40 would be released from the annular projection 55, possibly disconnecting the drive unit 9 from the sheath unit 7.

Thanks to the backlash $S_2$ provided at each arcuate groove 20, the instrument section 6 can be inserted into the cleavage $H_1$ of the tissue H, with the tongs 5 closed. The drive unit 9 is prevented from slipping out of the sheath unit 7 while the forceps 1 is being used. This ensures safe treatment and operation on the living tissue H.

As described above, the distal shaft 13 and the cam member 16 are fastened, end to end, by screw engagement, and the distal shaft 13 and the connecting rod 15 are connected, end to end, by screw engagement. The position the rod 15 takes with respect to the snap-fit arms 40, i.e., the position of the thin distal ring 15c of the rod 15, can be adjusted along the axis of the rod 15 merely by rotating the distal shaft 13, the connecting rod 15 and the cam member 16.

The distal shaft 13 may be formed integral with the cam member 16 or with the connecting rod 15 may be formed integral. Alternatively, the proximal shaft 14 and the connecting rod 15 may be formed integral. Still alternatively, the distal shaft 13, the proximal shaft 14 and the connecting rod 15 may be formed integral.

As described above, the distal end surface 36a of each guide pin 36 has a radius of curvature substantially equal to that of the front edge 20a of the arcuate groove 20, and the proximal end surface 36b of the guide pin 36 has a radius of curvature virtually equal to that of the rear edge 20b of the arcuate groove 20. Hence, the area in which the distal end surface 36a and the front edge 20a contact each other, and the area in which the surface 36b and the rear edge 20b contact each other are larger than in the case where guide pins having a round cross section are used. This helps to reduce the wear on both the distal end surface 36a and the proximal end surface 36b.

The radius of curvature of the distal end surface 36a and proximal end surface 36b of each guide pin 36 may be changed, if necessary. Further, the distal end surface 36a and the proximal end surface 36b may be flat, not curved at all.

To hold the tissue H between the tongs 5, the surgeon first operates the operation section 3 as explained above, opening the tongs 5 as indicated by the one-dash, two-dot lines in FIG. 1, and then rotates the movable handle 71 clockwise in FIG. 1, closing the tongs 5 as indicated by the solid lines in FIG. 1.

Thereafter, the surgeon attaches the cap of the electric cords (not shown) to the electrode pin 74 of the operation section 3. The electric cords are connected to the high-frequency power supply (not shown, either). Thus, a high-frequency current may be supplied from the electrode pin 74 to the tongs 5 through the connecting portion 73, the snap-fit portion 64, the inner pipe 42, the connecting pipe 53, the snap-fit portion 38, the holding member 21 and the fulcrum pin 35. As a result, the tongs 5 cauterize the living tissue H or stop the bleeding on the tissue H.

Since the link arms 33 of the tongs 5, the cam member 16, the holding member 21 and the like are covered with the insulating tube 52, the high-frequency current would not leak from the arms 33, the member 16 or the member 21. The current flows to the tongs 5 only, reliably cauterizing only the tissue H clamped between the tongs 5. There is no possibility that the holding member 21, the cam member 16 and the link arms 33 cauterize the living tissue H when they happen to touch the tissue H.

While the surgeon is rotating the movable handle 71 clockwise in FIG. 1, thereby closing the tongs 5, which firmly clamp the tissue H, the connecting member 46 is strongly pulled backwards. The whole drive unit 9 is thereby pulled backwards, too. The connecting pipe 53, which abuts on the holding member 21 of the drive unit 9, is strongly forced onto the connecting portion 73 of the fixed handle 70. This causes the stepped portion 65a of the connecting pipe 65 to abut forcefully on the stepped portion 77a which is provided at the junction of the large-diameter hole 77 and small-diameter hole 78 made in the connection portion 73 of the fixed handle 70. When the stepped portion 65a abuts on the stepped portion 77a, a great friction is built up between these stepped portions 65a and 77a. The friction prevents the sheath unit from being rotated around its axis.

While the tongs 5 remain closed, clamping living tissue, the sheath unit 7 can hardly be rotated because of the friction generated between the stepped portion 65a of the connecting pipe 65 and the stepped portion 77a of the connection portion 73. Nonetheless, the sheath unit 7 can easily be rotated as long as the tongs 5 remain open, if the surgeon rotates the knob 61 provided on the proximal coupling member 60. The poisoning projection 58 protruding from the distal end of the connecting pipe 53 fits together, in overlapping position, with the projection 23 protruding from the rear end of the member 21. When the sheath unit 7 is rotated round its axis, the drive unit 9 is rotated in the same direction.

To remove the drive unit 9 from the sheath unit 7, the surgeon rotates the movable handle 71 clockwise in FIG. 1 after having closed the tongs 5 completely as illustrated in FIGS. 5A and 5B. While rotating the movable handle 71, the surgeon pulls the operating shaft 12 of the drive unit 9 backwards until the thin distal ring 15c mounted on the connecting rod 15 is fully pulled out of the snap-fit arms 40. Then, the surgeon holds the drive unit 9 with fingers and pulls it.

When the drive unit 9 is pulled, the projections 41 integral with the snap-fit arms 40 are pushed inwards since their distal slopes 41a contact the rear slope 55b of the annular projection 55. Thus pushed, the projections 41 move forwards beyond the annular projection 55. The surgeon further pulls the drive unit 9. Simultaneously, he or she rotates the movable handle 71 counterclockwise (FIG. 1) to the position shown in FIG. 11B. The spherical portion 47 of the connecting member 46 is thereby moved away from the guide hole 80b. This done, the drive unit 9 can be completely removed from the sheath unit 7.

As indicated above, the thin distal ring 15c of the connecting rod 15 has a tapered portion 15d at the distal end, and the snap-fit arms 40 have a tapered surface 40a each, on the inner circumferential surface of the rear end portion. The tapered surface 40a of each snap-fit arm 40 abuts on the tapered portion of the thin distal ring 15c when the projection 41 integral with the snap-fit arm 40 is pushed inwards. The connecting rod 15 is thereby pushed backwards. The thin distal ring 15c of the rod 15 can be easily pushed from the snap-fit portion 38 backwards. This facilitates the removal of the drive unit 9 from the sheath unit 7.

As shown in FIG. 14A, the link arm 33 of each tong 5 has a bulging portion 81, near the holding member 31 thereof. The bulging portion 81 is located just in front of the insulating tube 52 and a little protrude in radial direction of the insulating tube 52. The bulging portions 81 almost close the distal end of the insulating tube 52 while the tongs 5 remain closed.

If the link arms 33 has not the bulging portions 81, there would be provided a gap between each link arm 33 and the distal end of the insulating tube 52. Into this gap, the airtight valve body provided in a trocar tube might slip when the forceps 1 is inserted into or pulled from a body cavity through the trocar. The valve body, if caught in the gap, would make smooth insertion or removal of the forceps 1 impossible. Thus, the bulging portions 81 of the link arm 33 serve to achieve smooth insertion of the forceps 1 into a body cavity and smooth removal of the forceps 1 from the body cavity.

The rubber plug 63 can be removed from the water-supplying cock 44, and a water-supplying tube (not shown) can be connected to the cock 44. Then, water or physiological saline can be supplied into the forceps 1. The water or the physiological saline flows from the distal end of the insulating tube 52 after passing through the gap between the inner circumferential surface of the inner pipe 42 and the proximal shaft 14 of the drive unit 9, through the gap between the flat sides 43 of the connecting rod 15 and the inner circumferential surface of the inner pipe 42, and through the gap between the circumferential surface of the snap-fit portion 38 and the distal shaft 13, and through the water-supplying grooves 17b of the cam member 16. It is therefore possible not only to supply physiological saline into a body cavity through the forceps 11, but also to wash the interior of the inner pipe 42 of the sheath unit 7 by passing water through the pipe 42.

The rubber plug 63 of the sheath unit 7 and the rubber cap 76 of the operation section 3 are be of the same color so that the surgeon may not connect the operation section 3 to a wrong sheath unit, or the sheath unit 7 to a wrong operation section. Similarly, the pipe cover 45 and heat-shrinking tube 51 of the sheath unit 7 are of the same color as the rubber cap 76 of the operation unit 3, for preventing connection of the sheath unit 7 with a wrong operation unit, and vice versa.

The forceps 1 described above is advantageous in some respects.

First, the guide pin 36 of each tong 5 is prevented from reaching the rear edge 20b of the arcuate groove 20 when the tongs 5 are closed, since the arcuate groove 20 has a clearance $S_1$ which extends forward from the position the guide pin 36 assumes when the tongs 5 are closed. Therefore, as the movable handle 71 is further rotated after the tongs 5 have been closed, the guide pins 36 can further move forward along the arcuate grooves 20, whereby the tongs 5 can clamp a thin tissue membrane, such as the mesentery, firmly and steadily enough to peel the membrane off reliably.

Second, the snap-fit portion 64 provided at the proximal end of the sheath unit 7 allows for easy connection of the sheath unit 7 to and from the operation unit 3, merely by setting the projections 68 of the snap-fit arms 67 into and out of the engagement with the stepped portion provided at the rear end of the connection portion 73 of the operation section 3. The sheath unit 7 can therefore be easily and quickly connected to the operation unit 3 and disconnected therefrom.

Third, since the snap-fit portion 38 of the drive unit 9 can be easily and quickly connected to and disconnected from the annular projection 55 of the connecting pipe 53 incorporated in the sheath unit 7, the drive unit 9 can be easily connected to and disconnected from the sheath unit 7 within a short time. The forceps 1 can therefore be assembled by combining the operation unit 3, the sheath unit 7 and the drive unit 9, and overhauled by disconnecting these units 3, 7 and 9, more easily and quickly than the conventional forceps whose components are joined together screw means.

Fourth, having no screw couplings for connecting the operation unit 3, the sheath unit 7 and the drive unit 9, the forceps 1 is more easy to wash than otherwise, because much time is required to wash each screw coupling which has a threaded member. Not only the interior of the sheath unit 7, but also and the link arms 33, the cam member 16 having arcuate grooves 20 and the snap-fit portion 38, which are located at the joints among the units 3, 7 and 9, are easy to wash and sterilize. The forceps 1 can be maintained clean and sterilized, as is required of any kind of a medical instrument.

In the first embodiment, the proximal shaft 14 of the drive unit 9 may be made of super-elasticity alloy which is a shape-memory alloy. A representative example of super-elasticity alloy is a Ni—Ni alloy. The proximal shaft 14, if made of super-elasticity alloy, is advantageous in the following two respects.

First, the proximal shaft 14 is elongated, when the operating shaft 12 of the drive unit 9 is exerted with a force greater than necessary for the tongs 5 to clamp a thin tissue membrane firmly and steadily. In other words, the proximal shaft 14 absorbs an excessive force, which is not transmitted to the tongs 5. The tissue membrane will not be damaged. Nor will the operating shaft 12 be broken at all.

Second, the proximal shaft 14 can regain its original length when the force is released from the operating shaft 12, provided that specific measures are taken to inhibit the movable handle 71 from rotating excessively.

Furthermore, the drive mechanism 8 having the cam mechanism K may be replaced by a drive mechanism which incorporates a link mechanism. If this is the case, as well, the operating shaft of the drive mechanism can be made of super-elasticity alloy, to attain the same advantages as described in the preceding paragraphs.

Needless to say, the operating shaft 12 may be made of any other elastic material other than super-elasticity alloy. For example, the shaft 12 can be made of steel for use in manufacturing piano lines and springs. In this case, too, the same advantages as set forth in the preceding paragraphs can be achieved, only if appropriate values are selected for the longest distance which the shaft 12 can move as the movable handle 71 of the operation section 3 is rotated, and for the maximum force which may be exerted on the shaft 12. It should be noted that the longest distance the shaft 12 can move is determined by the lever ratio of the handle 71 (i.e., the ratio of the distance between one end of the lever 71 and the fulcrum to the distance between the other end and the fulcrum). specific measures may be taken to inhibit the movable handle 71 from rotating excessively, as in the case the shaft 12 is made of super-elasticity alloy.

A forceps according to the second embodiment of the present invention will be described, with reference to FIGS. 16A to 16D.

The second embodiment is characterized in that, as shown in FIG. 16A, a screw coupling portion 91 is provided, connecting the holding member 31 of a drive unit 9 to the connecting pipe 37 of a snap-fit portion 38. Further, as shown in FIG. 16B, a hollow cylindrical projection 92 protrudes from the rear ends of snap-fit arms 40 backwards. As shown in FIG. 16D, the projection 92 has an annular member 93 at its proximal end portion.

As can be seen from FIG. 16B and 16C, the snap-fit portion 38 has four elongated holes 94, not slits as formed in the connecting pipe 37 used in the first embodiment. Those parts of the snap-fit portion 38, which lie among the elongated holes 94, function as snap-fit arms 40. The number of the elongated holes 94 and the width thereof may be altered, if necessary. The projection 41 integral with each snap-fit arm 40 is located at the middle part of the corresponding elongated hole 94 of the snap-fit portion 38. The thin distal ring 15c of a connecting rod 15 is longer than its counterpart used in the first embodiment by the distance between the projection 41 and the annular member 93.

The other components of the second embodiments are identical to those of the first embodiment. Therefore, they are designated at the same reference numerals in FIGS. 16A to 16D and will not be described in detail.

Like the first embodiment, the second embodiment has no screw couplings for connecting the operation unit 3. Hence, the forceps according to the second embodiment can therefore be assembled by combining the operation unit 3, the sheath unit 7 and the drive unit 9, and overhauled by disconnecting these units 3, 7 and 9, more easily and quickly than the conventional forceps whose components are joined together screw means.

The second embodiment is advantageous in two respects. First, the projections 41 integral with the snap-fit arms 40 and the connecting pipe 37 provided in the snap-fit portion 38, if they have been worn and damaged, can be replaced with new ones merely by rotating the screw coupling portion 91, disconnecting the pipe 37 from the holding member 21. Second, since the snap-fit arms 40 are connected together at the distal end and connected together at the proximal end by annular member 93, they are hardly bent outwards even if they abut on anything while the drive unit 9 is being connected to or disconnected from the sheath unit 7. The drive unit 9 can therefore be connected to and disconnected from the sheath unit 7 with high reliability.

A forceps according to the third embodiment of the invention will be described, with reference to FIGS. 17A to 17G.

The third embodiment is characterized by an instrument section 103 which is a modification of the instrument section 6 incorporated in the first and second embodiments.

As shown in FIGS. 17A and 17B, the instrument section 103 comprises a fixed blade 101 and a movable blade 102, instead of the tongs 5 used in the first and second embodiments. The fixed blade 101 is coupled to the distal end of the first support arm 22 projecting from the holding member 21. The fixed blade 101 has an arcuate edge 104. As best shown in FIG. 17D, a fulcrum pin 105 is fastened at one end to the fixed blade 101 and at the other end to the distal end portion of the second support arm 22. The movable blade 102 is rotatably mounted on the fulcrum pin 105 thus caulked.

The distal shaft 13, which is part of an operating shaft 12 of the same type used in the first embodiment, extends forwards. The proximal end of the movable blade 102 is rotatably connected to the distal end of the shaft 13 by a pin 106. The distal shaft 13 has a flat distal portion 107 as is illustrated in FIG. 17E. The distal portion 107 has an elongated hole 108, in which the pin 106 is held by means of caulking. An appropriate backlash $S_2$ is provided between the pin 107 and the proximal edge of the elongated hole 108.

As shown in FIG. 17F, the distal shaft 13 has a flat side 109, providing a space through which the movable blade 102 can rotated around the fulcrum pin 105, without abutting the inner circumferential surface of the holding member 21. That is, the blade 102 can rotate as the distal shaft 13 moves forward and backward when a surgeon rotates the movable handle 71 of the operation section 3. As the movable blade 102 is rotated, the distal shaft 13 may move up and down. Nonetheless, the shaft 13 does not contact inner circumferential surface of the holding member 21, thanks to the flat side 109.

The third embodiment differs from the first embodiment in that the holding member 21 and the snap-fit portion are formed integral. Moreover, as shown in FIG. 17G, the centering portion 15b of the connecting 15 has two flat sides 43. The flat sides 43 define two water passages. The portion 15b may have more or less flat sides. It may have curved sides, instead of flat ones.

The other components of the third embodiments are identical to those of the first embodiment. Therefore, they are designated at the same reference numerals in FIGS. 17A to 17G and will not be described in detail.

How to operated the third embodiment will be explained below.

First, the surgeon rotates the movable handle 71, thereby moving the operating shaft 12 forward or backward, whereby the movable blade 102 is rotated around the fulcrum pin 105, assuming open position or closed position with respect to the fixed blade 101. Living tissue or the like, if any clamped between the blades 101 and 102, is cut when the movable blade 102 is rotated to the closed position.

To open the movable blade 102, the surgeon rotates the movable handle 71, sliding the distal shaft 13 forward. When the distal shaft 13 moves forward for a distance equal to the backlash $S_2$, guided by the pin 106 inserted in the elongated hole 108 made in the flat distal portion 107 of the shaft 13, the pin 106 abuts on the proximal edge of the elongated hole 108. At this time, the thin distal ring 15c of a connecting rod 15 enters the space among the snap-fit arms 40 of the snap-fit portion 38 in the same way as in the first embodiment. The projections 41 integral with the snap-fit arms 40 are thereby prevented from bending inwards. As a result, the drive unit 9 is not removed from the sheath unit 7. The operating shaft 12 is further pushed forward after the pin 106 abuts on the proximal edge of the elongated hole 108, rotating the movable blade 102 around the fulcrum pin 105.

Like the first embodiment, the third embodiment has no screw couplings for connecting the operation unit 3. Hence, the forceps according to the third embodiment can be assembled by combining the operation unit 3, the sheath unit 7 and the drive unit 9, and overhauled by disconnecting these units 3, 7 and 9, more easily and quickly than the conventional forceps whose components are joined together screw means.

A forceps according to the fourth embodiment of the invention will be described, with reference to FIGS. 18A to 18C and FIGS. 19A and 19B.

Figure 19A:
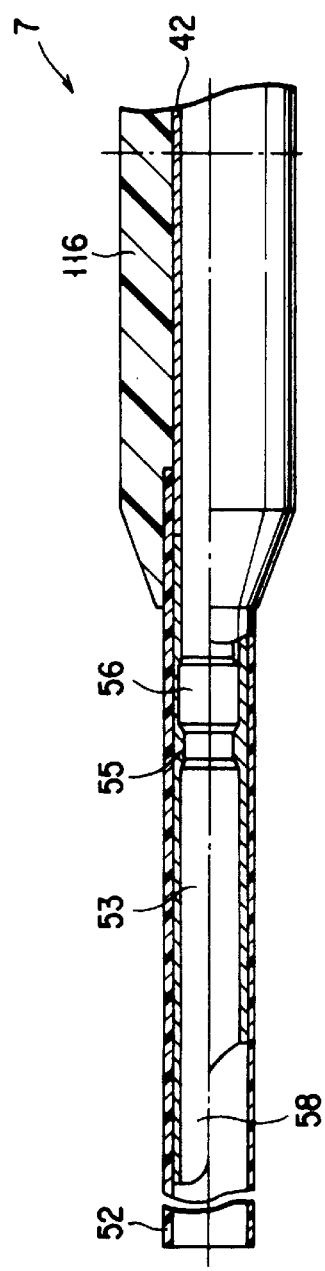
FIG. 19A is a cutaway side view showing the distal end portion of the sheath unit of the fourth embodiment of the invention.
Figure 19B:
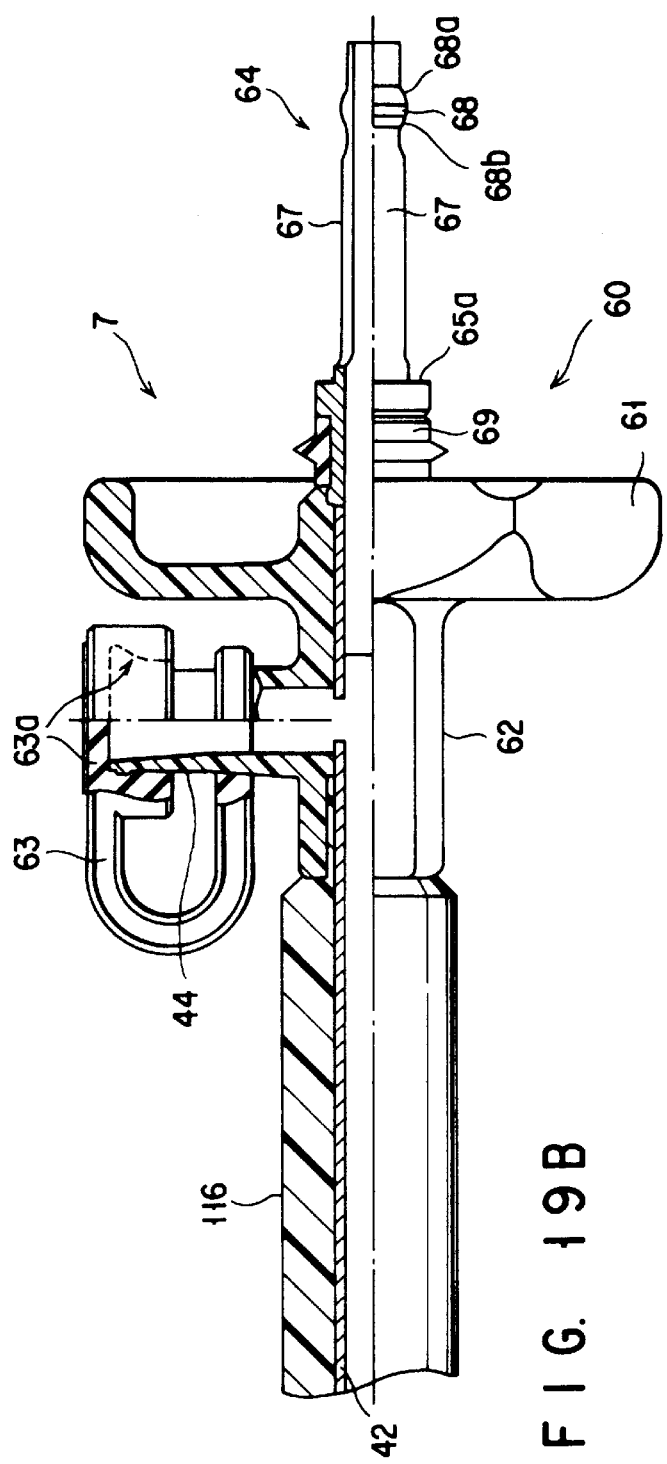
FIG. 19B is a cutaway side view illustrating the proximal end portion of the sheath unit incorporated in the fourth embodiment.

The fourth embodiment is characterized in that the tongs 3 are modified as shown in FIGS. 18A to 18C, and that the sheath unit 7 is modified as illustrated in FIGS. 19A and 19B.

As shown in FIG. 18A, each tong 5 comprises a main body 111. The distal end portion 112 of the main body 111 is curved and has an inner curved surface 112a and an outer curved surface 112b. The inner curved surface 112a has a radius of curvature which is substantially equal to the radius of a tubular tissue such as a blood vessel. Namely, the distal end portion 112 is shaped to hold tubular tissue.

As shown in FIG. 18C, two grooves 113 are made in the tissue-holding surface of the main body 111, which opposes the tissue-holding surface of the other tong 5. Both grooves 113 are curved in the same direction as the distal end portion 112. These grooves 113 helps to prevent the living tissue from moving sideways on the tissue-holding surface of the main body 111. Thus, they facilitate the holding and peeling of tissue. The main body 111 has a rectangular groove 114 in the proximal portion, as illustrated in FIG. 18A and 18B. The rectangular groove 114 may be circular or may assume any other shape.

FIG. 18D illustrates a modified tong for use in the fourth embodiment. The modified tong has a main body 111 which has a curved portion 115. The portion 115 is gently curved. Two grooves 113 are made in the tissue-holding surface of the main body 111, curved along the inner curved surface 115a of the main body 111, two other grooves 113 are made in the tissue-holding surface of the main body 111, curved along the outer curved surface 115b of the main body 111.

Two airs of groove 113 serve to prevent the living tissue from moving sideways on the tissue-holding surface of the main body 111. Thus, they facilitate the holding and peeling of tissue. The direction and radius of curvature in and at which the main body 111 is curved, and the number and length of grooves 113 may be altered, if necessary.

As shown in FIG. 19a and 19B, an insulating tube 52 is mounted only one the distal end portion of the sheath unit 7. The distal end portion of the tube 52 covers the distal end portion of the inner pipe 42 provided in the sheath unit 7. Further, a large-diameter pipe 116 is mounted on the inner pipe 42 of the sheath unit 42. The pipe 116 is formed by extrusion molding and made of, for example, polysulfone reinforced with glass fibers. Its outer diameter is about twice the outer diameter of the inner pipe 42. As shown in FIG. 19A, the large-diameter pipe 116 extends forward to a position where it covers the rear end portion of the insulating tube 52. It extends backward to the proximal coupling member 60 provided at the proximal end of the sheath unit 7 and is fastened to the member 60 by means of adhesion or the like. The pipe 116 may have any outer diameter desirable for its use. Nonetheless, in the present embodiment, the pipe 116 has such an outer diameter that it can be guided through a large-diameter trocar (not shown).

When the drive unit 9 having tongs of the type shown in FIGS. 18A to 18C is connected to the sheath unit 7 shown in FIGS. 19A and 19B, the resultant forceps can be guided through a large-diameter trocar. If the drive unit 9 were connected to the sheath unit of the first embodiment, the resultant forceps could not be guided through a small-diameter trocar. This is because, the curved distal end portion 112 of either tong 5 would extend outward from the insulating tube 52 as views in the axial direction thereof.

As shown in FIG. 19B, that portion of the rubber plug 63 mounted on the water cock 44 has an inner diameter which gradually decreases toward the inner tube 42. Since the rubber plug 63 has a tapered axial hole 63a, dust is hardly accumulated in the deep part of the interior, and the rubber plug 63 is easy to wash and sterilize.

With reference to FIGS. 20A to 20E, a modified sheath unit for use in the fourth embodiment will be described.

The modified sheath unit comprises two insulating bushes 121 and 122 in place of the large-diameter pipe 116 used in the fourth embodiment. Both bushes 121 and 122 are made of insulating material such as polysulfone. The first insulating bush 121 is provided at the distal end of the sheath unit 7 as shown in FIG. 20a. The second insulating bush 122 is provided at the proximal end of the sheath unit 7 as shown in FIG. 20b. The modified sheath unit further comprises a reinforcing pipe 123 and an insulating tube 124. The pipe 123 is made of, for example, stainless steel. Its end portions are mounted on the rear end portion of the first bush 121 and the front end portion of the second bush 122, respectively. The bushes 121 and 122 are therefore connected by the reinforcing pipe 123. The tube 124 is made of insulating material such as fluorine resin and is mounted on the reinforcing pipe 123, covering the same.

As can be seen from FIGS. 20C to 20E, the insulation bushes 121 and 122, the reinforcing pipe 123 and the insulating pipe 124 are arranged eccentric to the inner pipe 42. Hence, when the drive unit 9 having main bodies 111 shown in FIGS. 18A to 18C is connected to the modified sheath unit 7, the curved distal end portion 112 of either tong 5 can extend outward from the insulating tube 52 for some distance, because the sheath unit 7 is arranged eccentric to the inner pipe 42.

The first insulating bush 121 has an outer diameter X less than the outer diameter Y of the insulating tube 124, which in turn is less than the outer diameter Z of the second insulating bush 122. Namely, X<Y<Z. Therefore, the combination of the modified sheath unit 7 and the drive unit 9 of FIGS. 18A to 18C can easily be guided through a trocar into a body cavity and therefrom. If necessary, the bushes 121 and 122 and the insulating tube 124 may have the same outer diameter—that is, X=Y=Z.

Figures 21A, 21B:
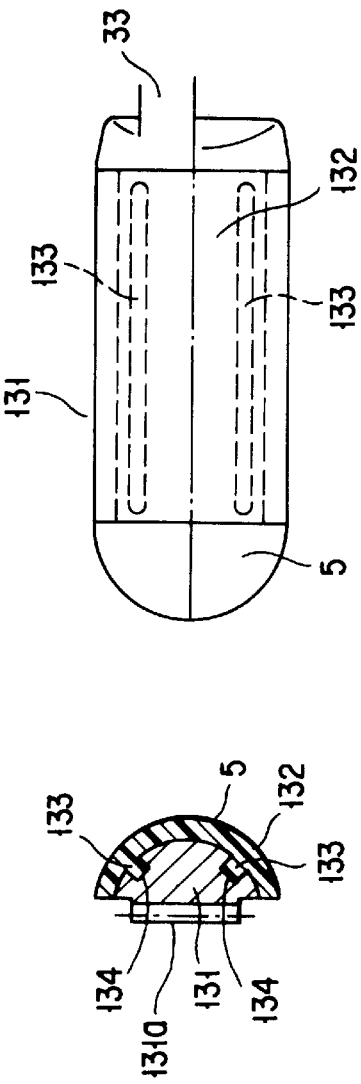
FIG. 21A is a cross-sectional view showing a first modified instrument section for use in the first embodiment.
FIG. 21B is a plan view of the tongs of the first modified instrument section.

FIGS. 21A and 21B show a first modified instrument section for use in the first embodiment, more precisely the tongs 5 of the modified instrument section. As shown in FIGS. 21A and 21B, either tong 5 comprises a main body 131 having a tissue-holding surface 131a. An insulating member 132 made of plastics and formed by insert molding or the like is mounted on the outer surface of the main body 131, i.e., the surface facing away from the tissue-holding surface 131a. The insulating member 132 may be made of insulating material such as ceramics.

As shown in FIGS. 21A and 21B, the main body 131 has two grooves 133 in its outer surface. The material of the insulating member 132 fills the grooves 133, forming projections 134. With the projections 134 fitted in the grooves 133, the member 132 is prevented from falling off the main body 131. The grooves 133 may be replaced by holes.

Since the outer surface of the main body 131 is covered with the insulating member 132, a high-frequency current flowing through the main body 131 serves to cauterize only the tissue contacting the tissue-holding surface 131a, never cauterizing the tissue which happens to contact the insulating member 132. In other words, there is no risk that the high-frequency current is applied to the tissue which the surgeon does not intend to cauterize.

Not only the outer surface, but also the tissue-holding surface 131a may be partly covered with an insulating member. The tong 5 may be manufactured, first by forming an insulating layer on all surfaces of the main body 131 and then by removing a part of the layer, thereby exposing only part of the main body 131 from which to apply the high-frequency current to living tissue.

Figure 21C:
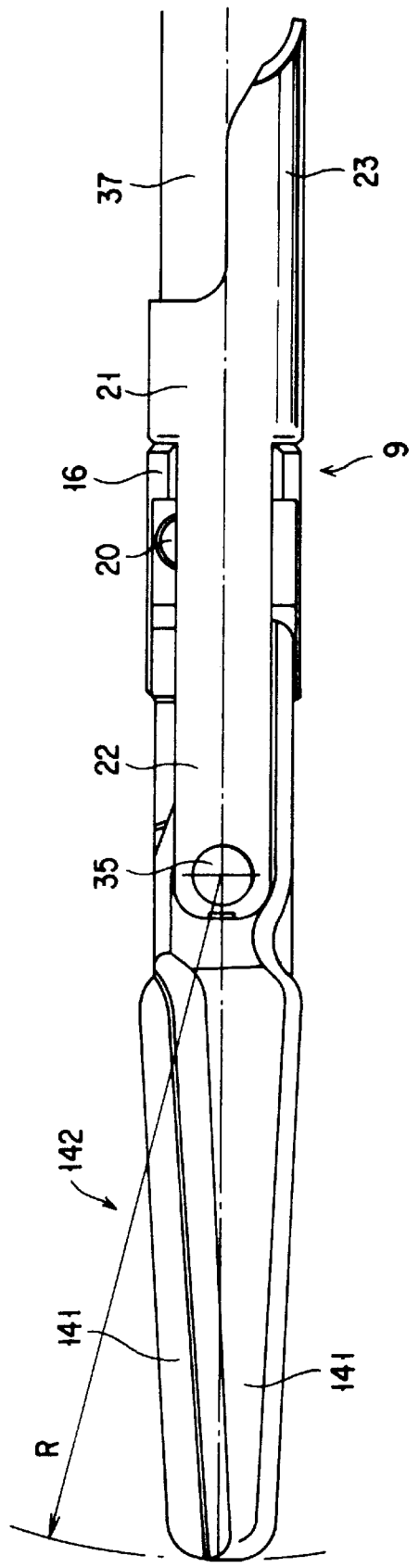
FIG. 21C is a side view of second modified instrument section for use in the first embodiment.

FIG. 21C is a side view of a second modified instrument section 142 for use in the first embodiment. The modified instrument section 142 comprises tongs 141 shaped like scissors. The section 142 is connected to the distal end of the drive unit 9. The distal end of either scissor-shaped tong 141 is rounded with a radius R of curvature which is equal to the distance between it and the fulcrum pin 35 coupling the tongs 141 together. Except for the features mentioned here, the instrument section 142 is identical to the instrument section 6 used in the first embodiment. The components identical or similar to those of the section 6 are designated at the same reference numerals in FIG. 21C and are not described.

FIGS. 22A and 22B illustrate third modified instrument section 152 for use in the first embodiment. As seen from FIGS. 22A and 22B, the instrument section 152 is connected to the distal end of the drive unit 9. It has a pair of tongs 151 shaped like scissors.

As shown in FIG. 22A, the block-shaped member 18 of the cam member 16 has a narrow part 153 and a broad part 154, both located located between the link arms 33 connected to the scissor-shaped tongs 151. The narrow part 153 has a width less than the gap between the ling arms 33. The broad part 154 has a width substantially equal to the gap between the ling arms 33. Except for these features, the instrument section 152 is identical to the instrument section 6 used in the first embodiment. The components identical or similar to those of the section 6 are designated at the same reference numerals in FIGS. 22A and 22B and are not described.

As the operating shaft 12 of the drive unit 9 is moved forward to open the scissor-shaped tongs 151, no friction is generated between the narrow part 153 and the link arms 33 as long as the narrow part 153 is locate between the link arms 33. The operating shaft 12 can therefore move forward smoothly. When the proximal ends of both link arms 33 reach the stepped portion provided between the narrow part 153 and broad part 154 of the block-shaped member 18, the thin distal ring 15c of a connecting rod 15 enters the space defined by the projections 41 integral with the snap-fit arms 40.

When the broad part 154 of the block-shaped member 18 moves into the gap between the link arms 33 as the operating unit 12 is further moved forward, a greater force is then required to move the shaft 12 still forward. Since the thin distal ring 15c is now within the space defined by the projections 41 of the snap-fit arms 40 do not bend inward even if a force is applied to pull the drive unit 9 from the sheath unit 7. Thus, there is no possibility that the drive unit 9 is disconnected from the sheath unit 7 while the scissor-shaped tongs 151 are being opened.

A modified forceps 1 according to the invention will be described, with reference to FIGS. 23A to 25B. Of these figures, FIGS. 23A and 23B show the sheath unit 7 incorporated in a modification derived from the first embodiment, and FIGS. 24A to 24C and FIGS. 25A and 25B show the drive unit 9 of the modification.

The sheath unit 7 is almost identical to its counterpart of the fourth embodiment. That is, a large-diameter pipe 161 is mounted on the inner pipe 42. As shown in FIG. 23A, the distal end portion of the large-diameter pipe 161 extends forward a little from the distal end of the connecting pipe 53. The pipe 161 covers the connecting pipe 53. An insulating tube 162 is mounted on the large-diameter pipe 161, covering the pipe 161. The inner diameter of the insulating tube 162 is equal to the outer diameter of the large-diameter pipe 161. The outer diameters of the large-diameter pipe 161 and the insulating tube 162 are less than the inner diameter of a trocar tube so that the sheath unit 7 may be guided through the trocar tube.

The holding member 21 of the drive unit 9 has a relatively large outer diameter so that it may be placed within the insulating tube 162 of the sheath unit 7. The cam member 16 also has an outer diameter large in proportion to the outer diameter of the holding member 21. Furthermore, the main body 163 of either tong 5 has a comparatively large outer diameter, but is made thin enough to be placed within the insulating tube 162 of the sheath unit 7. The main body 163 of either tong 5 has a distal portion 164 curved inwards as shown in FIG. 24A. As shown in FIG. 24C, the distal portion 164 has a triangular window 165 in its tip.

The modification is advantageous in two respects. First, since the pipe 161 provided at the distal end of the insertion section 2 and the main body 163 of either tong 5 have large diameters, the forceps 1 can reliably clamp a relatively large tissue present in a body cavity. Second, since both tongs 5 are relatively long, they are more flexible than they are shorter, minimizing the risk that an excessive clamping force is applied on living tissue to damage the tissue.

FIG. 26 is a longitudinal sectional view of the first embodiment, showing an A-cord cap 172 connected to the electrode pin 74 mounted on the fixed handle 70. The cap 172 comprises a pin connector 173 and an insulating tube 174. The pin connector 173 is made of metal such as stainless steel. The insulating tube 174 is mounted on the connector 173 and made of plastics such as polysulfone or other insulating material. The insulating tube 174 has its distal end 174a located in front of the distal end 173a of the pin connector 173. The pin connector 173 is connected to the wire 175 provided in the A-cord 171. A high-frequency current is supplied to the pin connector 173 through the wire 175 from a high-frequency power source (not shown). The current is then supplied from the pin connector 173 to the electrode pin 74 of the forceps 1.

Since the distal end 174a of the insulating tube 174 is positioned in front of the distal end 173a of the pin connector 173, the high-frequency current is less likely to leak from the interface 176 between the distal end 174 of the insulating tube 174 and the connection portion 73 of the fixed handle 70, than in the case where the distal end 174a is flush with the distal end 173a of the pin connector 173.

Figure 27A:
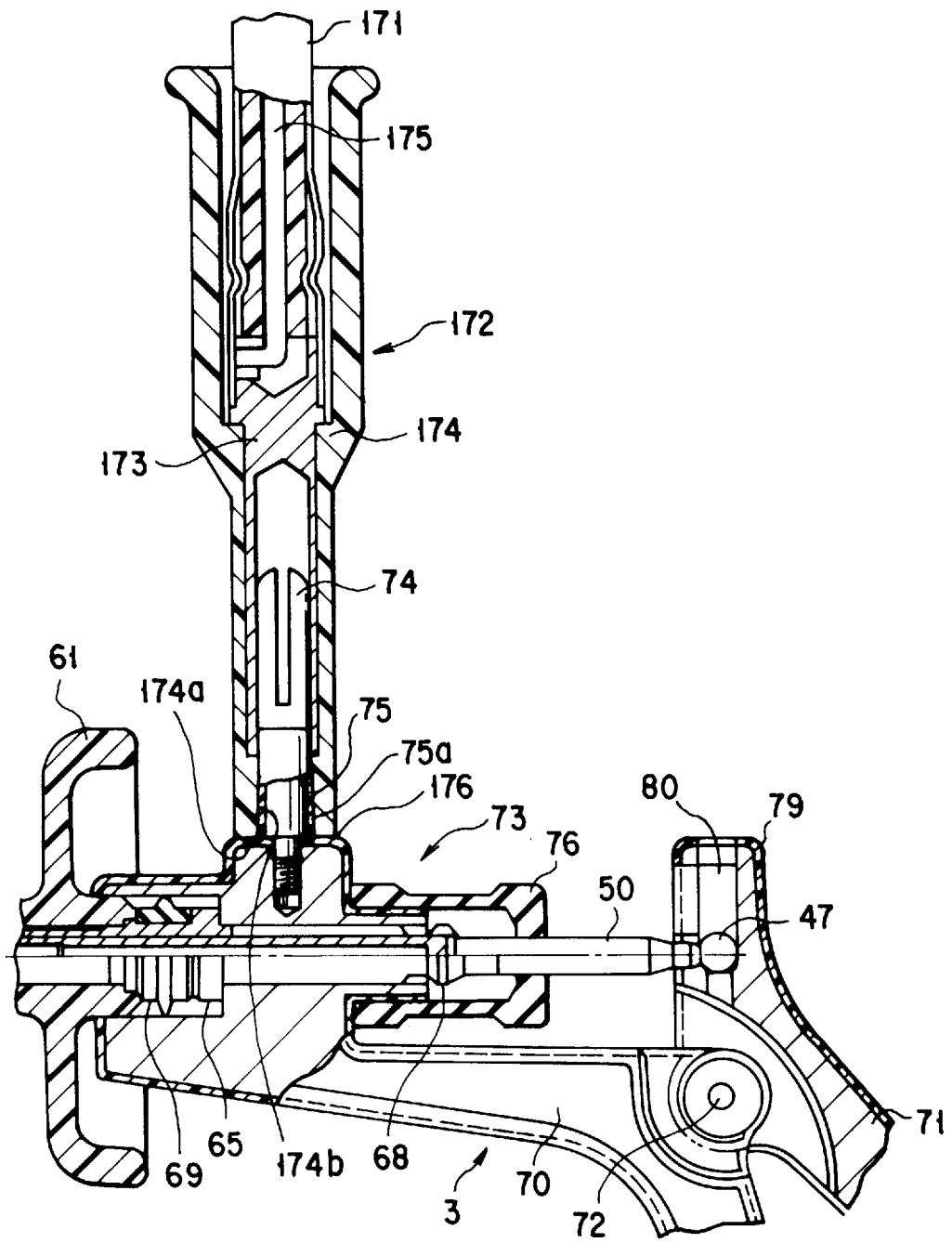
FIG. 27A is a longitudinal sectional view showing a first structure of connecting the A-cord cap to the electrode pin.

FIG. 27A illustrates a first structure of connecting the A-cord cap 171 to the electrode pin 74. The insulating tube 174 has in its lower end portion a tapered inner circumferential surface 174b which flares toward the lower end of the insulating tube 174. The insulating pipe 75 has a tapered outer circumferential surface 75a at its lower end portion, which flares toward the lower end of the insulating pipe 75. Hence, the lower end portion of the insulating pipe 75 can be fitted tight in the lower end portion of the insulating tube 174.

When the A-cord cap 171 is connected to the electrode pin 74, the lower end portion of the pipe 75 is fitted tight in the lower end portion of the insulating tube 174, because of the tapered inner circumferential surface 174b and the tapered outer circumferential surface 75a. Liquid such as water or physiological saline is prevented from flowing to the lower end of the pin connector 173. The interface 176 between the distal end 174a of the tube 174 and the connection portion 73 can remain dry or clear of any electrically conductive substance. Hence, the high-frequency current would not leak from the interface 176.

Figure 27B:
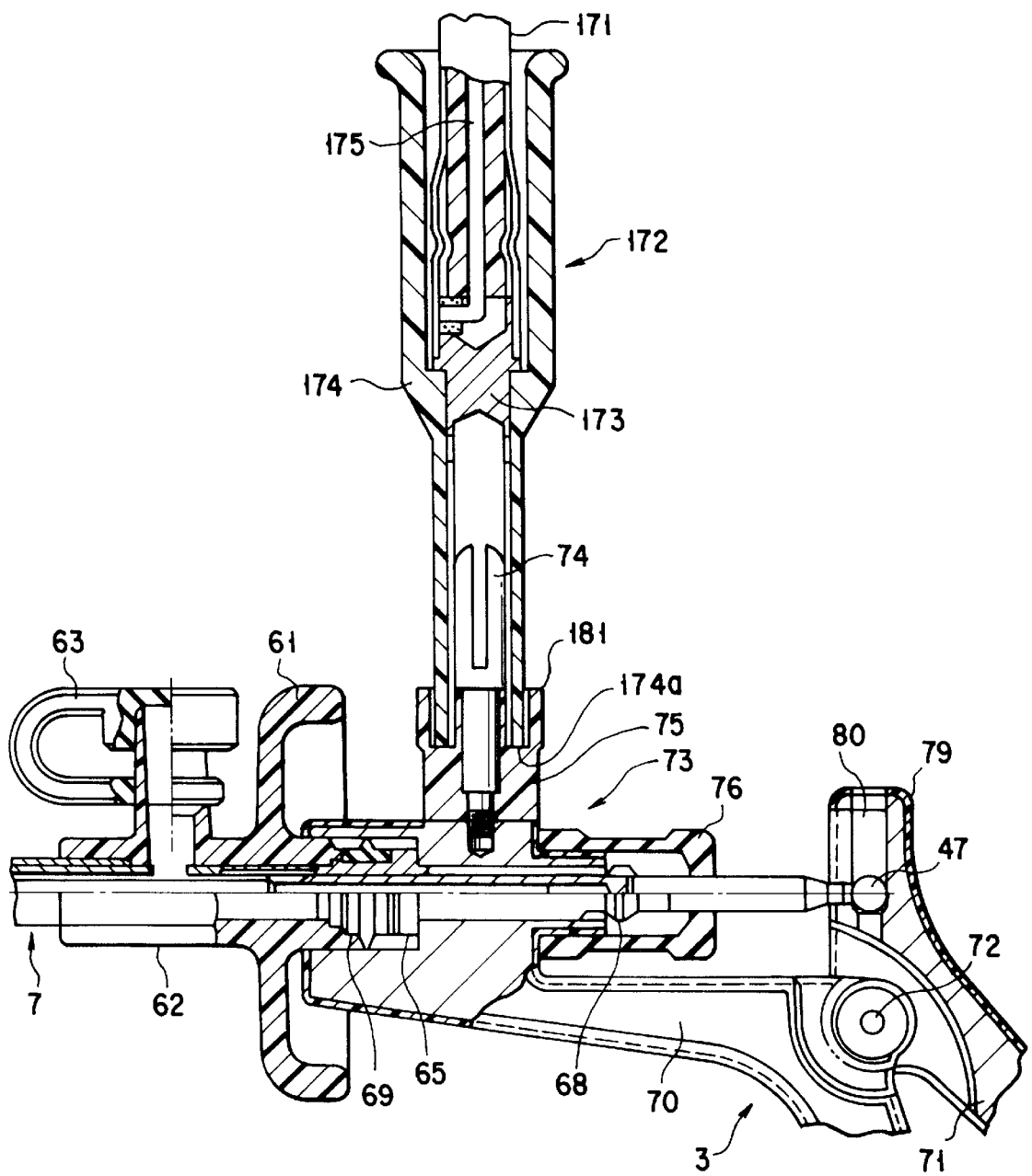
FIG. 27B is a longitudinal sectional view showing a second structure of connecting the A-cord cap to the electrode pin.

FIG. 27B shows a second structure of connecting the A-cord cap 172 to the electrode pin 74. This structure is characterized in that the insulating pipe 75 has at its top a hollow cylinder 181 which is mounted on the lower end portion of the insulating tube 174. Provided with the hollow cylinder 181, the second structure can more reliably prevent the high-frequency current from leaking from the interface 176 than does the first structure shown in FIG. 26.

Figure 28A:
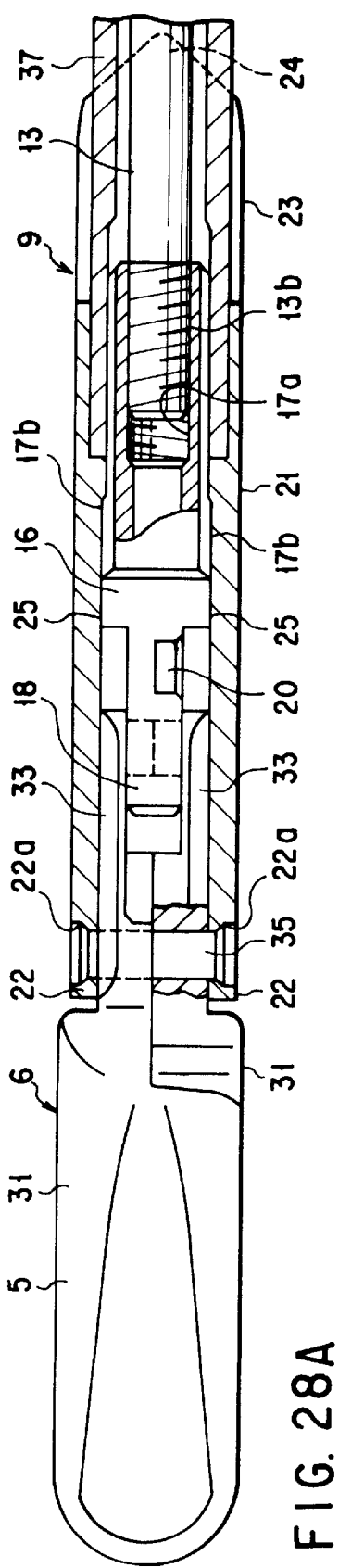
FIG. 28A is a cutaway plan view of the distal end portion of the fifth embodiment.
Figure 28B:
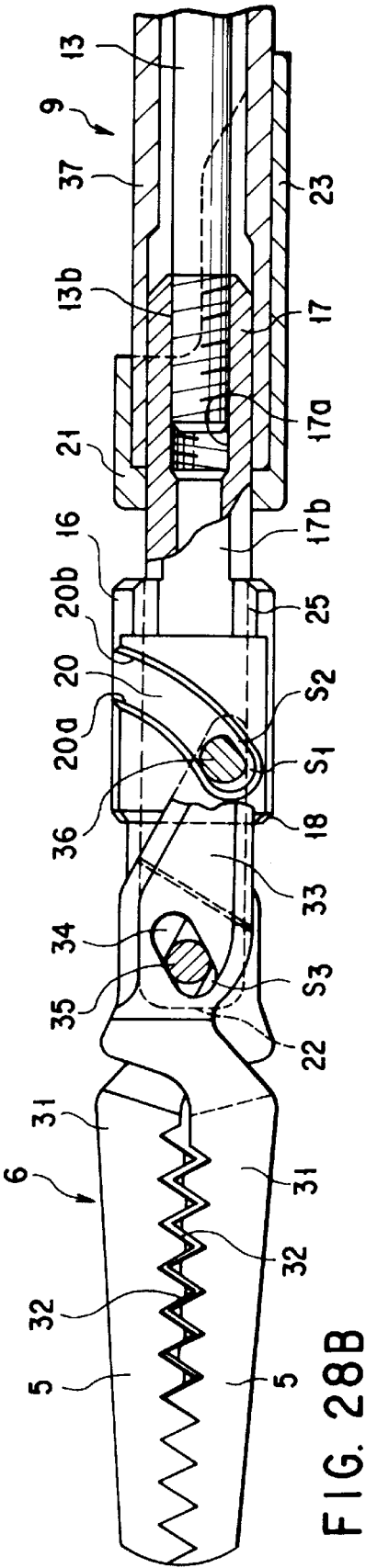
FIG. 28B is a cutaway side view of the distal end portion of the fifth embodiment.
Figure 28C:
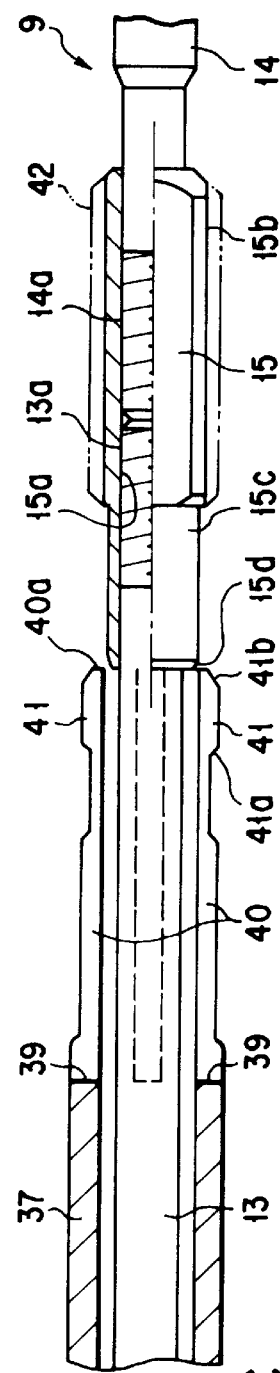
FIG. 28C is a longitudinal sectional view showing the snap-fit arm of the drive unit.

FIGS. 28A and 28B show the distal end portion of the forceps according to the fifth embodiment, and FIG. 28C illustrates the snap-fit arms of the drive unit of the fifth embodiment.

As shown in FIG. 28B, the elongated hole 34 of the link arm 33 of either tong 5 has a clearance $S_3$ which extends forward from the position the guide pin 36 assumes when the tongs 5 are closed. Except for this feature, the distal end portion of the fifth embodiment is identical to that of the first embodiment. The components identical or similar to those of the distal end portion of the first embodiment are designated at the same reference numerals in FIGS. 28A and 28B and will not be described in detail.

The clearance $S_3$ provided in the elongated hole 34 allows the tong 5 to bend elastically when a force is a closing force is applied to the tong 5 after the tongs 5 have been closed. The tongs 5 can therefore clamp a thin tissue membrane more firmly and steadily.

Figure 29A:
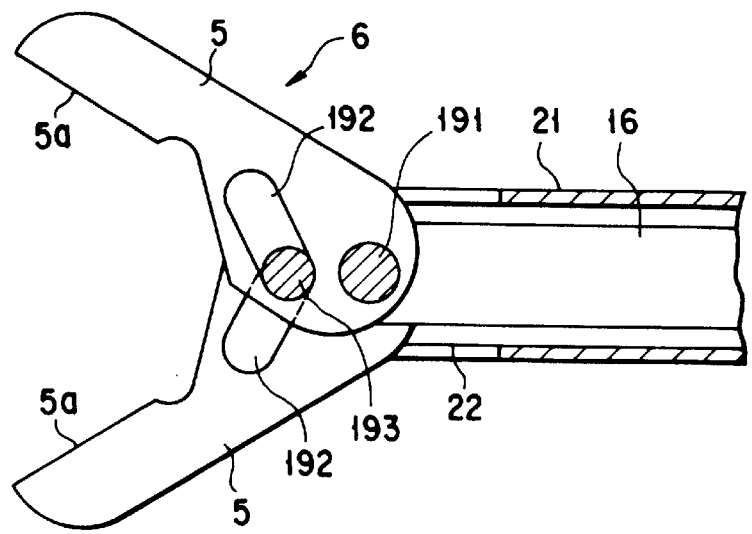
FIG. 29A is a cutaway side view of the distal end portion of a forceps according to a sixth embodiment of the invention, illustrating the tongs assuming open position.
Figure 29B:
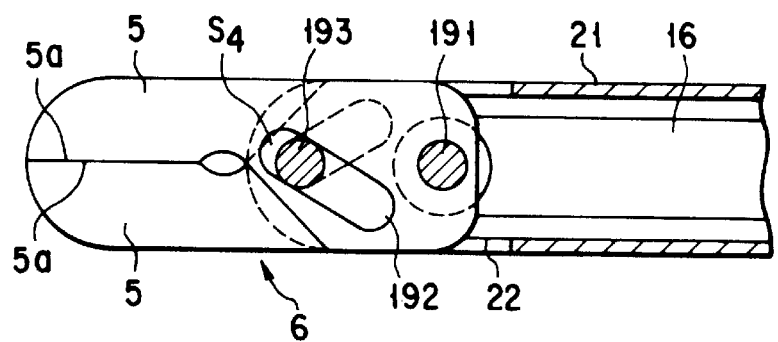
FIG. 29B is a cutaway side view, showing the tongs assuming in closed position.

A forceps according to the sixth embodiment of the present invention will now be described, with reference to FIGS. 29A and 29B. As shown in these figures, a pair of tongs 5 are rotatably coupled, at their proximal ends, by pins 191 to the distal end of a cam member 16 which is provided at the distal end of the distal shaft 13, i.e., the distal end portion of an operation shaft 12. Each tong 5 has an elongated hole 192 extending between the distal end portion 5a and the pin 191, and serving as a cam groove of a cam mechanism K. A cam pin 193 passes through the elongated holes 192 of the tongs 5.

The cam pin 193 has its ends fastened to the distal end portions of the support arms 22 of a holding member 21, respectively. The elongated hole 192 of each tong 5 is longer than necessary to allow the cam pin 193 to move while the tongs 5 are rotating from their open position shown in FIG. 29A to their closed position shown in FIG. 29B. The elongated hole 192 has a clearance $S_4$ which extends forward from the position the cam pin 193 assumes when the tongs 5 are closed. Except for these structural features, the forceps according to the sixth embodiment is identical to the first embodiment. The components identical or similar to those of the first embodiment are designated at the same reference numerals in FIGS. 29A and 29B and will not be described in detail.

To rotate the tongs 5 rom the open position (FIG. 29A) to the closed position (FIG. 29B), a surgeon rotates the movable handle 71 of the operation section 3 clockwise in FIG. 1. The operating shaft 12 of the drive unit 9 is thereby pulled backwards, pulling the pin 191 in the same direction. The pin 191 pulls the tongs 5 backwards. As they are so pulled, the tongs 5 gradually rotate toward their closed position since the cam pin 193 passing through the elongated holes 192 of both tongs 5 is fixed in place. If the surgeon further rotates the movable handle 71 after the tongs 5 have been closed, a force is applied to close the tongs 5 further. As a result, the tongs 5 elastically bend, until the clearance $S_4$ reduces to nil.

The cam pin 193 has yet to abut the distal edges of the elongated holes 192 of the tongs 5 when the distal end portions 5a of the tongs 5 contact each other. The operating shaft 12 can therefore be further pulled backwards until the clearance $S_4$ decreases to nil. Hence, the additional force applied by rotating the handle 71 is reliably transmitted to the distal end portions 5a of the tongs 5. The tongs 5 can therefore clamp a thin tissue membrane firmly and steadily.

Figure 30:
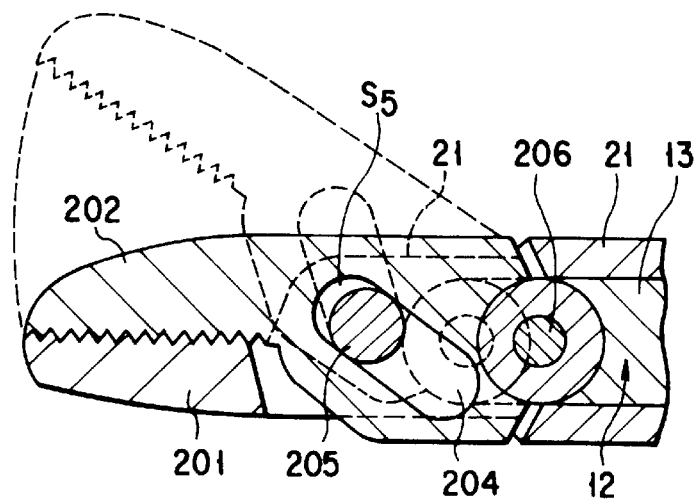
FIG. 30 is a longitudinal sectional view of the distal end portion of a forceps according to a seventh embodiment of the present invention.

FIG. 30 shows the distal end portion of a forceps according to the seventh embodiment of the invention.

As illustrated in FIG. 30, the instrument section 203 of the seventh embodiment are similar to its counterpart of the third embodiment shown in FIGS. 17A to 17G. More specifically, the instrument section 203 comprises a fixed tong 201 and a movable tong 202. The fixed tong 201 is formed integral with a holding member 21. The movable tong 202 is rotatably coupled to the fixed tong 201 by a fulcrum pin 206. The fulcrum pin 206 is fastened at one end the distal end of the distal shaft 13, i.e., a distal end portion of an operating shaft 12.

The movable tong 202 has an elongated hole (cam hole) 204. A cam pin 205 is fastened at ends to the support arms 22 of the holding member 21, passing through the elongated hole 204 of the movable tong 202. The elongated hole 204 has a clearance $S_5$ which extends forward from the position the cam pin 205 assumes when the movable tong 202 abuts on the fixed tong 201.

When the movable tong 202 rotating around the pin 206 from its open position abuts on the fixed tong 201, the cam pin 205 does not abut the distal edge of the elongated hole 204. Hence, the operating shaft 12 can be further pulled backwards as the movable handle 71 of the operation section 3 is rotated clockwise (FIG. 1), until the cam pin 205 abuts the distal edge of the elongated hole 204, reducing clearance $S_5$ reduces to nil. The additional force applied by rotating the handle 71 is reliably transmitted to the distal end portions of the movable tong 202. The tongs 201 and 202 can therefore clamp a thin tissue membrane firmly and steadily.

FIGS. 31A and 31B show the distal end portion of a forceps according to the eighth embodiment of the present invention.

As seen from FIGS. 31A and 31B, two cam pins 211 protrude from the sides of a block-shaped member 18 identical to the one incorporated in the first embodiment. The link arm 33 of either tong 5 has an elongated hole (cam hole) 212 in its distal end portion. The cam pins 211 pass through the elongated holes 212 of the link arms 33, respectively.

The holes 212 are longer than necessary to allow the cam pins 211 to move while the tongs 5 are rotating from their open position to their closed position shown in FIG. 31A. Either elongated hole 212 has a clearance $S_6$ which extends backwards from the position the cam pin 211 assumes when the tongs 5 are closed.

When the movable handle 71 of the operation section 3 is rotated counterclockwise (FIG. 1), pushing the cam member 16 forward, along with the operating shaft 12, the cam pins 211 move forward in horizontal direction through, guided by the elongated holes 212 of the link arms 33. As a result of this, both tongs 5 are rotated around the fulcrum pin 35, assuming the open position.

To rotate the tongs 5 of the instrument section 6 from the open position to the closed position shown in FIG. 31A, the surgeon rotates the movable handle 71 of the operation section 3 clockwise (FIG. 1). As the handle 71 is so rotated, the operating shaft 12 is pulled backwards, pulling the cam pins 211 of the cam member 16 backwards. The proximal end portions of both tongs 5 are thereby pulled backwards, too. As a result, the tongs 5 are rotated around the fulcrum pin 35 to the closed position, and the teeth 32 of the first tong 5 mesh with the teeth 32 of the second tong 5.

As the movable handle 71 is further rotated clockwise after the tongs 5 have been closed, the operating shaft 12 is further pulled backwards, pulling the link arms 33 backwards to reduce the clearance $S_6$ in either elongated hole 212. A force is therefore applied to both tongs 5 to close them. The tongs 5 are elastically bent to some extent.

When the tongs 5 rotating around the fulcrum pin 35 from its open position abut on each other at their teeth 32, the cam pins 211 do not abut the proximal edges of the elongated holes 212. Hence, the operating shaft 12 can be further pulled backwards as the movable handle 71 of the operation section 3 is rotated clockwise (FIG. 1), until the cam pin 211 abut the proximal edges of the elongated hole 212, reducing the clearance $S_6$ to nil. The additional force applied by rotating the handle 71 is reliably transmitted to the distal end portions of both tongs 5. The tongs 5 can therefore clamp a thin tissue membrane firmly and steadily.

FIGS. 32A, 32B and 32C show the distal end portion of a forceps according to the ninth embodiment of this invention.

As illustrated in FIG. 32C, a cam member 16 similar to the one used in the eighth embodiment (FIGS. 31A and 31B) has two flat sides 221. The member 16 is located between the support arms 22 of a holding member 21, with the flat sides 221 contacting the support arms 22.

Since its flat sides 221 contact the support arms 22, the cam member 16 is inhibited from rotating around its axis. The torque the operating shaft 12 or the cam member 16 is not transmitted to the link arms 33 of the tongs 5. Hence, the cam pins 211 of the member 16 or the link arms 33 will not be broken. Nor will the cam pins 211 slip out of the elongated holes 212 made in the link arms 33.

FIGS. 33A to 33F illustrate the distal end portion of a forceps 231 according to the tenth embodiment of the present invention.

The tenth embodiment is characterized in that the drive mechanism 8 for opening and closing the tongs 5 has a link mechanism 232 which is a parallelogram linkage, instead of the cam mechanism K employed in the first embodiment.

As shown in FIG. 33E, the link mechanism 232 has a pair of link arms 233. The link arms 233 are rotatably fastened, at their proximal end portions, the distal end of a cam member 16 by means of a fulcrum pin 234. As shown in FIG. 33D, each link arm 233 is rotatably fastened, at its distal end portion, by a fulcrum pin 235 to the proximal end of the link arm 33 of the tong 5. As illustrated in FIG. 33F, the cam member 16 similar has two flat sides 236. The member 16 is located between the support arms 22 of a holding member 21, with the flat sides 236 contacting the support arms 22.

Except for these features, the forceps according to the tenth embodiment is identical to the first embodiment. The components identical or similar to those of the first embodiment are designated at the same reference numerals in FIGS. 33A to 33F and will not be described in detail.

In operation, as the operation shaft 12 is pushed and pulled, the cam member 16 drives the link mechanism 232 to open and close the tongs 5. Since its flat sides 236 contact the support arms 22, the cam member 16 is inhibited from rotating around its axis. The torque the operating shaft 12 or the cam member 16 is not transmitted to the link arms 33 of the tongs 5. Hence, the pin 234, the link arms 233 or the link arms 33 will not be broken.

A forceps 301 according to the eleventh embodiment of the present invention will be described, with reference to FIGS. 34 to 48.

Figure 34:
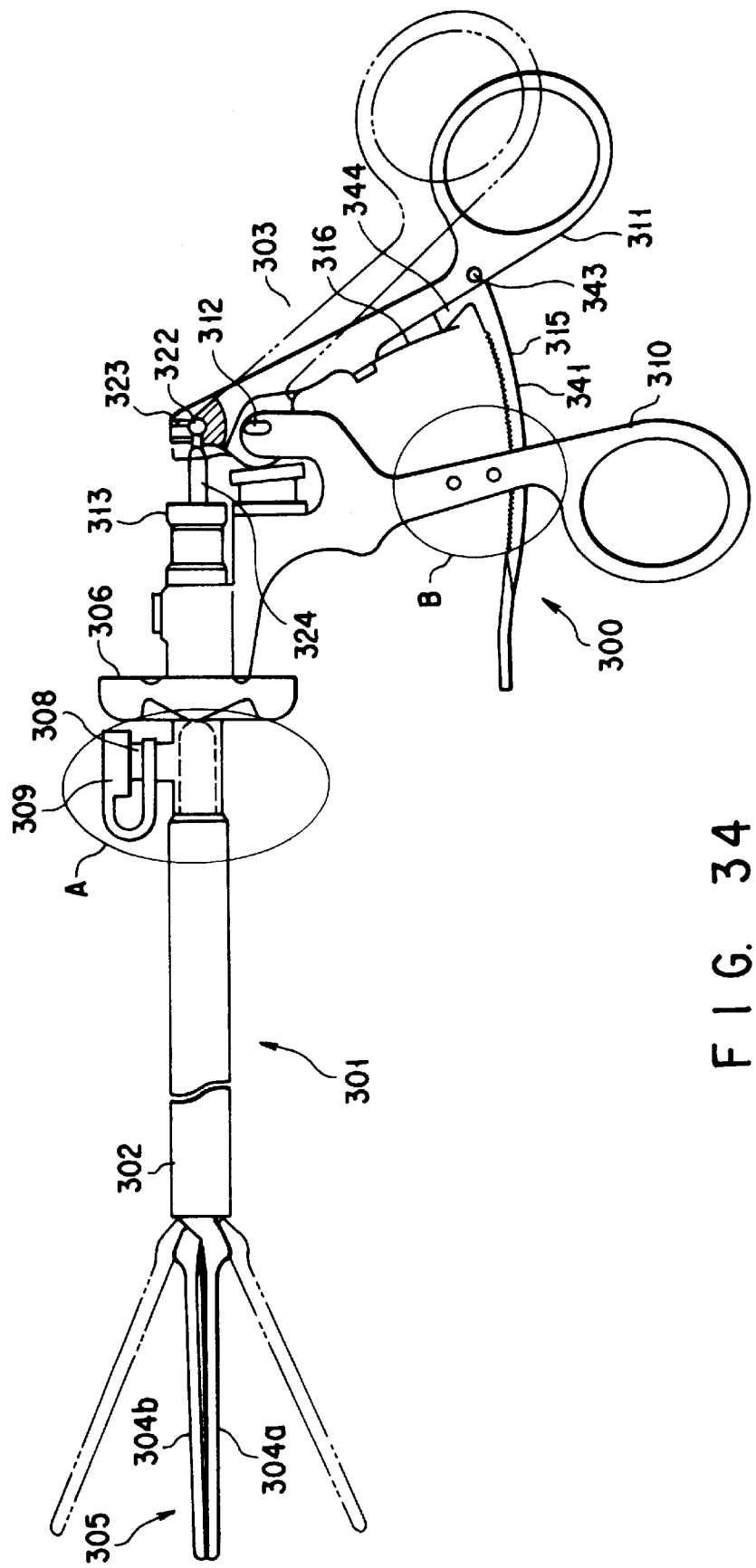
FIG. 34 is a side view illustrating a forceps according to an eleventh embodiment of the present invention.

As shown in FIG. 34, the forceps 301 has a ratchet and comprises an insertion section 302 and an operation section 303. The insertion section 302 is to be inserted into a body cavity. The operation section 303 is connected to the proximal end of the insertion section 202. Secured to the distal end of the insertion section 302 is an instrument section 305 comprised of a pair of tongs 304a and 304b.

Figure 37:
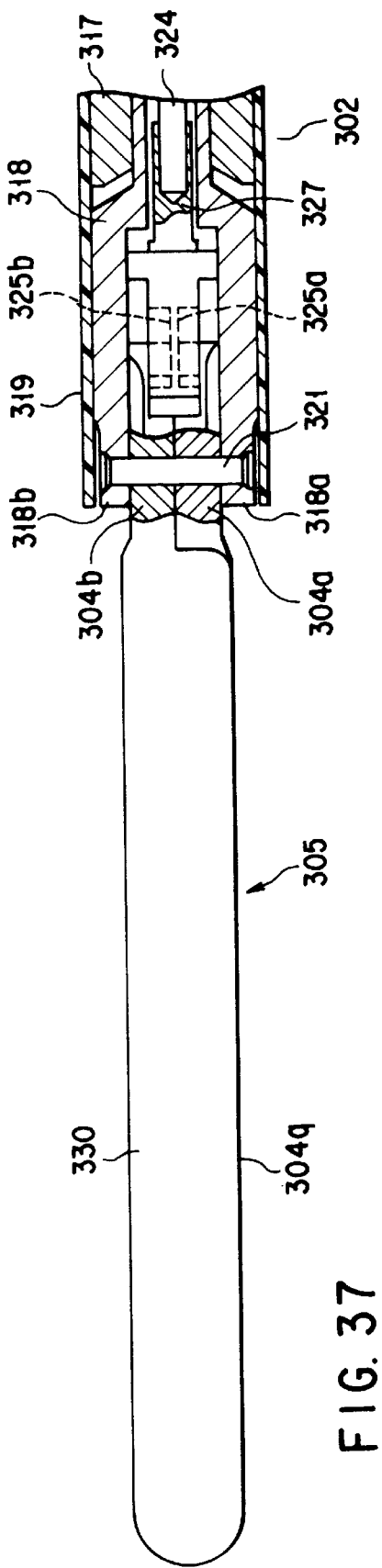
FIG. 37 is a cutaway plan view of the distal end portion of the eleventh embodiment.

As shown in FIG. 37, the insertion section 302 comprises a tubular sheath 317, a holding member 318 and an insulating tube 319. The tubular sheath 316 is made of metal such as stainless steel or resin such as polysulfone. The holding member 318 is made of metal such as stainless steel and fastened to the distal end of the sheath 316. The insulating tube 319 is made of resin such as PTFE mounted on and, thus covering both the tubular sheath 317 and the holding member 318. The holding member 318 has two support arms 318a and 318b, which protrude from the distal end of the member 318. A support pin 321 extends between the support arms 318a and 318b and secured thereto at ends, supporting the tongs 304a and 304b.

Figure 35:
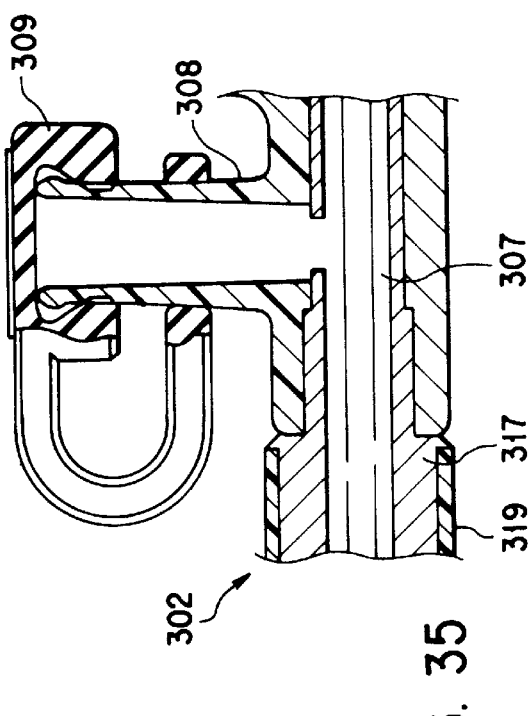
FIG. 35 is an enlarged, longitudinal sectional view of the portion A shown in FIG. 34.

As shown in FIG. 34, on the proximal end portion of the insertion section 302 there are provided a knob 306, a water-supplying cap 308 and a cap 309. The knob 306 is used to rotate the insertion section 302 and the instrument section 305 around their axes, with respect to the operation section 303. As shown in FIG. 35, the water-supplying cap 308 has communicates at its lower end with the interior 307 of the tubular sheath 317. The cap 309 is removably mounted on the top end portion of the water-supplying cap 308, preventing gas from leaking from a body cavity through the sheath 317. The cap 309 is removed, opening the water-supplying cap 308, whereby water can be supplied from the water source (not shown) connected to the cap 308 to the distal end of the insertion section 302 via the interior 307 of the tubular sheath 317.

The operation section 303 has a fixed handle 310 and a movable handle 311. The movable handle 311 is rotatably coupled to the fixed handle 310 by a support pin 312. A rubber cap 313 made of soft material such as silicone is attached to the rear end of the fixed handle 310, accomplishing airtight sealing of the tubular sheath 317.

An operating shaft 324 is movably placed within the insertion section 302, for transmitting the force applied by rotating the movable handle 311 to the instrument section 305. A spherical connector 322 is fastened to the proximal end of the operating shaft 324. The connector 322 is loosely fitted in a groove 323 made in the top of the movable handle 311 and can slide up and down in the groove 323. The connector 322 and the groove 323 transform the rotation of the movable handle 311 into linear motion of the operating shaft 324.

As illustrated in FIG. 37, the operating shaft 324 has a drive member 327 at its distal end. The drive member 327 is a rectangular block placed between the support arms 318*a* and 318*b* of the holding member 318. As shown in FIGS. 38 and 40, the member 327 has two cam grooves 325*a* and 325*b* formed in the sides. The cam grooves 325*a* and 325*b* guide the proximal ends of the tongs 304*a* and 304*b* such that the tongs open or close.

The tongs 304*a* and 304*b* of the instrument section 305 have elongated holes 320*a* and 320*b*, respectively. The support pin 321 passes through the holes 320*a* and 320*b*, whereby the tongs 304*a* and 304*b* are guided away from the axis of the insulating tube 319 as they rotate around the pin 321, from the closed position to the open position.

As shown in FIG. 40, cam pins 326*a* and 326*b* protrude inwards from the proximal end portions of the tongs 304*a* and 304*b*, respectively. The cam pins 326*a* and 326*b* are slidably inserted in the cam grooves 325*a* and 325*b* made in the sides of the drive member 327. As the drive member 327 moves along its axis, the cam pins 326*a* and 326*b* move along the cam grooves 325*a* and 325*b*, rotating the tongs 304*a* and 304*b* are rotated around the support pin 321, to the open position or the closed position.

The elongated holes 320*a* and 320*b* and the cam grooves 325*a* and 325*b* have such shapes and arranged at such positions that the following equations hold true as long as the tongs 304*a* and 304*b* remain in the closed position as illustrated in FIG. 38: $f_1 = f \cos \theta_2$ $$f_2 = f \cos \theta_1 \cdot \cos (\theta_3 - \theta^1)$$

where $f_1$ is the force acting in the tangent to the curving axis of either cam groove (325*a*, 325*b*) as shown in FIG. 42, f is the load applied forward on the operating shaft 324, $\theta_2$ is the angle between the tangent and the axis of the shaft 324, $f_2$ is the force acting along the axis of either elongated hole (320*a*, 320*b*) as shown in FIG. 42, $\theta_1$ is the angle between the axis of the operating shaft 324 and the line connecting the axis of the support pin 321 and the axis of either cam pin (326*a*, 326*b*), and $\theta_3$ is the angle between the axis of the operating shaft 324 and the axis of either elongated hole (320*a*, 320*b*).

The force $f_1$ is less than the force $f_2$ —that is, $f_1 < f_2$. Hence:

$$\cos \theta_2 < \cos \theta_1 \cdot \cos (\theta_3 - \theta^1)$$

The elongated holes 320*a* and 320*b* and the cam grooves 325*a* and 325*b* have such shapes and arranged at such positions that the following equations hold true as long as the tongs 304*a* and 304*b* remain in the fully open position as illustrated in FIG. 41: F1>F2, or $\cos \theta_5 > \cos \theta_4 \cdot \cos (\theta_6 - \theta_4)$ where $F_1$ is the force acting along the tangent to the axis of either cam groove (325*a*, 325*b*), $F_2$ is the acting along the tangent to the axis of either elongated hole (320*a*, 320*b*), and $\theta_4$, $\theta_5$ and $\theta_6$ are angles corresponding to the angles $\theta_1$, $\theta_2$ and $\theta_3$ defined above.

In order to satisfy the above conditions more reliably, each of the cam grooves 325*a* and 325*b* may have front edge $L_1$ and rear edge $L_2$ which are, as shown in FIG. 44, arcs having different centers.

The cam grooves 325*a* and 325*b* are so arranged that the cam pin 326*a* and 325*b* are located always near the love edges of the grooves 324*a* and 325*b* and, thus, below the axis of the operating shaft 324. Hence, both cam pins 326*a* and 326*b* can be moved back and forth, always along the axis of the operating shaft 324.

As shown in FIGS. 38 and 41, the tongs 304*a* and 304*b* have a bulging portion 304$_p$ each at the proximal end portion. Curving gently, the bulging portions 304$_p$ of the tongs 304*a* and 304*b* serve to achieve smooth insertion of the forceps 1 into a body cavity and smooth removal of the forceps 1 therefrom, through a trocar.

As seen from FIG. 45, the tongs 304*a* and 304*b* have tissue holding portions 304$_q$. The tissue holding portions 304$q$ are long enough (50 mm or more) to clamp large tubular tissues (e.g., the intestine), and as thin as possible but rigid enough to hold a tubular tissue steadily. The tissue-holding surface 330 have rounded lateral edges 330 so that the tissue clamped between the portions 304$q$ may not be damaged.

Figure 36:
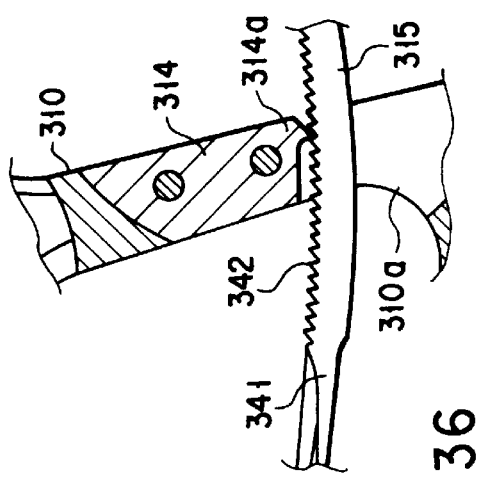
FIG. 36 is an enlarged, longitudinal side view of the portion B shown in FIG. 34.

The operation section 303 has a ratchet mechanism 300 for holding the movable handle 311 at a desired angle with respect to the fixed handle 310. As shown in FIG. 36, the ratchet mechanism 300 comprises an elongated member 314, a ratchet 315 and an arm 341. The member 314 is secured to the fixed handle 310 and has a projection 314*a*. The ratchet 315 is made of metal such as stainless steel and removably set in engagement with the elongated member 314. The arm 341 is inserted in a through hole 310*a* made in the fixed handle 310. The arm 341 has teeth 342. The projection 314*a* can slip into the gap between any adjacent two of the teeth 342, thereby to hold the ratchet 315 to the fixed handle 310.

As shown in FIG. 34, the arm 341 has an L-shaped end portion 344. At the L-shaped portion 344 the arm is coupled by a pin 343 to the movable handle 311 and can rotate around the pin 343. A leaf spring 316 is fastened at one end to the movable handle 311. The other end of the leaf spring 316 contacts the L-shaped portion 344. The spring 316 and biases the ratchet 315, keeping the projection 314*a* of the elongated member 314 in the gap between any adjacent two of the teeth 342. The movable handle 311 is thereby held at a desired angle with respect to the fixed handle 310.

The ratchet 315 is so designed that the arm 341 rotates downwards (FIG. 34) against the force of the leaf spring 316 to release the projection 314*a* of the member 314 from the teeth 342. Once the projection 314*a* is released from the teeth 342, the movable handle 311 be rotated freely.

How the forceps 301 is operated will be explained.

When a surgeon rotates the movable handle 311 away from the fixed handle 310, the spherical connector 322 slides forward, whereby the operating shaft 324 is pushed forward. The drive member 327 converts the forward motion of the shaft 324 to the rotation of tongs 304*a* and 304*b*. More precisely, the the elongated holes 320*a* and 320*b* first moved linearly forwards, pushing both tongs 304*a* and 304*b* linearly. This is because the force the shaft 324 exerts along the tangent of the axis of the elongated holes 320*a* and 320*b* is greater than the force applied to the cam pins 326*a* and 326*b*. Then, the cam pins secured to the tongs 304*a* and 304*b* slide along the cam grooves 325*a* and 325*b*, whereby the tongs 304*a* and 304*b* are rotated around the support pin 321 to the open position.

Conversely, when the surgeon rotates the movable handle 311 toward the fixed handle 310, the spherical connector 322 slides backward, pulling the operating shaft 324 backward. The drive member 327 converts the backward motion of the shaft 324 to the rotation of tongs 304*a* and 304*b*. To state more precisely, the the elongated holes 320*a* and 320*b* first moved linearly backwards, pulling both tongs 304*a* and 304*b* linearly. This is because the force the shaft 324 exerts along the tangent of the axis of the elongated holes 320*a* and 320*b* is smaller than the force applied to the cam pins 326*a* and 326*b*. Then, the cam pins secured to the tongs 304*a* and 304*b* slide along the cam grooves 325*a* and 325*b*, whereby the tongs 304*a* and 304*b* are rotated around the support pin 321 to the closed position.

As the operating shaft 324 is further pulled backward after the tongs 304a and 304b have rotated to be parallel to each other as illustrated in FIG. 46, the elongated holes 320a and 320b move parallel to the axis of the operating shaft 324. As a result, the tongs 304a and 304b approach each other, not rotating around the support pin 321. The tongs 304a and 304b therefore apply a uniform force on the tubular tissue 331 clamped between the tongs 304a and 304b. The tubular tissue 331 is thereby held steadily in its entirely.

When the drive member 327 is pushed forward in the direction of arrow 332 shown in FIG. 48 to open the tongs 304a and 304b, the cam pins 326a and 326b are move upward in the direction of arrow 333. This is because the cam pins 326a and 326b are always located above the axis S of the operating shaft 324. The cam pins 326a and 326b are moved downward when the drive member 327 is pulled backward to close the tongs 304a and 304b.

As indicated above, the the tongs 304a and 304b are first rotated to be parallel to each other as the operating shaft 324 is pulled backward, and then approach approach each other, not rotating around the support pin 321, as the operating shaft 324 is further pulled backward. The gap provided between the tongs 304a and 304b after the tongs are placed parallel to each other can be adjusted in accordance with the wall thickness of the tubular tissue 331 which the tongs 304a and 304b are to clamp. In other words, the forceps 301 according to the eleventh embodiment can reliably clamp and collapse the tubular tissue 331, regardless of the wall thickness of the tubular tissue 331.

The cam grooves 325a and 325b are moved always in the same direction, and so are the cam pins 326a and 326b. Therefore, the operating shaft 324 can apply a force to the tongs 304a and 304b smoothly, and the cam pins 326a and 326b exert but a very small force to the edges of the cam grooves 325a and 325b, respectively. The friction between either cam pin and the cam a groove is small.

The eleventh embodiment may be modified. For instance, one of the tongs may be a fixed one, while the other tong may be a movable one. Furthermore, the operating shaft 324 may be made of super elasticity alloy which is a which is a shape-memory alloy. If the shaft 324 is made of super elasticity alloy, it will be elastically elongated when the surgeon rotates the movable handle 311 toward the fixed handle 310 with an excessively large force. As the shaft 324 is so elongated, the projection 314a of the elongated member 314 slips out of the gap between two adjacent teeth 342 into the next gap between the teeth 342, without increasing the clamping force of the tongs 304a and 304b. Hence, the ratchet 315 can hold the movable handle 311 at such a position that the tongs 304a and 304b clamp the tissue 331 with a desired force, despite the relatively long fixed pitch of the teeth 342 on the ratchet 315. It is unnecessary to reduce the pitch of the teeth 342. Having teeth arranged at a long pitch, the ratchet 315 is mechanically stronger than otherwise. Since the ratchet 325 has a comparatively small number of teeth, the ratchet mechanism 300 can be manufactured at low cost.

A forceps 351 according to the twelfth embodiment of the invention will be described, with reference to FIGS. 49 and 50 which illustrate the distal end portion of the forceps.

Figure 49:
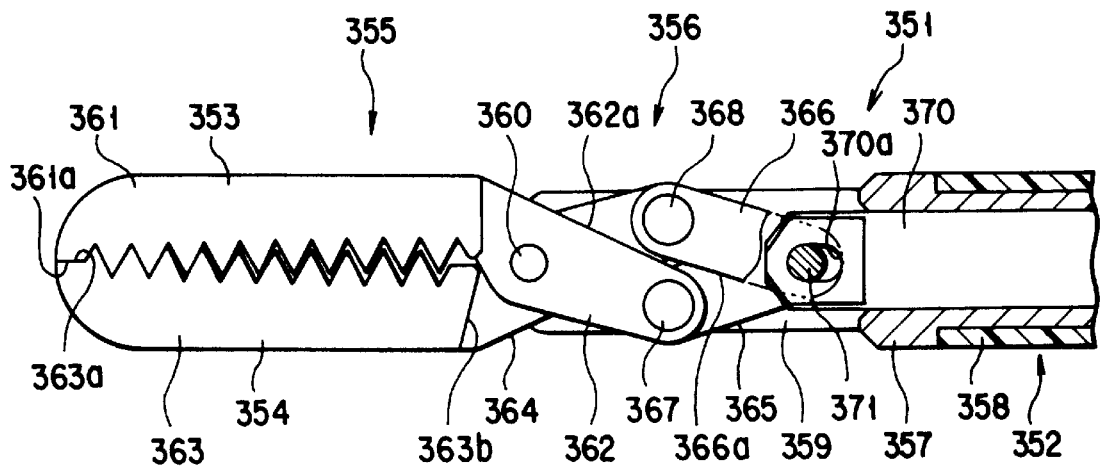
FIG. 49 is a cutaway side view showing the distal end portion of a forceps according to a twelfth embodiment of the invention, showing the tongs closed a link mechanism.
Figure 50:
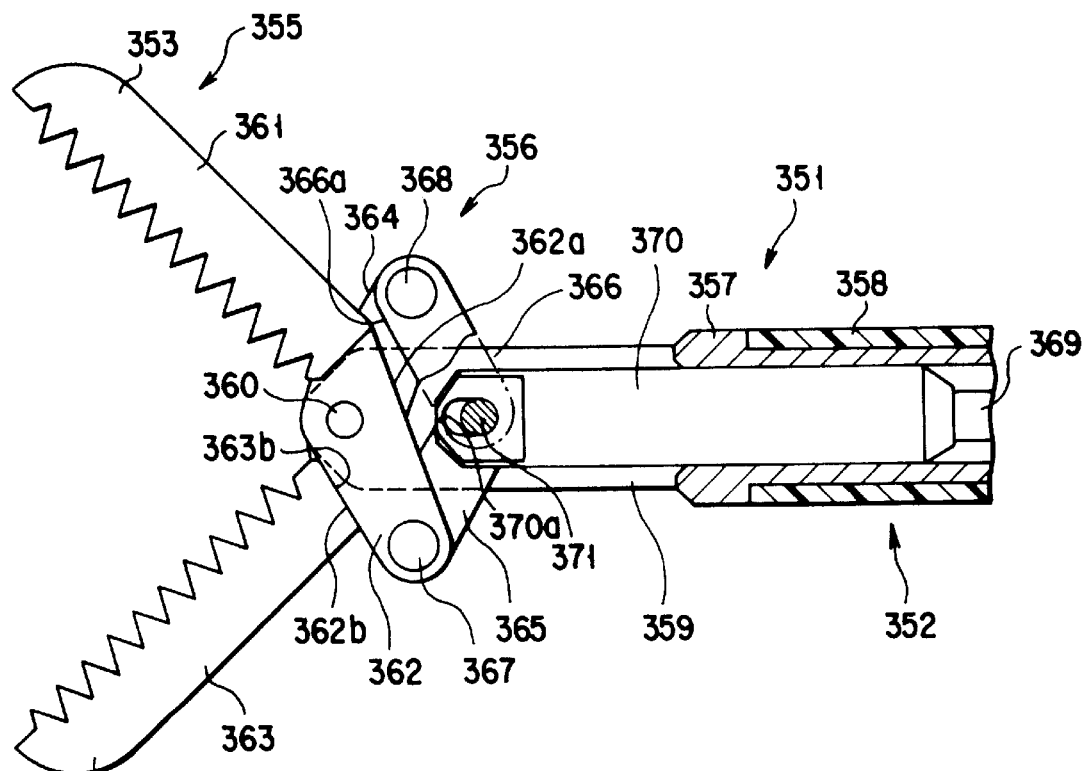
FIG. 50 is a cutaway side view showing the distal end portion of the twelfth embodiment, illustrating the tongs opened by the link mechanism.

As shown in FIGS. 49 and 50, an instrument section 355 is connected to the distal end of the insertion section 352. The instrument section 355 comprises a pair of tongs 353 and 354 and a four-link drive mechanism 356 for driving the tongs 353 and 354.

The insertion section 352 comprises a long tubular sheath 357, an insulating tube 358, a pair of holding members 359. The insulating tube 358 is mounted on the sheath 357. The holding members 359 project parallel to each other from the distal end of the tubular sheath 357, holding the four-link mechanism 356 between them. Two support pins 360 protrude toward the axis of the sheath 357 from the distal end portions of the holding members 359. The support pins 360 support the tongs 353 and 354, which can rotate around the pins 360.

The first tong 353 consists of a main body 361 having teeth and a coupling arm 362 connected to the proximal end of the main body 361. Similarly, the second tong 354 consists of a main body 363 having teeth and a coupling arm 364 connected to the proximal end of the main body 363. The proximal end portions of both coupling arms 362 and 364 are located between the holding members 359 of the insertion section 352.

The link mechanism 356 has two intermediate links 365 and 366. The first intermediate link 365 has its distal end connected by a first pin 367 to the distal end portion of the coupling arm 362. Similarly, the second intermediate link 366 has its distal end connected by a second pin 368 to the distal end portion of the coupling arm 364.

As shown in FIG. 50, an operating shaft 369 can move back and forth through the tubular sheath 357. The shaft 369 is connected at its proximal end to an operation section 303 of the type shown in FIG. 34, and at its distal end to the a drive shaft 370. The intermediate links 365 and 366 are rotatably coupled to the distal end of the drive shaft 370 by a third pin 371.

When the tongs 353 and 354 are closed as shown in FIG. 49, their main bodies 361 and 363 abut on each other at the distal end portions 361a and 363a. In this state, the back 362a of the coupling arm 362 is spaced apart from the side 366a of the second intermediate link 366, providing a space between them. This space allows the tongs 353 and 354 to rotate to close further. The third pin 371 is inserted in an elongated hole 370a made in the drive shaft 370. The hole 370a is longer than the diameter of the third pin 371. The hole 370a and the third pin 371 therefore define an ineffective stroke.

When the tongs 353 and 354 are opened, the side 362b of the coupling arm 362 of the first tong 353 contacts the shoulder 363b of the main body 363 of the second tong 354. In this state, the back 362a of the coupling arm 362 is spaced apart from the side 366a of the second intermediate link 366, providing a space between them. This space allows the tongs 353 and 354 to rotate to open further. The third pin 371 is inserted in an elongated hole 370a made in the drive shaft 370. The hole 370a is longer than the diameter of the third pin 371. FIG. 50 shows the tongs 353 and 354 further opened, after the third pin 371 has moved over the ineffective stroke.

If a surgeon exerts an excessively large force on the movable handle 311 to close the tongs 353 and 354, the four-link drive mechanism 356 will be deformed, reducing the the space between the back 362a of the coupling arm 362 and the side 366a of the second intermediate link 366, even after the main bodies 361 and 363 abut on each other at the distal end portions 361a and 363a. Thus deformed, the mechanism 356 absorbs the excessively large force the surgeon has exerted on the movable handle 311.

Conversely, if the surgeon exerts an excessively large force on the movable handle 311 to open the tongs 353 and 354, the four-link drive mechanism 356 will be deformed, reducing the the space between the back 362a of the coupling arm 362 and the side 366a of the second intermediate link 366, even after the main bodies 361 and 363 are fully open, with the side 362b of the coupling arm 362 and the shoulder 363b of the main body 363 abutting on each other. Thus deformed, the mechanism 356 absorbs the excessively large force the surgeon has exerted on the movable handle 311.

Since the four-link drive mechanism 356 can be actuated even after the tongs 353 and 354 have been closed or opened completely, the forceps 351 can attain the same advantages as the first embodiment which incorporates a cam mechanism.

The forceps 351 may be modified to have either the tong 353 or the tong 354 fixed and immovable. In this case, it suffices to use only one half of the four-link drive mechanism 356.

Figure 51:
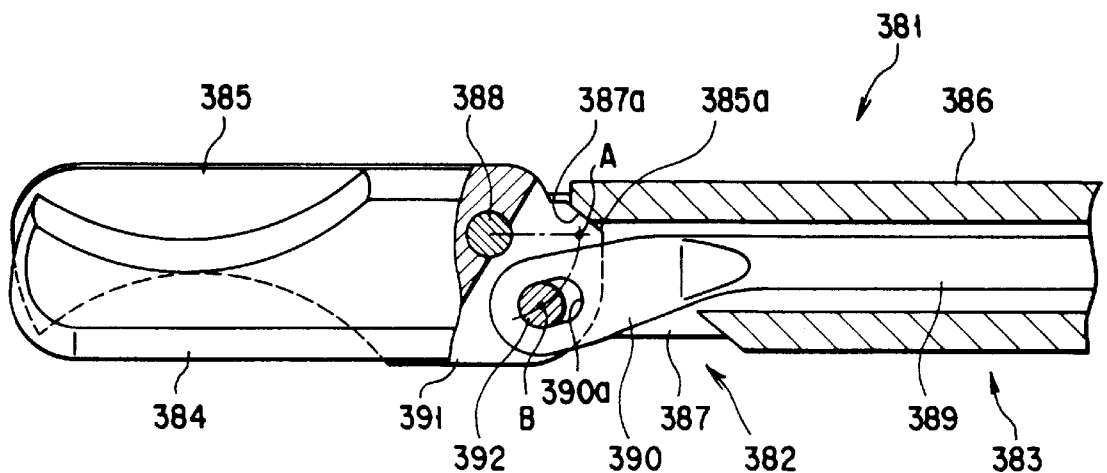
FIG. 51 is a cutaway side view showing the distal end portion of a forceps according to a thirteenth embodiment of the invention, showing the tongs assuming closed position.

FIG. 51 is a cutaway side view showing the distal end portion of a forceps according to a thirteenth embodiment of the invention, showing the tongs assuming closed position; and A forceps 381 which is the thirteenth embodiment of the invention will be described, with reference to FIGS. 51 and 52 which show the distal end portion of the forceps.

The forceps 381 has a link drive mechanism 382, which differs from the four-link drive mechanism 356 in that it has no intermediate links for coupling the drive shaft to two tongs.

As shown in FIG. 51, the fixed jaw 384 is fastened to the distal end of the insertion section 383. A movable jaw 385 is rotatably coupled by a first pin 388 to the proximal end portion of the fixed jaw 384. More precisely, the insertion section 383 has a long tubular sheath 386, and the fixed jaw 384 has its proximal end formed integral with the distal end of the tubular sheath 386.

The tubular sheath 386 contains an operating shaft 389, which can move back and forth in the axial direction. The link drive mechanism 382 includes a drive member 390, which is coupled to the distal end of the operating shaft 389. The drive member 390 is partly inserted in a slot 387 made in the fixed jaw 384. The movable jaw 385 is rotatably coupled by a second pin 392 to the distal end portion of the drive member 390.

As the operating shaft 389 is pushed forward, it pushes the drive member 390 forward. The drive member 390 pushes the second pin 392 forward, rotating the movable jaw 385 around the first pin 388 to the open position. As the operating shaft 389 is pulled backward, it pulls the drive member 390 backward. The drive member 390 in turn pulls back the second pin 392, rotating the movable jaw 385 around the first pin 388 to the closed position.

The rear end 385a of the movable jaw 385 is held in contact with the rear edge 387a of the slot 387 made in the fixed jaw 384 as long as the movable jaw 385 remains in the closed position as shown in FIG. 51. In this state, the movable jaw 385 and the drive member 390 constitute a slider-crank mechanism, in which point A shown in FIG. 51 is equivalent to the top dead center. If the rear end of the movable jaw 385 did not contact the rear edge 387a of the slot 387, nothing would restrict the motion of the slider-crank mechanism at all, and the axis of the second pin 392 could be located at point A. However, the axis of the pin 392 remains at point B since the rear end of the movable jaw 385 contacts the rear edge 387a of the slot 387. Hence, the drive member 390 can apply a force to the movable jaw 385 even after the movable jaw 385 has rotated to the closed position.

Figure 52:
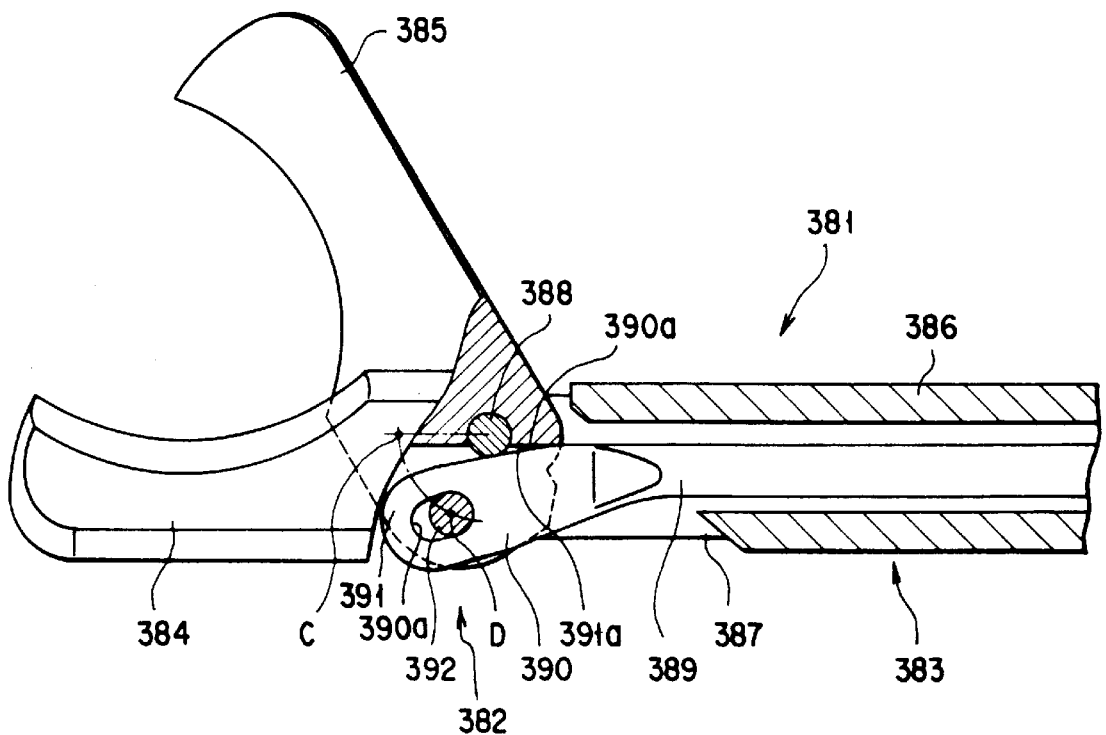
FIG. 52 is a cutaway side view showing the distal end portion of the thirteenth embodiment, illustrating the tongs assuming open position.

The back 390a of the drive member 390 is held in contact with the front 391a of the slot 391 made in the movable jaw 385 as long as the movable jaw 385 remains in the open position as shown in FIG. 52. In this state, the movable jaw 385 and the drive member 390 constitute a slider-crank mechanism, in which point C shown in FIG. 52 is equivalent to the bottom dead center. If the back 390a of the drive member 390 did not contact the front 391a of the slot 391, nothing would restrict the motion of the slider-crank mechanism, and the axis of the second pin 392 could be located at point C. However, the axis of the pin 392 remains at point D since the back 390a of the drive member 390 contacts the front 391a of the slot 391, Hence, the drive member 390 can apply a force to the movable jaw 385 even after the movable jaw 385 has rotated to the open position.

Since the link drive mechanism 383 can be actuated even after the movable jaw 385 have been closed or opened completely, the forceps 381 can attain the same advantages as the first embodiment which incorporates a cam mechanism. In addition, the link drive mechanism 383 has an ineffective stroke which is equivalent to the backlash provided in the third embodiment.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A medical instrument comprising:
    an insertion section to be inserted into a body cavity through an instrument-inserting channel of an endoscope;
    a pair of treating members connected to a distal end of the insertion section;
    an operation section connected to a proximal end of the insertion section for opening and closing the treating members;
    an operating shaft extending through the insertion section, and wherein said operation section includes shaft-moving means for moving said operating shaft back and forth in said insertion section; and
    drive means including a cam mechanism for opening and closing said treating members when said operating shaft is moved back and forth, and for applying an additional force to said treating members even after said treating members have come to abut on each other; and
    wherein said cam mechanism comprises cam grooves and cam pins for moving along the cam grooves, respectively, said cam grooves being longer than is necessary to move said treating members between an open position and a closed position where said treating members abut on each other.

2. The medical instrument according to claim 1, wherein said insertion section has an outer sheath, wherein said drive means further includes a distal cover which supports said operating shaft such that said operating shaft is movable back and forth in an axial direction, and a support pin supporting said treating members, and wherein each of said treating members has a proximal end portion having an elongated support hole for receiving said support pin, and a cut-away portion between the proximal end portion of said treating members 10 and said outer sheath of said insertion section.

3. The medical instrument according to claim 1, wherein said drive means further includes a distal cover which supports said operating shaft such that said operating shaft is movable back and forth in an axial direction, S and a support pin supporting said treating members, and wherein each of said treating members has a proximal end portion having an elongated support hole for receiving said support pin, and a weak portion located closer to a proximal end of said treating members than the support hole.

4. The medical instrument according to claim 3, wherein each of said treating members includes a link arm from which a cam pin protrudes, and wherein said weak portion has a cross section which is taken along a plane perpendicular to an axis of said operating shaft and which has a narrowest part located between the cam pin and the support hole.

5. The medical instrument according to claim 1, wherein said drive means includes a distal cover which supports said operating shaft such that said operating shaft is movable back and forth in an axial direction, and a coupling member which is connected to a distal end of said operating shaft, said coupling member having a projection abutting on inner sides of both arms of said distal cover and said coupling member being capable of withstanding a moment of a couple generated from a reaction from a cam pin.

6. A medical instrument comprising:
   an insertion section to be inserted into a body cavity through an instrument-inserting channel of an endoscope, said insertion section including a sheath unit;
   a pair of openable and closable treating members connected to a distal end of the insertion section;
   an operation section connected to a proximal end of the insertion section;
   an operating shaft extending through the insertion 10 section, and wherein said operation section includes shaft-moving means for moving said operating shaft back and forth in said insertion section;
   drive means, provided between said operating shaft and said treating members and including a cam mechanism, for opening and closing said treating members when said operating shaft moves back and forth in said insertion section, and for applying an additional force to said treating members even after said treating members have come to abut on each other;
   a drive unit connecting said treating members to said drive means; and
   unit-connecting means provided between said sheath unit of said insertion section and at least one of said drive unit and said operation section for removably connecting said sheath unit to at least one of the drive unit and said operation section; and
   wherein said cam mechanism comprises cam grooves and cam pin for moving along the cam grooves, respectively, said cam grooves being longer than is necessary to move said treating members between an open position and a closed position where said treating members abut on each other.

7. The medical instrument according to claim 6, wherein said unit connecting means comprises:
   an arm supported at at least one end thereof, said arm extending between said sheath unit and at least one of said drive unit and said operation section;
   an engagement recess provided in one of said sheath unit and at least one of said drive unit and said operation section; and
   an engagement projection protruding in a direction other than a direction in which said arm extends, said engagement projection being removably fitted in said engagement recess.

8. The medical instrument according to claim 7, wherein said unit-connecting means further comprises deforming-preventing means abutting on an inner side of said arm and preventing said arm from being deformed to extend inward.

9. The medical instrument according to claim 8, wherein said deforming-preventing means comprises a hollow cylinder secured to said operating shaft and having an outer diameter equal to an inner diameter of said arm.

10. The medical instrument according to claim 9, further comprising position-adjusting means for adjusting a position of said operating shaft, said position-adjusting means being provided at at least one of a junction with said coupling member and a junction with said hollow cylinder.

11. The medical instrument according to claim 10, wherein said position-adjusting means comprises a screw mechanism including a male screw and a female screw.

12. The medical instrument according to claim 6, wherein one of the units removably connected together by said unit-connecting means has a first positioning portion having a semi-circular cross section and extending in an axial direction of said operating shaft, and the other of said units has a second positioning portion for positioning the units with respect to a rotation direction of the units.

13. The medical instrument according to claim 12, wherein said operating shaft has a spherical portion at a proximal end, said operation section has a fixed handle and a movable handle rotatably coupled to the fixed handle, said movable handle having an engagement hole for receiving the spherical portion of said operating shaft, and said first and second positioning portions having a length at least equal to a distance between a position at which said spherical portion enters said engagement hole and a position at which said movable handle fully opens said treating members.

14. The medical instrument according to claim 13, wherein said movable handle has a groove formed in a portion contacting said fixed handle and a passage communicating with a bottom of said engagement hole.

15. The medical instrument according to claim 13, wherein said movable handle comprises a head in which said engagement hole is formed and which stands upright while said treating members are one of clamping an object and peeling an object from another object, and wherein said engagement hole extends at substantially right angles to an axis of said insertion section.

16. The medical instrument according to claim 13, wherein said treating members comprise a pair of scissors for cutting an object, and said movable handle comprises a head in which said engagement hole is formed and which stands upright while said treating members are clamping an object, and wherein said engagement hole extends at a substantially right angle to an axis of said insertion section.

17. The medical instrument according to claim 13, wherein said fixed handle has an electrode-connecting portion, and wherein a connecting portion of an electric cord to be connected to the electrode-connecting portion has a holder section large enough to cover an insulating cover mounted on said electrode-connecting portion.

18. The medical instrument according to claim 6, wherein said operating shaft comprises a super elasticity alloy.

19. The medical instrument according to claim 6, wherein:
   said drive unit has a first positioning portion having a semi-circular cross section and extending in an axial direction of said operating shaft,
   said sheath unit has a second positioning portion having a cross section of a shape corresponding to the first positioning portion, said first and second positioning portions position the units removably connected together by said unit-connecting means with respect to a rotation direction of the units, said operating shaft has a spherical portion at a proximal end, said operation section has a fixed handle and a movable handle rotatably coupled to the fixed handle, said movable handle having an engagement hole for receiving the spherical portion of said operating shaft, and further comprising an assembly-assisting mechanism having a length such that the spherical portion of said operation shaft remains entered in the engagement hole of said movable handle when a proximal end of said first positioning portion abuts on a distal end of said second positioning portion.

20. A medical instrument for use in combination with an endoscope, comprising:

an insertion section to be inserted into a body cavity;

a pair of treating members rotatably connected by a support shaft to a distal end of said insertion section;

an operation section connected to a proximal end of said insertion section for opening and closing said treating members;

an operating shaft extending through said insertion section, said operating shaft being movable back and forth when said operation section is operated; and drive means including a cam mechanism for opening and closing said treating members in response to a linear motion of said operation shaft when said operation section is operated, and for applying an additional force to said treating members even after said treating members have come to abut on each other, wherein said operating shaft is elastically deformed when said operation section is operated to open and close said treating members; and wherein said cam mechanism comprises cam grooves and cam pins for moving along the cam grooves, respectively, said cam grooves being longer than is necessary to move said treating members between an open position and a closed position where said treating members abut on each other.

21. The medical instrument according to claim 20, wherein said operating shaft comprises an elastic material.

22. The medical instrument according to claim 21, wherein said elastic material comprises a super elasticity alloy.

23. The medical instrument according to claim 20, wherein said operating shaft includes means for enabling a movable handle of said operation section to rotate through an angle greater than is necessary to close said treating members.

24. A medical instrument comprising:

an insertion section to be inserted into a body cavity through an instrument-inserting channel of an endoscope;

a pair of treating members connected to a distal end of the insertion section;

an operation section connected to a proximal end of the insertion section for opening and closing the treating members;

an operating shaft extending through the insertion section, and wherein said operation section includes shaft-moving means for moving said operating shaft back and forth in said insertion section; and drive means including a cam mechanism for opening and closing said treating members when said operating shaft is moved back and forth, and for applying an additional force to said treating members even after said treating members have come to abut on each other, wherein said drive means includes a support pin supporting said treating members, and each of said treating members has a proximal end portion having an elongated support hole for receiving said support pin; and wherein said cam mechanism comprises cam grooves and cam pins for moving along the cam grooves, respectively, said cam grooves being longer than is necessary to move said treating members between an open position and a closed position where said treating members abut on each other.

* * * * *

UNITED STATES PATENT AND TRADEMARK OFFICE
CERTIFICATE OF CORRECTION

PATENT NO. : 5,849,022
DATED : December 15, 1998
INVENTOR(S) : Kiyotoshi SAKASHITA et al It is certified that error appears in the above-identified patent and that said Letters Patent is hereby corrected as shown below:

<u>On the Title page</u>

Column 2, line 2, change "5,020,056 5/1991"
to --5,250,056 10/1993--.

Under "FOREIGN PATENT DOCUMENTS", line 5, delete "U-8 900 376 4/1989 Germany"; and line 7, delete "U-9 106 506 9/1991 Germany".

Signed and Sealed this

Ninth Day of November, 1999

*Attest:*

Q. TODD DICKINSON

*Attesting Officer*   Acting Commissioner of Patents and Trademarks